US006914049B2

(12) United States Patent
Mascarenhas

(10) Patent No.: US 6,914,049 B2
(45) Date of Patent: Jul. 5, 2005

(54) IGF-BINDING PROTEIN-DERIVED PEPTIDE OR SMALL MOLECULE

(75) Inventor: Desmond Mascarenhas, Los Altos Hills, CA (US)

(73) Assignee: Bioexpertise, LLC, Sunnyvale, CA (US)

(*) Notice: Subject to any disclaimer, the term of this patent is extended or adjusted under 35 U.S.C. 154(b) by 73 days.

(21) Appl. No.: 10/383,999

(22) Filed: Mar. 7, 2003

(65) Prior Publication Data

US 2003/0224990 A1 Dec. 4, 2003

Related U.S. Application Data

(63) Continuation of application No. 10/264,672, filed on Oct. 4, 2002, which is a continuation-in-part of application No. 10/215,759, filed on Aug. 9, 2002.
(60) Provisional application No. 60/323,267, filed on Sep. 18, 2001.

(51) Int. Cl.⁷ .............................................. A61K 38/00
(52) U.S. Cl. ............................................ 514/12; 435/6
(58) Field of Search .................................. 514/2; 435/6

(56) References Cited

U.S. PATENT DOCUMENTS

| | | | |
|---|---|---|---|
| 5,187,151 A | 2/1993 | Clark et al. |
| 5,407,913 A | 4/1995 | Sommer et al. |
| 5,527,776 A | 6/1996 | Carlino et al. |
| 5,643,867 A | 7/1997 | Maack et al. |
| 5,681,818 A | 10/1997 | Spencer et al. |
| 5,723,441 A | 3/1998 | Higley et al. |
| 5,840,673 A | 11/1998 | Buckbinder et al. |
| 5,861,273 A | 1/1999 | Olson et al. |
| 5,914,254 A | 6/1999 | Mascarenhas et al. |
| 5,929,040 A | 7/1999 | Werther et al. |
| 6,015,786 A | 1/2000 | Mascarenhas et al. |
| 6,417,330 B1 | 7/2002 | Mascarenhas et al. |
| 6,428,781 B1 | 8/2002 | Sakano et al. |
| 2002/0165155 A1 | 11/2002 | Schaffer et al. |
| 2003/0035788 A1 | 2/2003 | Mascarenhas |
| 2003/0092631 A1 | 5/2003 | Deshayes et al. |

FOREIGN PATENT DOCUMENTS

| | | |
|---|---|---|
| EP | 0 128 733 | 12/1984 |
| EP | 0 597 033 | 2/1993 |
| WO | WO 95/03817 | 2/1995 |
| WO | WO 95/13823 | 5/1995 |
| WO | WO 96/02565 | 2/1996 |
| WO | WO 00/23469 | 4/2000 |
| WO | WO 01/87238 | 11/2001 |
| WO | WO 02/24216 | 3/2002 |
| WO | WO 02/34916 | 5/2002 |

OTHER PUBLICATIONS

Adams, S. et al. (1995). "Pharmacokinetics and Bioavailability of rhIGF–I/IGFBP–3 in the Rat and Monkey," *Prog. Growth Factor Res.* 6(2–4):347–356.

Altschul, S.F. et al. (1990). "Basic Local Alignment Search Tool," *J. Mol. Biol.* 215:403–410.

Asin, J. et al. (2000). "Iron (II) Induces Changes in the Conformation of Mammalian Mitochondrial DNA Resulting in a Reduction of its Transcriptional Rate," *FEBS Letters* 480:161–164.

Ausubel, F. et al. eds. (1987). *Current Protocols in Molecular Biology* Greene Publishing Associates and Wiley–Interscience: New York. (Table of Contents Only.)

Bartfay, W.J. et al. (1999). "A Biochemical, Histochemical, and Electron Microscopic Study on the Effects of Iron–Loading on the Hearts of Mice," *Cardiovascular Pathology* 8(6):305–314.

Baxter, R.C. (1988). "Characterization of the Acid–Labile Subunit of the Growth Hormone–Dependent Insulin–Like Growth Factor Binding Protein Complex," *J. Clin. Endocrinol. Metab.* 67(2):265–272.

Baxter, R.C. et al. (1986). "Growth Hormone–Dependent Insulin–Like Growth Factor (IGF) Binding Protein from Human Plasma Differs from Other Human IGF Binding Proteins," *Biochem. Biophys. Res. Comm.* 139(3):1256–1261.

Baxter, R.C. et al. (1989). "High Molecular Weight Insulin–Like Growth Factor Binding Protein Complex," *J. Biol. Chem* 264(20):11843–11848.

Bayes–Genis, A. et al. (2001). "Insulin–Like Growth Factor Binding Protein–4 Protease Produced by Smooth Muscle Cells Increases in the Coronary Artery After Angioplasty," *Arterioscler. Thromb. Vasc. Biol.* 21:335–341.

Blum, W.F. and Ranke, M.B. (1991). "Plasma IGFBP–3 Levels as Clinical Indicators" In *Modern Concepts of Insulin–Like Growth Factors* Spencer, E.M. ed., Elsevier: New York. pp. 381–393.

Boles, B.K. et al. (2000). "Phorbol Ester–Induced U–937 Differentiation: Effects on Integrin $\alpha_3$ Gene Transcription," *Am. J. Physiol. Lung Cell Mol. Physiol.* 278:L703–L712.

Butler, A.A. et al. (1998). "Stimulation of Tumor Growth by Recombinant Human Insulin–Like Growth Factor–I (IGF–I) Is Dependent on the Dose and the Level of IGF–I Receptor Expression," *Cancer Res.* 58:3021–3027.

Byun, D. et al. (2001). "Pregnancy–Associated Plasma Protein–A Accounts for the Insulin–Like Growth Factor (IGF)–Binding Protein–4 (IGFBP–4) Proteolytic Activity in Human Pregnancy Serum and Enhances the Mitogenic Activity of IGF by Degrading IGFBP–4 in Vitro," *J. Clin. Endocrinol. Metabl.* 86(2):847–854.

(Continued)

Primary Examiner—Christopher R. Tate
Assistant Examiner—Maury Audet
(74) Attorney, Agent, or Firm—Morrison & Foerster LLP

(57) ABSTRACT

New compositions based on IGF-binding protein sequences are provided. New tools for high-throughput research are provided. New methods for the treatment of human disease are provided. IGFBP-3-derived peptide or small molecule is administered to subjects having disease, thereby alleviating the symptoms of the disease.

27 Claims, 24 Drawing Sheets

OTHER PUBLICATIONS

Campbell, P.G. et al. (1998). "Plasminogen Binds the Heparin–Binding Domain of Insulin–Like Growth Factor–Binding Protein–3," *Am. J. Physiol.* 275(2pt. 1):E321–E331.

Campbell, P.G. et al. (1999). "Insulin–Like Growth Factor–Binding Protein–3 Binds Fibrinogen and Fibrin," *J. Biol. Chem.* 274(42):30215–30221.

Collett–Solberg, P.F. et al. (1998). "Identification of Novel High Molecular Weight Insulin–Like Growth Factor–Binding Protein–3 Association Proteins in Human Serum," *J. Clin. Endocrinol. Metab.* 83(8):2843–2848.

Conover, C.A. et al. (2001). "Pregnancy–Associated Plasma Protein–A is the Insulin–Like Growth Factor Binding Protein–4 Protease Secreted by Human Ovarian Granulosa Cells and Is a Marker of Dominant Follicle Selection and the Corpus Luteum," *Endocrinology* 142(5):2155–2158.

Coppack, S.W. (2001). "Pro–Inflammatory Cytokines and Adipose Tissue," *Proc. Nutr. Soc.* 60:349–356.

Crofford, L.J. (May, 2002). "Specific Cyclooxygenase–2 Inhibitors: What Have We Learned Since They Came Into Widespread Clinical Use?" *Curr. Opin. Rheumatol.* 13:225–230.

Degertekin, M. et al. (Sep., 2002). "Persistent Inhibition of Neointimal Hyperplasia After Sirolimus–Eluting Stent Implantation," *Circulation* 106:1610–1613.

Durham, S.K. et al. (1999). "The Heparin Binding Domain of Insulin–Like Growth Factor Binding Protein (IGFBP)–3 Increases Susceptibility of IGFBP–3 to Proteolysis," *Horm. Metab. Res.* 31:216–225.

Eliceiri, B.P. and Cheresh, D.A. (2000). "Role of αv Integrins During Angiogenesis," *The Cancer Journal* 6(Supp. 3):S245–S249.

Favoni, R. E. et al. (1998). "Modulation of the Insulin–Like Growth Factor–I System by N–(4–Hydroxyphenyl)–Retinamide in Human Breast Cancer Cell Lines," *Br. J. Cancer* 77(12):2138–2147.

Felding–Habermann, B. et al. (2001). "Integrin Activation Controls Metastasis in Human Breast Cancer," *Proc. Natl. Acad. Sci. USA* 98(4):1853–1858.

Ferrucci, J.T. (1991). "Iron Oxide Enhanced MR Imaging of the Liver and Spleen: Review of the First Five Years," *Keio J. Med.* 40(4):206–214.

Ferry, R.J. et al. (1999). "Cellular Actions of Insulin–Like Growth Factor Binding Proteins," *Horm. Metab. Res.* 31:192–202.

Firth, S.M. et al. (1998). "Structural Determinants of Ligand and Cell Surface Binding of Insulin–Like Growth Factor–Binding Protein–3," *J. Biol. Chem.* 273(5):2631–2638.

Fowlkes, J.L. and Serra, D.M. (1996). "Characterization of Glycosaminoglycan–Binding Domains Present in Insulin––Like Growth Factor–Binding Protein–3," *J. Biol. Chem.* 271(25):14676–14679.

Fowlkes, J.L. et al. (1995). "Insulin–Like Growth Factor (IGF)–Binding Protein–3 (IGFBP–3) Functions as an IGF–Reversible Inhibitor of IGFBP–4 Proteolysis," *J. Biol. Chem.* 270(46):27481–27488.

Fowlkes, J.L. et al. (1997). "Heparin–Binding, Highly Basic Regions Within the Thyroglobulin Type–1 Repeat of Insulin–Like Growth Factor (IGF)–Binding Proteins (IGFBPs)–3, –5, and –6 Inhibit IGFBP–4 Degradation," *Endocrinology* 138(6):2280–2285.

Futterman, L.G. and Lemberg, L. (Sep., 2002). "High–Sensitivity C–Reactive Protein Is the Most Effective Prognostic Measurement of Acute Coronary Events," *American Journal of Critical Care* 11(5):482–486.

Genbank accession No. BC031217, Jun. 13, 2002, located at <http://www.ncbi.nlm.nih.gov/entrez/query.fcgi?cmd=Retrieve&db=nucleotide&list_uids=21411477&dopt=GenBank> visited on Feb. 14, 2003. (Two pages.)

Ghosh, P. et al. (1995). "The Structure of an Intermediate in Class II MHC Maturation: CLIP Bound to HLA–DR3," *Nature* 378:457–462.

Gill, Z.P. et al. (1997). "Insulin–Like Growth Factor–Binding Protein (IGFBP–3) Predisposes Breast Cancer Cells to Programmed Cell Death in a Non–IGF–Dependent Manner," *J. Biol. Chem.* 272(41):25602–25607.

Giuliano, M. et al. (1998). "Induction of Apoptosis in Human Retinoblastoma Cells by Topoisomerase Inhibitors," *Invest. Ophthalmol. Vis. Sci.* 39(8):1300–1311.

Green, D.A. et al. (2001). "Inhibition of Malignant Cell Growth by 311, a Novel Iron Chelator of the Pyridoxal Isonicotinoyl Hydrazone Class: Effect on the R2 Subunit of Ribonucleotide Reductase," *Clinical Cancer Research* 7:3574–3579.

Gribmle, R.F. (Sep., 2002). "Inflammatory Status and Insulin Resistance," *Curr. Opin. Clin. Nutr. Metab. Care* 5:551–559.

Hilger, I. et al. (2002). "Thermal Ablation of Tumors Using Magnetic Nanoparticles: An In Vivo Feasibility Study," *Investigative Radiology* 37(10):580–586.

Horwitz, L.D. et al. (1998). "Lipophilic Siderophores of *Mycobacterium Tuberculosis* Prevent Cardiac Reperfusion Injury," *Proc. Natl. Acad. Sci. USA* 95:5263–5268.

Illera, M.J. et al. (2000). "Blockade of the $α_vβ_3$ Integrin Adversely Affects Implantation in the Mouse," *Biol. Reprod.* 62:1285–1290.

Jacques, G. et al. (1997). "Nuclear Localization of Insulin–Like Growth Factor Binding Protein 3 In A Lung Cancer Cell Line," *Endocrinology* 138(4):1767–1770.

Karas, M. et al. (1997). "Membrane–Associated Insulin–Like Growth Factor–Binding Protein–3 Inhibits Insulin–Like Growth Factor–I–Induced Insulin–Like Growth Factor–I Receptor Signaling in Ishikawa Endometrical Cancer Cells," *J. Biol. Chem.* 272(26):16514–16520.

Kato, I. et al. (1999). "Iron Intake, Body Iron Stores and Colorectal Cancer Risk in Women: A Nested Case–Control Study," *Int. J. Cancer* 80:693–698.

Kelley, K.W. et al. (1998). "Insulin Growth Factor–I Inhibits Apoptosis in Hematopoietic Progenitor Cells: Implications in Thymic Aging," *Ann. N.Y. Acad Sci.* 840:518–524.

Laukaitis, C.M. et al. (2001). "Differential Dynamics of α5 Integrin, Paxillin, and α–Actinin During Formation and Disassembly of Adhesions in Migrating Cells," *J. Cell Biol.* 153(7):1427–1440.

Leal, S.M. et al. (1997). "The Type V Transforming Growth Factor β Receptor Is the Putative Insulin–Like Growth Factor–Binding Protein 3 Receptor," *J. Biol. Chem.* 272(33):20572–20576.

Lee, C.Y. and Rechler, M.M. (1995). "Purified Rat Acid–Labile Subunit and Recombinant Human Insulin–Like Growth Factor (IGF)–Binding Protein–3 Can Form a 150–Kilodalton Binary Complex in Vitro in the Absence of IGFs" *Endocrinology* 136(11):4982–4989.

Libby, P. et al. (Mar. 5, 2002). "Inflammation and Atherosclerosis," *Circulation* 105:1135–1143.

Liu, B. et al. (2000). "Direct Functional Interactions Between Insulin–Like Growth Factor–Binding Protein–3 and Retinoid X Receptor–α Regulate Transcriptional Signaling and Apoptosis," *J. Biol. Chem.* 275(43):33607–33613.

Logroscino, G. et al. (1997). "Altered Systemic Iron Metabolism in Parkinson's Disease," *Neurology* 49:714–717.

Mack, M.G. et al. (2002). "Superparamagnetic Iron Oxide–Enhanced MR Imaging of Head and Neck Lymph Nodes," *Radiology* 222(1):239–244.

Maile, L.A. et al. (1999). "The Role of Cell Surface Attachment and Proteolysis in the Insulin–Like Growth Factor (IGF)–Independent Effects of IGF–Binding Protein–3 on Apoptosis in Breast Epithelial Cells," *Endocrinology* 140(9):4040–4045.

McCaig, C. et al. (2002). "Differential Interactions Between IGFBP–3 and Transforming Growth Factor–Beta (TGF–β) in Normal vs Cancerous Breast Epithelial Cells," *Br. J. Cancer* 86:1963–1969.

Miyakoshi, N. et al. (2001). "Systemic Administration of Insulin–Like Growth Factor (IGF)–Binding Protein–4 (IGFBP–4) Increases Bone Formation Parameters in Mice by Increasing IGF Bioavailability via an IGFBP–4 Protease–Dependent Mechanism," *Endocrinology* 142(6):2641–2648.

Mohseni–Zadeh, S. and Binoux, M. (1997). "Insulin–Like Growth Factor (IGF) Binding Protein–3 Interacts with the Type 1 IGF Receptor, Reducing the Affinity of the Receptor for its Ligand: An Alternative Mechanism in the Regulation of IGF Action," *Endocrinology* 138(12):5645–5648.

Morris, C.J. et al. (1995). "Reactive Oxygen Species and Iron—A Dangerous Partnership in Inlammation," *Int. J. Biochem. Cell. Biol.* 27(2):109–122.

Nichols, T.C. et al. (1999). "Reduction in Atherosclerotic Lesion Size in Pigs by αvβ3 Inhbitors Is Associated With Inhibition of Insulin–Like Growth Factor–I—Mediated Signaling," *Circ. Res.* 85:1040–1045.

Nickerson, T. et al. (1997). "Insulin–Like Growth Factor Binding Protein–3 Induces Apoptosis in MCF7 Breast Cancer Cells," *Biochem. Biophys. Res. Comm.* 237(3):690–693.

Niu, G. et al. (Mar. 27, 2002). "Constitutive Stat3 Activity Up–Regulates VEGF Expression and Tumor Angiogenesis," *Oncogene* 21:2000–2008.

Parkes, J.G. et al. (1997). "Characterization of $Fe^{2+}$ and $Fe^{3+}$ Transport by Iron–Loaded Cardiac Myocytes," *Toxicology* 117:141–151.

Perks, C.M. et al. (1999). "Differential IGF–Independent Effects of Insulin–Like Growth Factor Binding Proteins (1–6) on Apoptosis of Breast Epithelial Cells," *J. Cell Biochem.* 75:652–664.

Perks, C.M. et al. (2002). "A Non–IGF Binding Mutant of IGFBP–3 Modulates Cell Function in Breast Epithelial Cells," *Bioch. Biophys. Res. Comm.* 294:988–994.

Pfaff, M. and Jurdic, J. (2001). "Podosomes in Osteoclast––Like Cells: Structural Analysis and Cooperative Roles of Paxillin, Proline–Rich Tyrosine Kinase 2 (Pyk2) and Integrin αvβ3,", *J. Cell Sci.* 114(15):2775–2786.

Portera, C.A. et al. (2000). "Targeting the Insulin–Like Growth Factor Axis in the Therapy of Colorectal Carcinoma Liver Metastasis," *Growth Hormone & IGF Research 2000* Suppl.A:S47–S48.

Putz, E. et al. (1999). "Phenotypic Characteristics of Cell Lines Derived from Disseminated Cancer Cells in Bone Marrow of Patients with Solid Epithelial Tumors: Establishment of Working Models for Human Micrometastases," *Cancer Res.* 59:241–248.

Rajah, R. et al. (1995). "Insulin–Like Growth Factor Binding Protein (IGFBP) Proteases: Functional Regulators of Cell Growth," *Prog. Growth Factor Res.* 6(2–4):273–284.

Rajah, R. et al. (1997). "Insulin–Like Growth Factor (IGF)–Binding Protein–3 Induces Apoptosis and Mediates the Effects of Transforming Growth Factor–β1 on Programmed Cell Death Through a p53– and IGF–Independent Mechanism," *J. Biol. Chem.* 272(18):12181–12188.

Rinderknecht, E. and Humbel, R.E. (1976). "Polypeptides and Nonsuppressible Insulin–Like and Cell–Growth Promoting Activities in Human Serum: Isolation, Chemical Characterization, and Some Biological Properties of Forms I and II," *Proc. Natl. Acad. Sci. USA* 73(7):2365–2369.

Rivera, G.M. et al. (2001). "A Potential Role for Insulin–Like Growth Factor Binding Protein–4 Proteolysis in the Establishment of Ovarian Follicular Dominance in Cattle," *Biol. Reprod.* 65:102–111.

Rosenthal, E.A. et al. (2001). "An Iron–Binding Exochelin Prevents Restenosis Due to Coronary Artery Balloon Injury in a Porcine Model," *Circulation* 104:222–2227.

Sambrook, J. et al. eds. (1989). *Molcular Cloning: A Laboratory Manual* Second edition. Cold Spring Harbor Laboratory Press: Cold Spring Harbor, New York. vol. 1–3. (Table of Contents Only.)

Schedlich, L.J. et al. (1998). "Insulin–Like Growth Factor–Binding Protein (IGFBP)–3 and IGFBP–5 Share a Common Nuclear Transport Pathway in T47D Human Breast Carcinoma Cells," *J. Biol. Chem.* 273(29):18347–18352.

Schmitz, S.A. et al. (2001). "Magnetic Resonance Imaging of Atherosclerotic Plaques Using Superparamagnetic Iron Oxide Particles," *Journal of Magnetic Resonance Imaging* 14:355–361.

Shinkai, M. et al. (2001). "Targeting Hyperthermia for Renal Cell Carcinoma Using Human MN Antigen–Specific Magnetoliposomes," *Jpn. J. Cancer Res.* 92:1138–1145.

Simonart, T. et al. (2002). "Antiproliferative and Apoptotic Effects of Iron Chelators on Human Cervical Carcinoma Cells," *Gynecologic Oncology* 85(1):95–102.

Singh, N.P. and Lai, H. (2001). "Selective Toxicity of Dihydroartemisinin and Holotransferrin Toward Human Breast Cancer Cells," *Life Sciences* 70:49–56.

Sommer, A. et al. (1991). "Molecular Genetics and Actions of Recombinant Insulin–Like Growth Factor Binding Protein–3," *In Modern Concepts of Insulin–Like Growth Factors,* Spencer, E.M. ed., Elsevier: New York. pp. 715–728.

Szabo, S.J. et al. (2000). "A Novel Transcription Factor, T–Bet, Directs Th1 Lineage Commitment," *Cell* 100:655–669.

Talks, K.L. et al. (2000). "The Expression and Distribution of the Hypoxia–Inducible Factors HIF–1α and HIF–2α in Normal Human Tissues, Cancers, and Tumor–Associated Macrophages," *Am. J. Pathol.* 157(2):411–421.

Taupitz, M. et al. (1993). "MR Lymphography Using Iron Oxide Particles," *Acta Radiologica* 34(1):10–15.

Toms, S.A. et al. (1998). "Antagonist Effect of Insulin–Like Growth Factor I on Protein Kinase Inhibitor–Mediated Apoptosis in Human Glioblastoma Cells in Association with bcl–2 and bcl–$x_L$," *J. Neurosurg.* 88:884–889.

Weber, J. et al. (1988). "Decreased Iron Absorption in Patients with Active Rheumatoid Arthritis, With and Without Iron Deficiency," *Annals of the Rheumatic Diseases* 47:404–409.

Weinzimer, S.A. et al. (2001). "Transferrin Is an Insulin–Like Growth Factor–Binding Protein–3 Binding Protein," *J. Clin Endocrinol. Metab.* 86(4):1806–1813.

Williams, A.C. et al. (2000). "Increased p53–Dependent Apoptosis by the Insulin–Like Growth Factor Binding Protein IGFBP–3 in Human Colonic Adenoma–Derived Cells," *Cancer Res.* 60:22–27.

Xu, F. et al. (1997). "Multiple Myeloma Cells are Protected Against Dexamethasone–Induced Apoptosis by Insulin–Like Growth Factors," *Br. J. Haematol.* 97:429–440.

Yang, D.C. et al. (2002). "Antisense Ferritin Oligonucleotides Inhibit Growth and Induce Apoptosis in Human Breast Carcinoma Cells," *Anticancer Research* 22:1513–1524.

Yang, Y.W–H. et al. (1996). "Heparin Inhibition of Insulin–Like Growth Factor–Binding Protein–3 Binding to Human Fibroblasts and Rat Glioma Cells: Role of Heparan Sulfate Proteoglycans," *Endocrinology* 137(10):4363–4371.

Zadeh, S.M. and Binoux, M. (1997). "The 16–kDa Proteolytic Fragment of Insulin–Like Growth Factor (IGF) Binding Protein–3 Inhibits the Mitogenic Action of Fibroblast Growth Factor on Mouse Fibroblasts with a Targeted Disruption of the Type 1 IGF Receptor Gene," *Endocrinology* 138(7):3069–3072.

Zawada, W.M. et al. (1998). "Growth Factors Improve Immediate Survival of Embryonic Dopamine Neurons After Transplantation into Rats," *Brain Res.* 786:96–103.

International Search Report mailed on Nov. 5, 2004, for PCT Patent Application No. PCT/US03/31223 filed on Oct. 2, 2003, six pages.

Figs. 1A-1B

FIG. 1A: IGFBP-3 SEQUENCE:

GASSAGLGPVVRCEPCDARALAQCAPPPAV
CAELVREPGCGCCLTCALSEGQPCGIYTER
CGSGLRCQPSPDEARPLQALLDGRGLCVNA
SAVSRLRAYLLPAPPAPGNASESEEDRSAG
SVESPSVSSTHRVSDPKFHPLHSKIIIKK
GHAKDSQRYKVDYESQSTDTQNFSSESKRE
TEYGPCRREMEDTLNHLKFLNVLSPRGVHI
PNCDKKGFYKKKQCRPSKGRKRGFCWCVDK
YGQPLPGYTTKGKEDVHCYSMQSK

FIG. 1B: [N109D]-IGFBP-3 SEQUENCE:

GASSAGLGPVVRCEPCDARALAQCAPPPAV
CAELVREPGCGCCLTCALSEGQPCGIYTER
CGSGLRCQPSPDEARPLQALLDGRGLCVNA
SAVSRLRAYLLPAPPAPGDASESEEDRSAG
SVESPSVSSTHRVSDPKFHPLHSKIIIKK
GHAKDSQRYKVDYESQSTDTQNFSSESKRE
TEYGPCRREMEDTLNHLKFLNVLSPRGVHI
PNCDKKGFYKKKQCRPSKGRKRGFCWCVDK
YGQPLPGYTTKGKEDVHCYSMQSK

Fig. 2

| CD74 Invariant Chain | RPKCDENGNYLPLQCYGSI----GYCWCVFPNGTEVPNTRSRGHHNC |
|---|---|
| | *   **   **  ***** |
| IGFBP-3 | ################### |
| | IPNCDKKGFYKKKQCRPSKGRKRGFCWCVDKYGQPLPGYTTKGKEDVHC |
| hNidogen | IPQCDEQGNFLPLQCHGST----GFCWCVDPDGHEVPGTQTPPGSTPPHC |
| hOsteonectin | IPRCNEEGYYKATQCHGST----GQCWCVDKYGNELAGSRKQGAVSC |
| hSmoc-2 | IPECAHGGLYKPVQCHPST----GYCWCVLVDTGRPIPGTSTRYEQPKC |
| Frog Saxiphilin | IPQCDEKGNYQPQQCHGST----GHCWCVNAMGEKISGTNTPPGQTRATC |
| Trout Pin | IPTCDAAGQYTPKQCWGSA----GYCWCVTSTGQKIQGTETPPGTAPINC |
| Salmon Pin | IPTCDYNGQYTPEQCWGST----GYCWCVNSSGQKLPGTDTPPGSASNC |
| hUnknown | IPECNDDGTYSQVQCHSYT----GYCWCVTPNGRPISGTAVAHKTPRC |

Fig. 4A
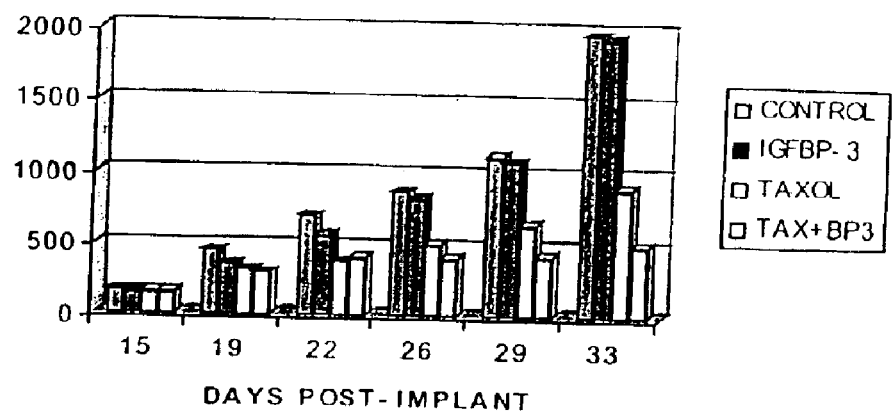
DAYS POST-IMPLANT
Fig. 4B
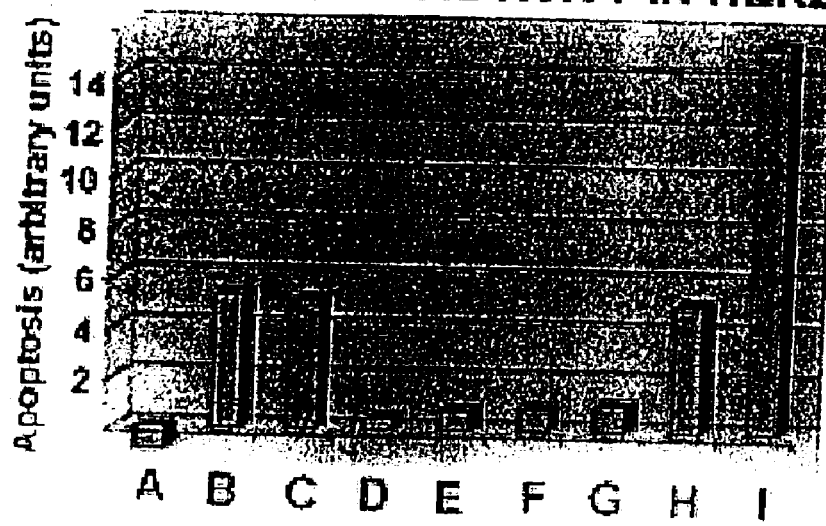
Figs. 4A-4B

Fig. 6
Original IGFBP-3 molecule
Engineered IGFBP-3 molecule (2 versions)
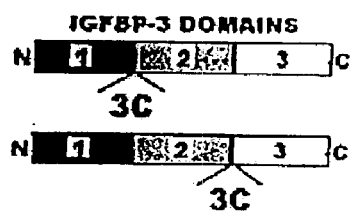
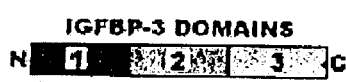
Constructs were expressed, crude extracts digested with 3C proteinase and IGFBP-3 domains captured via Phenyl-Sepharose HIC and Ni-NTA chromatography steps.
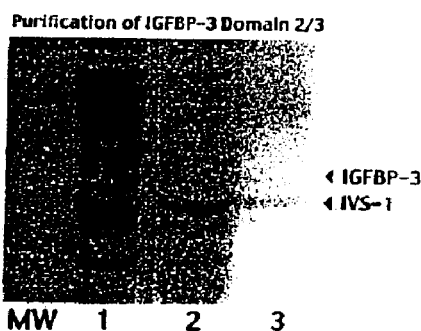

Fig. 8A
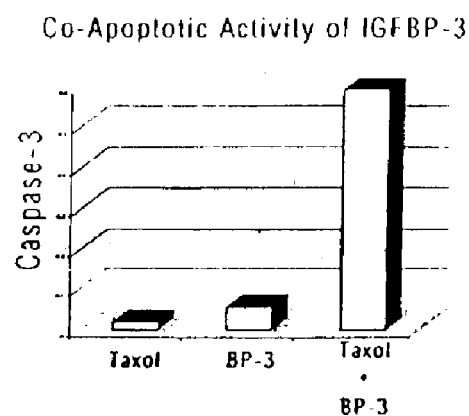
Fig. 8B
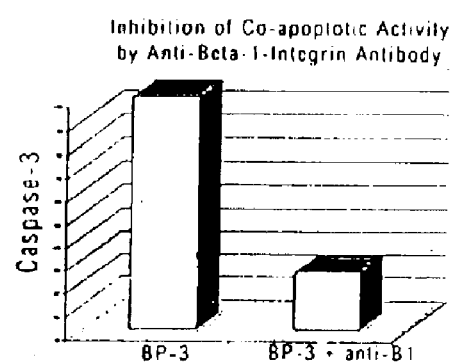
Fig. 8C
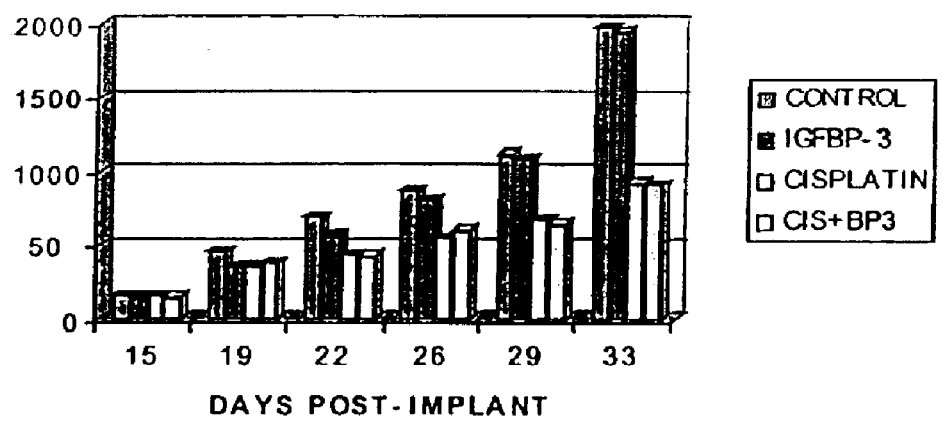
Figs. 8A-8C

CONTROL     anti-alpha5-integrin     anti-beta-1-integrin     anti-fibronectin

Figs. 10A-10B
Fig. 10A
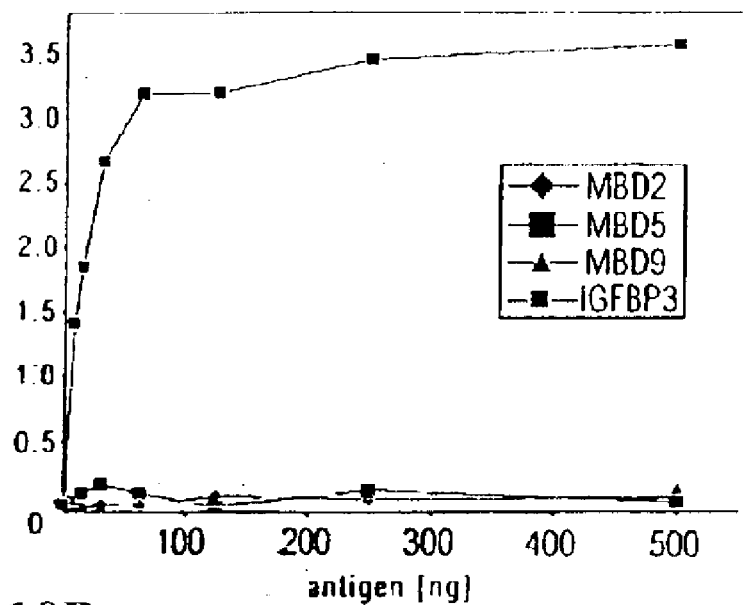
Fig. 10B
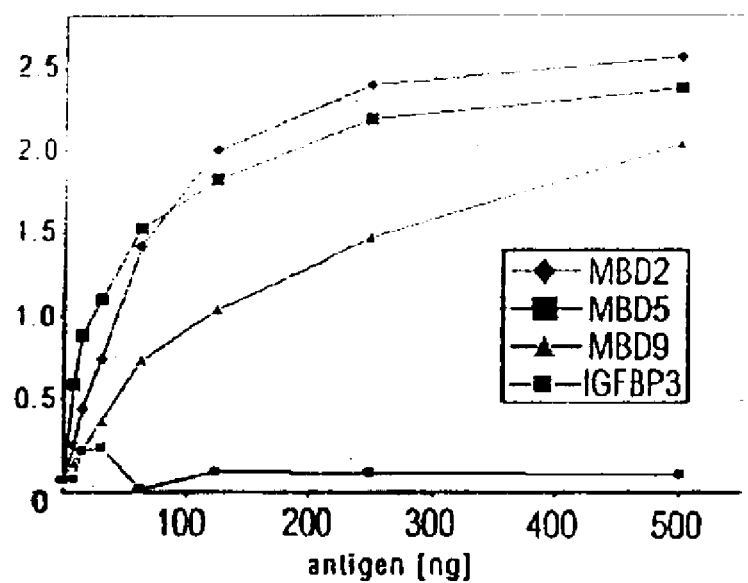

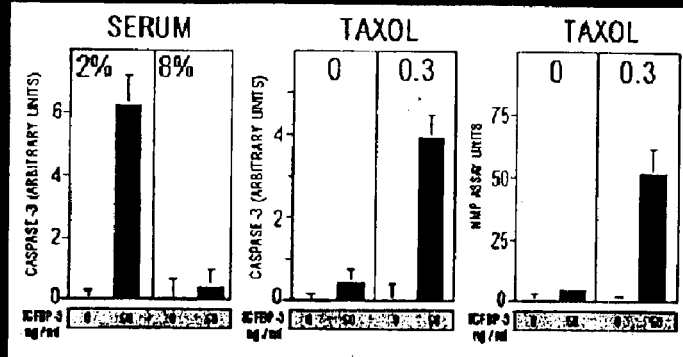
Fig. 11A
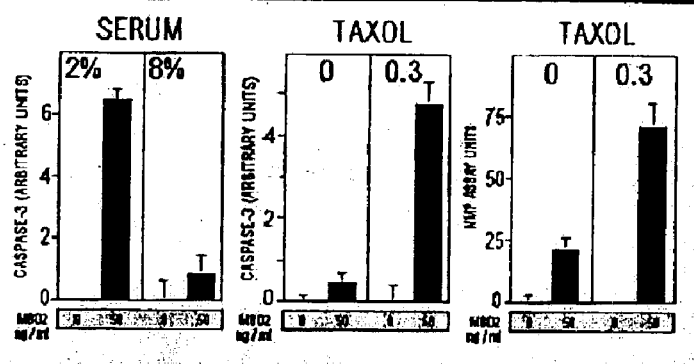
Fig. 11B
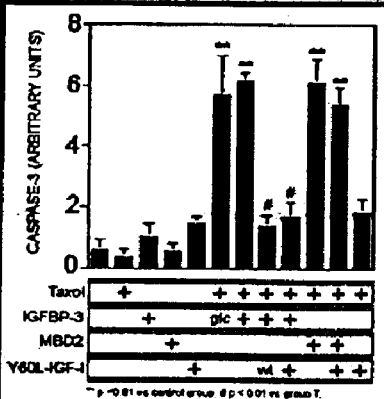
Fig. 11C
Figs. 11A-11C

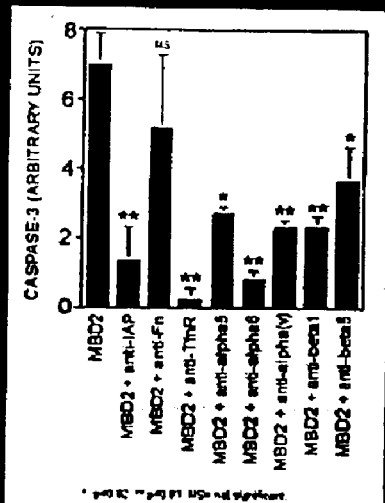
Fig. 12A
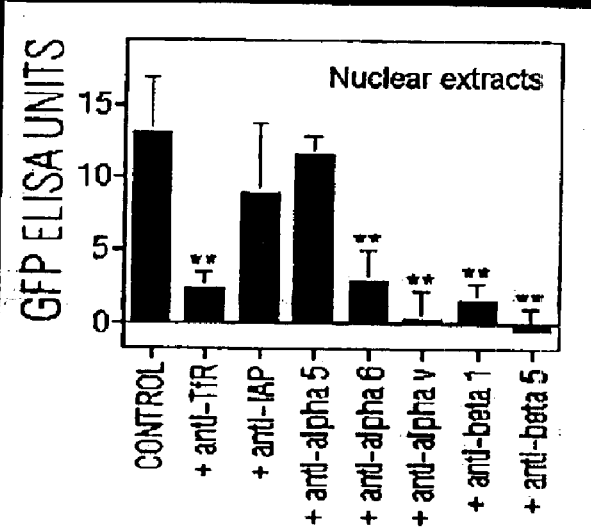
Fig. 12B
Figs. 12A-12B

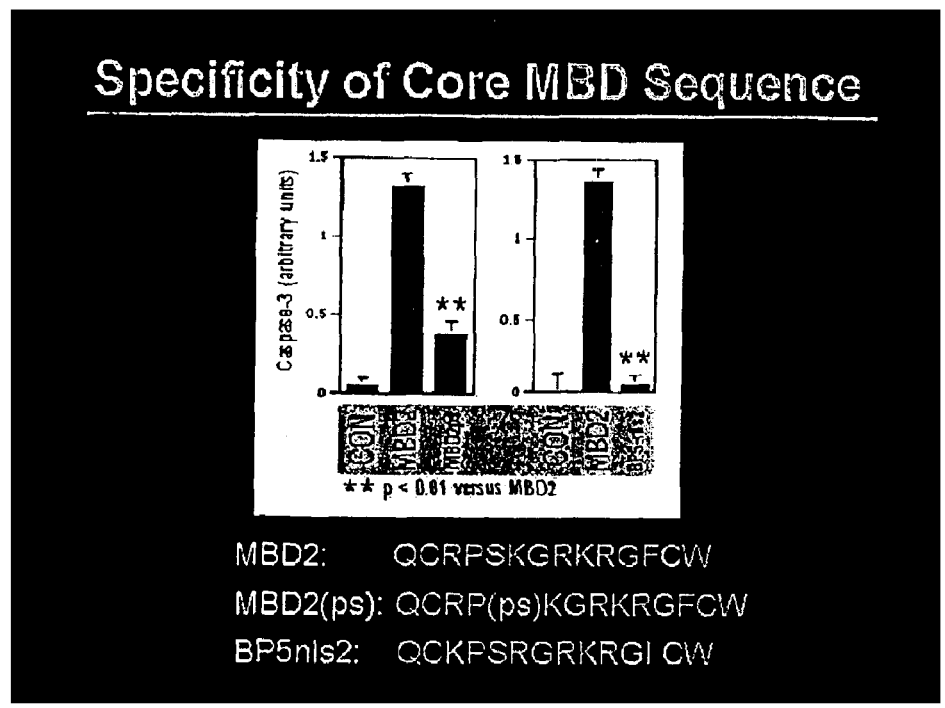
Fig. 13A
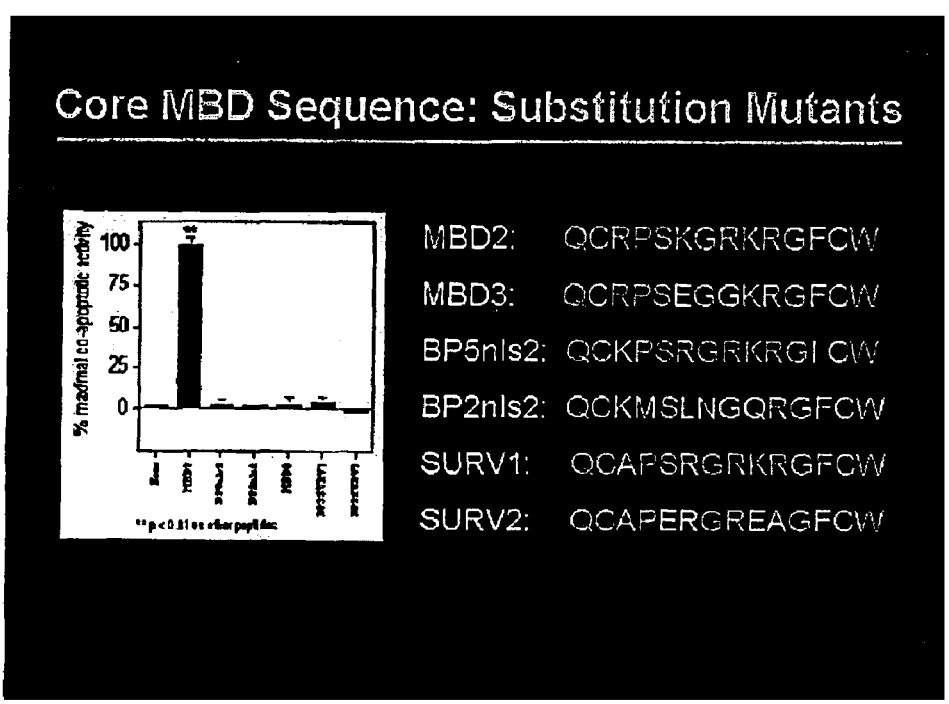
Fig. 13B
Figs. 13A-13B

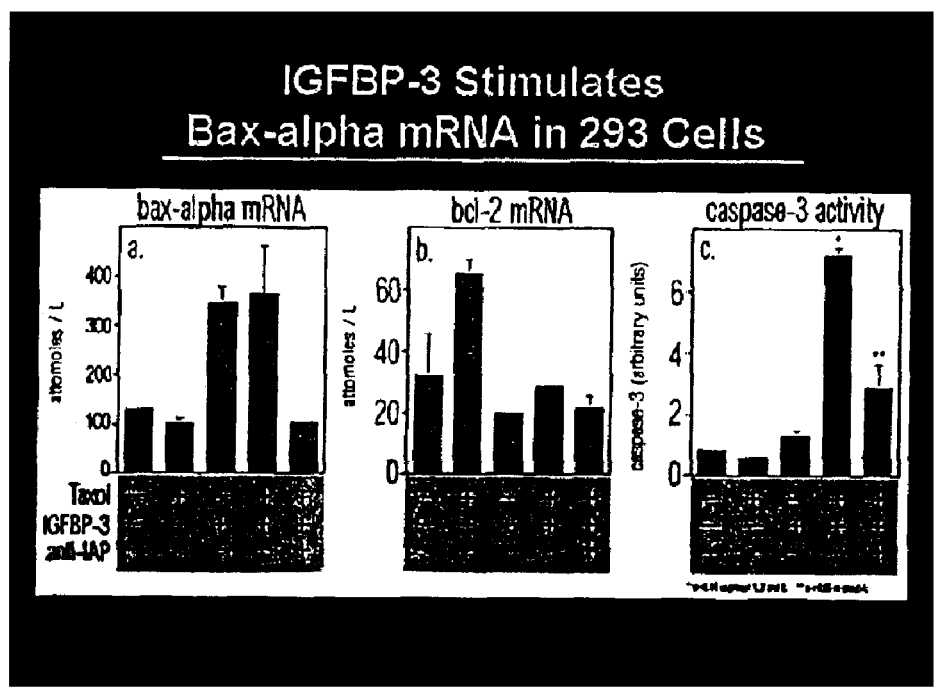
Fig. 14A
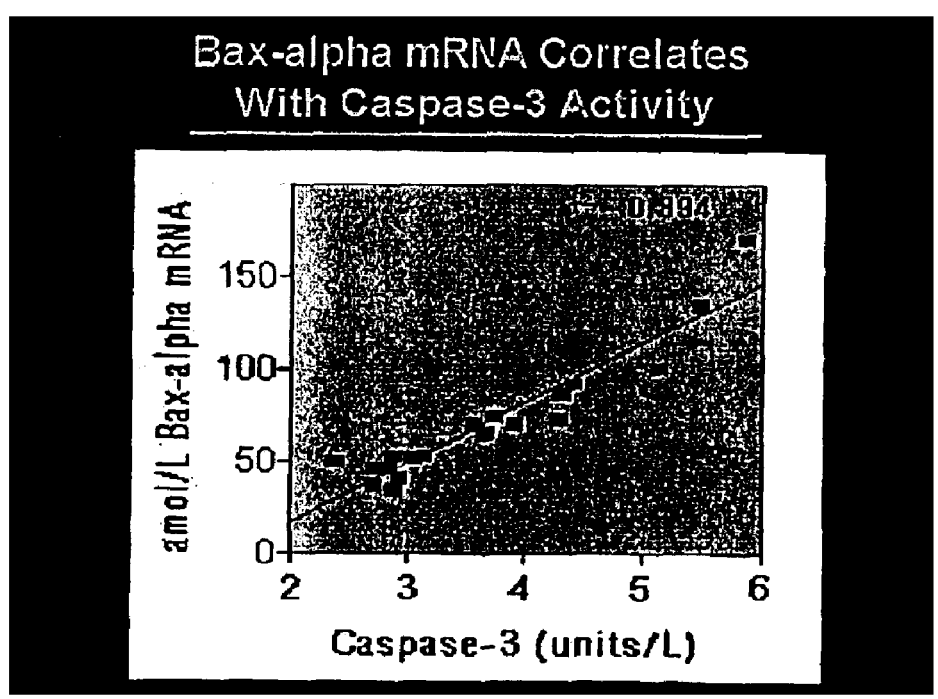
Fig. 14B
Figs. 14A-14B

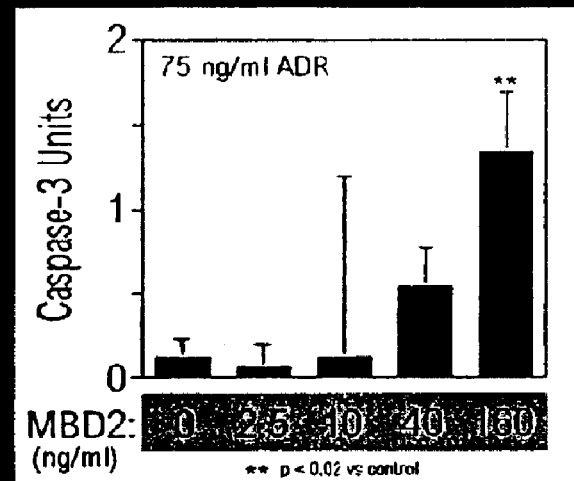
Fig. 16A
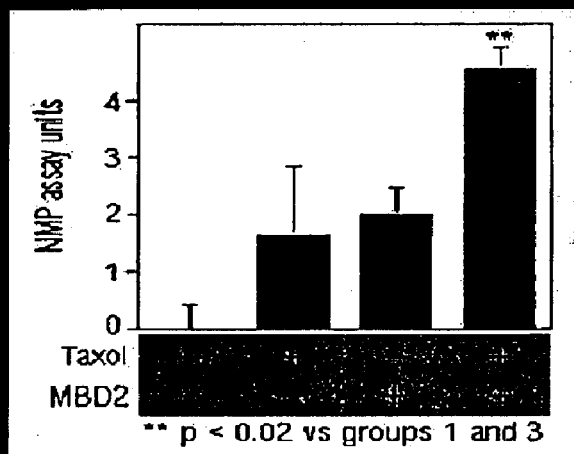
Fig. 16B
Figs. 16A-16B

SEQUENCE LISTING

```
<160> NUMBER OF SEQ ID NOS: 39

<210> SEQ ID NO 1
<211> LENGTH: 23
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(23)

<400> SEQUENCE: 1

Asp Lys Lys Gly Phe Tyr Lys Lys Lys Gln Cys Arg Pro Ser Lys Gly
 1               5                  10                  15

Arg Lys Arg Gly Phe Cys Trp
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(20)
<220> FEATURE:
<221> NAME/KEY: METAL
<222> LOCATION: (8)...(19)

<400> SEQUENCE: 2

Gly Phe Tyr Lys Lys Lys Gln Cys Arg Pro Ser Lys Gly Arg Lys Arg
 1               5                  10                  15

Gly Phe Cys Trp
            20

<210> SEQ ID NO 3
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(14)
<220> FEATURE:
<221> NAME/KEY: METAL
<222> LOCATION: (2)...(13)
```

```
<400> SEQUENCE: 3

Gln Cys Arg Pro Ser Lys Gly Arg Lys Arg Gly Phe Cys Trp
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(12)
<220> FEATURE:
<221> NAME/KEY: METAL
<222> LOCATION: (1)...(12)
<223> OTHER INFORMATION: Selectively binds zinc and nickel

<400> SEQUENCE: 4

Cys Arg Pro Ser Lys Gly Arg Lys Arg Gly Phe Cys
1               5                   10

<210> SEQ ID NO 5
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(19)

<400> SEQUENCE: 5

Ser Tyr Gly Arg Lys Lys Arg Arg Gln Arg Arg Arg Ala His Gln Asn
1               5                   10                  15

Ser Gln Thr

<210> SEQ ID NO 6
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(19)

<400> SEQUENCE: 6

Lys Lys Gly His Ala Lys Asp Ser Gln Arg Tyr Lys Val Asp Tyr Glu
1               5                   10                  15

Ser Gln Ser

<210> SEQ ID NO 7
<211> LENGTH: 22
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(22)
<223> OTHER INFORMATION: Capable of directing cellular internalization
      of unrelated proteins.
<220> FEATURE:
<221> NAME/KEY: METAL
<222> LOCATION: (10)...(21)
<223> OTHER INFORMATION: Selectively binds zinc and nickel
```

-continued

```
<400> SEQUENCE: 7

Lys Lys Gly Phe Tyr Lys Lys Gln Cys Arg Pro Ser Lys Gly Arg
1               5                   10                  15

Lys Arg Gly Phe Cys Trp
            20

<210> SEQ ID NO 8
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(13)
<220> FEATURE:
<221> NAME/KEY: METAL
<222> LOCATION: (2)...(13)
<223> OTHER INFORMATION: Selectively binds zinc and nickel

<400> SEQUENCE: 8

Gln Cys Arg Pro Ser Lys Gly Arg Lys Arg Gly Phe Cys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(13)
<220> FEATURE:
<221> NAME/KEY: METAL
<222> LOCATION: (1)...(12)
<223> OTHER INFORMATION: Selectively binds zinc and nickel

<400> SEQUENCE: 9

Cys Arg Pro Ser Lys Gly Arg Lys Arg Gly Phe Cys Trp
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(8)

<400> SEQUENCE: 10

Lys Lys Gly Phe Tyr Lys Lys Lys
1               5

<210> SEQ ID NO 11
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(26)
<220> FEATURE:
<221> NAME/KEY: METAL
<222> LOCATION: (10)...(21)
<223> OTHER INFORMATION: Selectively binds zinc and nickel
```

-continued

```
<400> SEQUENCE: 11

Lys Lys Gly Phe Tyr Lys Lys Lys Gln Cys Arg Pro Ser Lys Gly Arg
 1               5                  10                  15

Lys Arg Gly Phe Cys Trp Asn Gly Arg Lys
             20                  25

<210> SEQ ID NO 12
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(14)
<220> FEATURE:
<221> NAME/KEY: MUTAGEN
<222> LOCATION: 5
<223> OTHER INFORMATION: Xaa = phosphoserine

<400> SEQUENCE: 12

Gln Cys Arg Pro Xaa Lys Gly Arg Lys Arg Gly Phe Cys Trp
 1               5                  10

<210> SEQ ID NO 13
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(14)

<400> SEQUENCE: 13

Gln Cys Arg Pro Ser Glu Gly Gly Lys Arg Gly Phe Cys Trp
 1               5                  10

<210> SEQ ID NO 14
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(14)

<400> SEQUENCE: 14

Gln Cys Lys Met Ser Leu Asn Gly Gln Arg Gly Glu Cys Trp
 1               5                  10

<210> SEQ ID NO 15
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(14)

<400> SEQUENCE: 15

Gln Cys Lys Pro Ser Arg Gly Arg Lys Arg Gly Ile Cys Trp
 1               5                  10

<210> SEQ ID NO 16
<211> LENGTH: 17
```

```
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(17)
<220> FEATURE:
<221> NAME/KEY: METAL
<222> LOCATION: (2)...(13)
<223> OTHER INFORMATION: Selectively binds zinc and nickel

<400> SEQUENCE: 16

Gln Cys Arg Pro Ser Lys Gly Arg Lys Arg Gly Phe Cys Trp Asn Gly
 1               5                  10                  15

Arg

<210> SEQ ID NO 17
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(28)
<220> FEATURE:
<221> NAME/KEY: METAL
<222> LOCATION: (13)...(24)
<223> OTHER INFORMATION: Selectively binds zinc and nickel

<400> SEQUENCE: 17

Lys Lys Glu Lys Asp Ile Met Lys Lys Thr Ile Gln Cys Arg Pro Ser
 1               5                  10                  15

Lys Gly Arg Lys Arg Gly Phe Cys Trp Asn Gly Arg
            20                  25

<210> SEQ ID NO 18
<211> LENGTH: 264
<212> TYPE: PRT
<213> ORGANISM: Homo sapiens
<220> FEATURE:
<221> NAME/KEY: VARIANT
<222> LOCATION: (1)...(264)
<223> OTHER INFORMATION: Ala5 allelic variant of IGFBP-3
<220> FEATURE:
<221> NAME/KEY: METAL
<222> LOCATION: (224)...(235)
<223> OTHER INFORMATION: Selectively binds zinc and nickel

<400> SEQUENCE: 18

Gly Ala Ser Ser Ala Gly Leu Gly Pro Val Val Arg Cys Glu Pro Cys
 1               5                  10                  15

Asp Ala Arg Ala Leu Ala Gln Cys Ala Pro Pro Ala Val Cys Ala
            20                  25                  30

Glu Leu Val Arg Glu Pro Gly Cys Gly Cys Cys Leu Thr Cys Ala Leu
         35                  40                  45

Ser Glu Gly Gln Pro Cys Gly Ile Tyr Thr Glu Arg Cys Gly Ser Gly
     50                  55                  60

Leu Arg Cys Gln Pro Ser Pro Asp Glu Ala Arg Pro Leu Gln Ala Leu
65                  70                  75                  80

Leu Asp Gly Arg Gly Leu Cys Val Asn Ala Ser Ala Val Ser Arg Leu
                85                  90                  95

Arg Ala Tyr Leu Leu Pro Ala Pro Pro Ala Pro Gly Asn Ala Ser Glu
            100                 105                 110
```

-continued

```
Ser Glu Glu Asp Arg Ser Ala Gly Ser Val Glu Ser Pro Ser Val Ser
            115                 120                 125

Ser Thr His Arg Val Ser Asp Pro Lys Phe His Pro Leu His Ser Lys
        130                 135                 140

Ile Ile Ile Ile Lys Lys Gly His Ala Lys Asp Ser Gln Arg Tyr Lys
145                 150                 155                 160

Val Asp Tyr Glu Ser Gln Ser Thr Asp Thr Gln Asn Phe Ser Ser Glu
                165                 170                 175

Ser Lys Arg Glu Thr Glu Tyr Gly Pro Cys Arg Arg Glu Met Glu Asp
            180                 185                 190

Thr Leu Asn His Leu Lys Phe Leu Asn Val Leu Ser Pro Arg Gly Val
        195                 200                 205

His Ile Pro Asn Cys Asp Lys Lys Gly Phe Tyr Lys Lys Lys Gln Cys
    210                 215                 220

Arg Pro Ser Lys Gly Arg Lys Arg Gly Phe Cys Trp Cys Val Asp Lys
225                 230                 235                 240

Tyr Gly Gln Pro Leu Pro Gly Tyr Thr Thr Lys Gly Lys Glu Asp Val
                245                 250                 255

His Cys Tyr Ser Met Gln Ser Lys
            260

<210> SEQ ID NO 19
<211> LENGTH: 264
<212> TYPE: PRT
<213> ORGANISM: Homo sapiens
<220> FEATURE:
<221> NAME/KEY: VARIANT
<222> LOCATION: (1)...(264)
<223> OTHER INFORMATION: Ala5 allelic variant of IGFBP-3
<220> FEATURE:
<221> NAME/KEY: METAL
<222> LOCATION: (224)...(235)
<223> OTHER INFORMATION: Selectively binds zinc and nickel
<220> FEATURE:
<221> NAME/KEY: MUTAGEN
<222> LOCATION: 109
<223> OTHER INFORMATION: Single amino acid change from Asparagine to
      Aspartic Acid

<400> SEQUENCE: 19

Gly Ala Ser Ser Ala Gly Leu Gly Pro Val Val Arg Cys Glu Pro Cys
1               5                   10                  15

Asp Ala Arg Ala Leu Ala Gln Cys Ala Pro Pro Ala Val Cys Ala
            20                  25                  30

Glu Leu Val Arg Glu Pro Gly Cys Gly Cys Cys Leu Thr Cys Ala Leu
        35                  40                  45

Ser Glu Gly Gln Pro Cys Gly Ile Tyr Thr Glu Arg Cys Gly Ser Gly
    50                  55                  60

Leu Arg Cys Gln Pro Ser Pro Asp Glu Ala Arg Pro Leu Gln Ala Leu
65                  70                  75                  80

Leu Asp Gly Arg Gly Leu Cys Val Asn Ala Ser Ala Val Ser Arg Leu
                85                  90                  95

Arg Ala Tyr Leu Leu Pro Ala Pro Pro Ala Pro Gly Asp Ala Ser Glu
            100                 105                 110

Ser Glu Glu Asp Arg Ser Ala Gly Ser Val Glu Ser Pro Ser Val Ser
        115                 120                 125

Ser Thr His Arg Val Ser Asp Pro Lys Phe His Pro Leu His Ser Lys
    130                 135                 140

Ile Ile Ile Ile Lys Lys Gly His Ala Lys Asp Ser Gln Arg Tyr Lys
```

```
                145                 150                 155                 160
Val Asp Tyr Glu Ser Gln Ser Thr Asp Thr Gln Asn Phe Ser Ser Glu
                    165                 170                 175

Ser Lys Arg Glu Thr Glu Tyr Gly Pro Cys Arg Arg Glu Met Glu Asp
            180                 185                 190

Thr Leu Asn His Leu Lys Phe Leu Asn Val Leu Ser Pro Arg Gly Val
        195                 200                 205

His Ile Pro Asn Cys Asp Lys Lys Gly Phe Tyr Lys Lys Gln Cys
    210                 215                 220

Arg Pro Ser Lys Gly Arg Lys Arg Gly Phe Cys Trp Cys Val Asp Lys
225                 230                 235                 240

Tyr Gly Gln Pro Leu Pro Gly Tyr Thr Thr Lys Gly Lys Glu Asp Val
                245                 250                 255

His Cys Tyr Ser Met Gln Ser Lys
            260
```

<210> SEQ ID NO 20
<211> LENGTH: 19
<212> TYPE: PRT
<213> ORGANISM: Homo sapiens

<400> SEQUENCE: 20

```
Arg Pro Lys Cys Asp Glu Asn Gly Asn Tyr Leu Pro Leu Gln Cys Tyr
1               5                   10                  15

Gly Ser Ile
```

<210> SEQ ID NO 21
<211> LENGTH: 24
<212> TYPE: PRT
<213> ORGANISM: Homo sapiens

<400> SEQUENCE: 21

```
Gly Tyr Cys Trp Cys Val Phe Pro Asn Gly Thr Glu Val Pro Asn Thr
1               5                   10                  15

Arg Ser Arg Gly His His Asn Cys
            20
```

<210> SEQ ID NO 22
<211> LENGTH: 49
<212> TYPE: PRT
<213> ORGANISM: Homo sapiens
<220> FEATURE:
<221> NAME/KEY: METAL
<222> LOCATION: (15)...(26)
<223> OTHER INFORMATION: Selectively binds zinc and nickel

<400> SEQUENCE: 22

```
Ile Pro Asn Cys Asp Lys Lys Gly Phe Tyr Lys Lys Gln Cys Arg
1               5                   10                  15

Pro Ser Lys Gly Arg Lys Arg Gly Phe Cys Trp Cys Val Asp Lys Tyr
            20                  25                  30

Gly Gln Pro Leu Pro Gly Tyr Thr Thr Lys Gly Lys Glu Asp Val His
        35                  40                  45

Cys
```

<210> SEQ ID NO 23
<211> LENGTH: 19
<212> TYPE: PRT
<213> ORGANISM: Homo sapiens

```
<400> SEQUENCE: 23

Ile Pro Gln Cys Asp Glu Gln Gly Asn Phe Leu Pro Leu Gln Cys His
 1               5                  10                  15

Gly Ser Thr

<210> SEQ ID NO 24
<211> LENGTH: 27
<212> TYPE: PRT
<213> ORGANISM: Homo sapiens

<400> SEQUENCE: 24

Gly Phe Cys Trp Cys Val Asp Pro Asp Gly His Glu Val Pro Gly Thr
 1               5                  10                  15

Gln Thr Pro Pro Gly Ser Thr Pro Pro His Cys
            20                  25

<210> SEQ ID NO 25
<211> LENGTH: 19
<212> TYPE: PRT
<213> ORGANISM: Homo sapiens

<400> SEQUENCE: 25

Ile Pro Arg Cys Asn Glu Glu Gly Tyr Tyr Lys Ala Thr Gln Cys His
 1               5                  10                  15

Gly Ser Thr

<210> SEQ ID NO 26
<211> LENGTH: 24
<212> TYPE: PRT
<213> ORGANISM: Homo sapiens

<400> SEQUENCE: 26

Gly Gln Cys Trp Cys Val Asp Lys Tyr Gly Asn Glu Leu Ala Gly Ser
 1               5                  10                  15

Arg Lys Gln Gly Ala Val Ser Cys
            20

<210> SEQ ID NO 27
<211> LENGTH: 19
<212> TYPE: PRT
<213> ORGANISM: Homo sapiens

<400> SEQUENCE: 27

Ile Pro Glu Cys Ala His Gly Gly Leu Tyr Lys Pro Val Gln Cys His
 1               5                  10                  15

Pro Ser Thr

<210> SEQ ID NO 28
<211> LENGTH: 26
<212> TYPE: PRT
<213> ORGANISM: Homo sapiens

<400> SEQUENCE: 28

Gly Tyr Cys Trp Cys Val Leu Val Asp Thr Gly Arg Pro Ile Pro Gly
 1               5                  10                  15

Thr Ser Thr Arg Tyr Glu Gln Pro Lys Cys
            20                  25

<210> SEQ ID NO 29
<211> LENGTH: 19
<212> TYPE: PRT
```

-continued

<213> ORGANISM: Rana catesbiana

<400> SEQUENCE: 29

Ile Pro Gln Cys Asp Glu Lys Gly Asn Tyr Gln Pro Gln Gln Cys His
1               5                   10                  15

Gly Ser Thr

<210> SEQ ID NO 30
<211> LENGTH: 27
<212> TYPE: PRT
<213> ORGANISM: Rana catesbiana

<400> SEQUENCE: 30

Gly His Cys Trp Cys Val Asn Ala Met Gly Glu Lys Ile Ser Gly Thr
1               5                   10                  15

Asn Thr Pro Pro Gly Gln Thr Arg Ala Thr Cys
            20                  25

<210> SEQ ID NO 31
<211> LENGTH: 19
<212> TYPE: PRT
<213> ORGANISM: Salvelinus fontinalis

<400> SEQUENCE: 31

Ile Pro Thr Cys Asp Ala Ala Gly Gln Tyr Thr Pro Lys Gln Cys Trp
1               5                   10                  15

Gly Ser Ala

<210> SEQ ID NO 32
<211> LENGTH: 27
<212> TYPE: PRT
<213> ORGANISM: Salvelinus fontinalis

<400> SEQUENCE: 32

Gly Tyr Cys Trp Cys Val Thr Ser Thr Gly Gln Lys Ile Gln Gly Thr
1               5                   10                  15

Glu Thr Pro Pro Gly Thr Ala Pro Ile Asn Cys
            20                  25

<210> SEQ ID NO 33
<211> LENGTH: 19
<212> TYPE: PRT
<213> ORGANISM: Oncorhynchus keta

<400> SEQUENCE: 33

Ile Pro Thr Cys Asp Tyr Asn Gly Gln Tyr Thr Pro Glu Gln Cys Trp
1               5                   10                  15

Gly Ser Thr

<210> SEQ ID NO 34
<211> LENGTH: 26
<212> TYPE: PRT
<213> ORGANISM: Oncorhynchus keta

<400> SEQUENCE: 34

Gly Tyr Cys Trp Cys Val Asn Ser Ser Gly Gln Lys Leu Pro Gly Thr
1               5                   10                  15

Asp Thr Pro Pro Gly Ser Ala Ser Asn Cys
            20                  25

<210> SEQ ID NO 35

```
<211> LENGTH: 19
<212> TYPE: PRT
<213> ORGANISM: Homo sapiens

<400> SEQUENCE: 35

Ile Pro Glu Cys Asn Asp Asp Gly Thr Tyr Ser Gln Val Gln Cys His
 1               5                  10                  15

Ser Tyr Thr

<210> SEQ ID NO 36
<211> LENGTH: 25
<212> TYPE: PRT
<213> ORGANISM: Homo sapiens

<400> SEQUENCE: 36

Gly Tyr Cys Trp Cys Val Thr Pro Asn Gly Arg Pro Ile Ser Gly Thr
 1               5                  10                  15

Ala Val Ala His Lys Thr Pro Arg Cys
            20                  25

<210> SEQ ID NO 37
<211> LENGTH: 20
<212> TYPE: PRT
<213> ORGANISM: Artificial Sequence
<220> FEATURE:
<223> OTHER INFORMATION: Synthetic Construct

<400> SEQUENCE: 37

Gln Cys Arg Pro Ser Lys Gly Arg Lys Arg Gly Phe Cys Trp Ala Val
 1               5                  10                  15

Asp Lys Tyr Gly
            20

<210> SEQ ID NO 38
<211> LENGTH: 28
<212> TYPE: PRT
<213> ORGANISM: Artificial Sequence
<220> FEATURE:
<223> OTHER INFORMATION: Synthetic Construct

<400> SEQUENCE: 38

Lys Lys Gly Phe Tyr Lys Lys Gln Cys Arg Pro Ser Lys Gly Arg
 1               5                  10                  15

Lys Arg Gly Phe Cys Trp Ala Val Asp Lys Tyr Gly
            20                  25

<210> SEQ ID NO 39
<211> LENGTH: 25
<212> TYPE: PRT
<213> ORGANISM: Artificial Sequence
<220> FEATURE:
<223> OTHER INFORMATION: Synthetic Construct

<400> SEQUENCE: 39

Lys Lys Gly Phe Tyr Lys Lys Gln Cys Arg Pro Ser Lys Gly Arg
 1               5                  10                  15

Lys Arg Gly Phe Cys Trp Asn Gly Arg
            20                  25
```

IGF-BINDING PROTEIN-DERIVED PEPTIDE OR SMALL MOLECULE

CROSS-REFERENCE TO RELATED APPLICATIONS

This application is a continuation-in-part of U.S. patent application Ser. No. 10/264,672, filed Oct. 4, 2002, which is a continuation-in-part of U.S. patent application Ser. No. 10/215,759, filed Aug. 9, 2002, which claims priority under 35 U.S.C. § 119(e) to U.S. Provisional Patent Application Ser. No. 60/323,267, filed Sep. 18, 2001, both of which are incorporated by reference in their entirety.

TECHNICAL FIELD

The invention relates to the compositions and methods of use of peptides or small molecules in the treatment of disease, as well as in high-throughput screening and other discovery and research applications, particularly to the use of metal-binding peptides derived from sequences present in the CD74-homology domain of insulin-like growth factor binding protein-3 (IGFBP-3).

BACKGROUND ART

Growth factors are polypeptides which stimulate a wide variety of biological responses (e.g. DNA synthesis, cell division, expression of specific genes, etc.) in a defined population of target cells. A variety of growth factors have been identified, including the transforming growth factor beta family (TGF-βs), epidermal growth factor and transforming growth factor alpha (the TGF-αs), the platelet-derived growth factors (PDGFs), the fibroblast growth factor family (FGFs) and the insulin-like growth factor family (IGFs), which includes IGF-I and IGF-II. Many growth factors have been implicated in the pathogenesis of cancer.

IGF-I and IGF-II (the "IGFs") are related in amino acid sequence and structure, with each polypeptide having a molecular weight of approximately 7.5 kilodaltons (kDa). IGF-I mediates the major effects of growth hormone, and is thus the primary mediator of growth after birth. IGF-I has also been implicated in the actions of various other growth factors, since the treatment of cells with such growth factors leads to increased production of IGF-I. In contrast, IGF-II is believed to have a major role in fetal growth. Both IGF-I and IGF-II have insulin-like activities (hence their names), and are mitogenic (stimulate cell division).

IGF-I has been found to stimulate the growth of cells from a number of different types of cancer (Butler et al., 1998 *Cancer Res.* 58(14):3021–3027; Favoni R E, et al., 1998, *Br. J. Cancer* 77(12): 2138–2147). IGF-I has additionally been found to exert anti-apoptotic effects on a number of different cell types, including tumor cells (Giuliano M, et al., 1998 *Invest Ophthalmol. Vis. Sci.* 39(8): 1300–1311; Zawada W M, et al., 1998, *Brain Res.* 786(1–2): 96–103; Kelley K W, et al., 1998, *Ann. N. Y. Acad. Sci.* 840: 518–524; Toms S A, et al., 1998, *J. Neurosurg.* 88(5): 884–889; Xu F, et al., 1997, *Br. J. Haematol.* 97(2): 429–440). Prospective studies have implicated IGF-I as a risk factor for cancers of the prostate, breast, and colon, while IGFBP-3, the major circulatory binding protein for IGFs, appears to have a protective effect (10–12, 28, 29). A variety of other observations further support the idea that the relative balance of IGFBP-3 to other IGF-binding proteins (notably IGFBP-2) is somehow instrumental in the control of tumor cell growth, both in vitro and in vivo (7–9). Recent evidence also suggests that IGFBP-3 may play a central role in the growth (13–17) and apoptosis (14) of tumor cells in an IGF-independent manner.

Approximately half of the 1.3 million patients diagnosed with cancer each year in the U.S. have (or will be at risk for) systemic disease. Chemotherapy is the most common therapeutic approach for these patients (34). Most chemotherapeutic agents are effective primarily against dividing cells, and myelosuppression is often the dose-limiting toxicity. Chemical agents fall into several categories and have different mechanisms of action but, at effective doses, most have side-effects which seriously impact the patient's quality of life. doxorubicin (ADRIAMYCIN®), irinotecan (CPT-11), paclitaxel (TAXOL®), cisplatin, tamoxifen, methotrexate and 5-fluorouracil are popular agents used to treat a variety of cancers, sometimes in combination. In addition to myelosuppression, gastrointestinal effects, mucositis, alopecia, and (in the case of doxorubicin) cardiac toxicities are also observed with these agents (34). Clearly, it would be of interest to find ways to make tumor cells selectively sensitive to these chemical agents.

Almost all IGF circulates in a non-covalently associated complex of IGF-I, insulin-like growth factor binding protein 3 (IGFBP-3) and a larger protein subunit termed the acid labile subunit (ALS), such that very little free IGF-I is detectable. The ternary complex is composed of equimolar amounts of each of the three components. ALS has no direct IGF-binding activity and appears to bind only to the IGF/IGFBP-3 complex (Baxter et al., *J. Biol. Chem.* 264(20):11843–11848, 1989), although some reports suggest that IGFBP-3 can bind to rat ALS in the absence of IGF (Lee et al., *Endocrinology* 136:4982–4989, 1995). The ternary complex of IGF/IGFBP-3/ALS has a molecular weight of approximately 150 kDa and has a substantially increased half-life in circulation when compared to binary IGF/IGFBP-3 complex or IGF alone (Adams et al., *Prog. Growth Factor Res.* 6(2–4):347–356; presented October 1995, published 1996). This ternary complex is thought to act "as a reservoir and a buffer for IGF-I and IGF-II preventing rapid changes in the concentration of free IGF" (Blum et al. (1991), "Plasma IGFBP-3 Levels as Clinical Indicators" in MODERN CONCEPTS OF INSULIN-LIKE GROWTH FACTORS, pp. 381–393, E. M. Spencer, ed., Elsevier, N.Y.). While there is essentially no excess (unbound) IGFBP-3 in circulation, a substantial excess of free ALS does exist (Baxter, *J. Clin. Endocrinol. Metab.* 67:265–272, 1988).

How IGFBP-3 mediates its cellular effects is not well understood, although there is indirect evidence to suggest that it mediates some of the effects of p53, a well-characterized tumor suppressor (Ferry et al., (1999) *Horm Metab Res* 31(2–3):192–202). IGFBP-3 is mobilized to the nucleus of rapidly growing cells (Schedlich, et al., (1998) *J. Biol. Chem.* 273(29):18347–52; Jaques, et al., (1997) *Endocrinology* 138(4):1767–70). A useful step toward defining the functional interactions of IGFBP-3 would be to identify protein domains involved in the ability of IGFBP-3 to specifically bind a surprisingly large array of intracellular and extracellular targets. Known targets include: IGF-I, IGF-II, insulin (under some conditions), acid-labile subunit (ALS), plasminogen, fibrinogen, transferrin, lactoferrin, collagen Type Ia, prekallikrein, RXR-alpha, viral oncoproteins, heparin, specific proteases, cellular receptors, a number of intracellular targets identified in two-hybrid screens, and components of the nuclear localization transport machinery (Mohseni-Zadeh and Binoux (1997) *Endocrinology* 138(12):5645–8; Collett-Solberg, et al. (1998) *J. Clin. Endocrinol Metab.* 83(8):2843–8; Rajah, et al. (1995) *Prog. Growth Factor Res.* 6(2–4):273–84; Fowlkes and Serra (1996) *J. Biol. Chem.* 271:14676–14679; Campbell, et al. (1999) *J. Biol Chem.* 274(42):30215–21; Durham, et al. (1999) *Horm*

*Metab Res* 31(2–3):216–25; Campbell, et al. (1998) *Am J Physiol.* 275(2Pt 1):E321–31).

IGFBP-3 has three major domains, roughly corresponding to exons 1, 2 and 3+4 of the IGFBP-3 gene, respectively. The C-terminal domain of IGFBP-3 (Domain 3), which contains sequences homologous to a motif found in CD74 (invariant chain) and a number of other proteins, appears to be involved in IGFBP-3's ability to interact with serum, extracellular matrix, and cell surface components. Peptides made to sequences in this region have previously been shown to interfere with the binding of IGFBP-3 to a number of its known ligands, including RXR-alpha, transferrin, ALS, plasminogen, fibrinogen and pre-kallikrein (Liu, et al, *J. Biol. Chem.* 275: 33607–13, 2000; Weinzimer, et al, *J. Clin. Endocrinol. Metab.* 86: 1806–13, 2001; Campbell, et al, *Am.J.Physiol.* 275: E321–31, 1998; Campbell, et al, *J. Biol.Chem.* 274: 30215–21, 1999; Firth, et al, *J. Biol. Chem.* 273: 2631–8, 1998). However, to date, IGFBP-3-derived peptides have not been shown to be sufficient for selective, high-affinity binding to any of these ligands.

This region of the molecule has also been implicated in nuclear translocation, but the mechanism by which IGFBP-3 is internalized into target cells is not well understood (Schledlich, et al, *J.Biol.Chem.* 273: 18347–52, 1998; Jaques, et al, *Endocrinology* 138: 1767–70, 1997). A recently described mutant in which Domain 3 residues 228–232 of IGFBP-3 have been substituted with the corresponding residues from IGFBP-1 (a closely related protein) shows impaired binding to ALS, RXR-alpha, and plasminogen (Campbell, et al. (1998) *Am. J. Physiol.* 275(2 Pt 1):E321–31; Firth, et al. (1998) *J. Biol. Chem.* 273:2631–2638). Specific proteolysis of IGFBP-3 under certain physiological conditions such as pregnancy and critical illness can lead to altered binding and release of its IGF ligand. The binary complex of IGFBP-3 with IGF-I or IGF-II (both growth factors bind IGFBP-3, with similar affinities) can extravasate across endothelial junctions to the intercellular milieu where IGFBP-3 can interact specifically with glycosaminoglycans, specific proteases, and cell-surface proteins. Research reports have referred to the presence of a C-terminal domain in IGFBP-3 that can inhibit IGFBP-4 proteolysis (Fowlkes, et al, *J.Biol.Chem.* 270: 27481–8, 1995; Fowlkes, et al, *Endocrinology* 138: 2280–5, 1997). However, the exact location of this putative protease inhibitor domain has not yet been described. IGFBP-4 proteolysis is a key event in a number of biological processes, including pregnancy, post-angioplasty smooth muscle cell growth, bone formation, and ovarian follicular dominance (Byun, et al, *J.Clin.Endocrinol.Metab.* 86: 847–54, 2001; Bayes_Genis, et al, *Arterioscler. Thromb. Vasc. Biol.* 21: 335–41, 2001; Miyakoshi et al, *Endocrinol.* 142: 2641–8, 2001; Conover, et al, *Endocrinol.* 142: 2155, 2001; Rivera, et al, *Biol.Reprod.* 65: 102–11, 2001).

It should be noted that, while IGFBP-3 is the most abundant of the IGF binding proteins ("IGFBPs"), at least five other distinct IGFBPs have been identified in various tissues and body fluids. Although these proteins bind IGFs, they originate from separate genes and have distinct amino acid sequences. Unlike IGFBP-3, other circulating IGFBPs are not saturated with IGFs. IGFBP-3 and IGFBP-5 are the only known IGFBPs which can form the 150 kDa ternary complex with IGF and ALS. The IGF-binding domain of IGFBP-3 is thought to be in the N-terminal portion of the protein, as N-terminal fragments of the protein isolated from serum retain IGF binding activity. However, some of the other IGFBPs have also been suggested for use in combination with IGF-I as therapeutics.

In addition to its role as the major carrier protein for IGF in serum, IGFBP-3 has been recently shown to have a number of different activities. IGFBP-3 can bind to an as-yet unidentified molecule on the cell surface, where it can inhibit the activity of exogenously-added IGF-I (Karas et al., 1997, *J. Biol. Chem.* 272(26):16514–16520). Although the binding of IGFBP-3 to cell surfaces can be inhibited by heparin, the unidentified cell surface binding molecule is unlikely to be a heparin-like cell surface glycosaminoglycan, because enzymatic removal of heparin glycosaminoglycans has no effect on IGFBP-3 cell surface binding (Yang et al., 1996, *Endocrinology* 137(10):4363–4371). It is not clear if the cell surface binding molecule is the same or different than the IGFBP-3 receptor that was identified by Leal et al. (1997, *J. Biol. Chem.* 272(33):20572–20576), which is identical to the type V transforming growth factor-beta (TGF-β) receptor.

IGFBP-3, when used alone in in vitro assays, has also been reported to promote apoptosis. Interestingly, IGFBP-3 has been shown to promote apoptosis in cells with and without functional type 1 IGF receptors (Nickerson et al., 1997, *Biochem. Biophys. Res. Comm.* 237(3):690–693; Rajah et al., 1997, *J. Biol. Chem.* 272(18):12181–12188). However, there are conflicting reports as to whether apoptosis is induced by full length IGFBP-3 or a proteolytic fragment of IGFBP-3 (Rajah et al., ibid; Zadeh et al., 1997, *Endocrinology* 138(7):3069–3072). More recently, a wealth of unpublished data gathered in a number of laboratories fails to support some of the claims made in the above publications. In in vivo models tested to date, infused IGFBP-3 protein alone has showed mixed results in limiting tumor growth.

U.S. Pat. No. 5,681,818 claims the administration of IGFBP-3 for controlling the growth of somatomedin dependent tumors in the treatment of cancer. U.S. Pat. No. 5,840,673 also describes the indirect intracellular modulation of IGFBP-3 levels as a method for controlling tumor growth. U.S. Pat. No. 6,015,786 discloses the use of IGFBP-3 complexed with mutant IGF for the treatment of IGF-dependent tumors. However, each of these patents discloses a direct in vivo effect of administered IGFBP-3 protein on tumor growth. All of these patents envisages the use of intact IGFBP-3, including its IGF-binding domain. Numerous publications (Williams, et al., *Cancer Res* 60(1):22–7, 2000; Perks, et al., *J Cell Biochem* 75(4):652–64, 1999; Maile et al., *Endocrinology* 140(9):4040–5, 1999; Gill, et al., *J Biol Chem* 272(41):25602–7, 1997) further demonstrate combined effects of IGF binding proteins, radiation and ceramide on cultured cells. In one report (Portera et al, *Growth Hormone & IGF Research* 2000, Supplement A, S49–S50, 2000) IGFBP-3 combined with CPT-11 showed additive effects in a colon cancer model both in vivo and in vitro. All of the above studies were conducted using intact IGFBP-3, a multifunctional molecule capable of carrying IGFs (which are anti-apoptotic) to cells, while also capable of exerting IGF-independent pro-apoptotic effects of its own. Clearly it would be of interest to separate these two activities at the molecular level, but molecules exhibiting a desirable subset of the activities of intact IGFBP-3 have not been described.

IGF-I and IGFBP-3 may be purified from natural sources or produced by recombinant means. For instance, purification of IGF-I from human serum is well known in the art (Rinderknecht et al. (1976) *Proc. Natl. Acad. Sci. USA* 73:2365–2369). Production of IGF-I by recombinant processes is shown in EP 0 128 733, published in December of 1984. IGFBP-3 may be purified from natural sources using a process such as that shown in Baxter et al. (1986, *Biochem. Biophys. Res. Comm.* 139:1256–1261). Alternatively, IGFBP-3 may be synthesized by recombinantly as discussed in Sommer et al., pp. 715–728, MODERN CONCEPTS OF INSULIN-LIKE GROWTH FACTORS (E. M. Spencer, ed., Elsevier, N.Y., 1991). Recombinant IGFBP-3 binds IGF-I in a 1:1 molar ratio.

Topical administration of IGF-I/IGFBP-3 complex to rat and pig wounds is significantly more effective than administration of IGF-I alone (Id.). Subcutaneous administration of IGF-I/IGFBP-3 complex to hypophysectomized, ovariectomized, and normal rats, as well as intravenous administration to cynomolgus monkeys, "substantially prevents the hypoglycemic effects" of IGF-I administered alone (Id.).

The use of IGF/IGFBP-3 complex has been suggested for the treatment of a wide variety of disorders (see, for example, U.S. Pat. Nos. 5,187,151, 5,527,776, 5,407,913, 5,643,867, 5,681,818 and 5,723,441, as well as International Patent Applications Nos. WO 95/03817, WO 95/13823, and WO 96/02565. IGF-I/IGFBP-3 complex is also under development by Insmed Pharmaceuticals, Inc., as a treatment for several indications, including diabetes and recovery from hip fracture surgery.

For practitioners skilled in the art, the complex of IGF-I and IGFBP-3 is generally considered to be a different compound, and to have different biological effects, than IGFBP-3 alone.

While there are a large number of cytotoxic drugs available for the treatment of cancer, these drugs are generally associated with a variety of serious side effects, including alopecia, leukopenia, mucositis. Accordingly, there is a need in the art for cancer therapies that do not induce the serious side effects associated with conventional cytotoxic chemotherapy. One method for achieving this goal is to make target cells (such as tumor cells) selectively sensitive to cytotoxic drugs, thereby permitting the effective use of such drugs at lower doses not associated with serious side effects. A pro-apoptotic peptide derived from IGF-binding protein may be capable of hastening the apoptotic response of tumor cells to chemotherapeutic and other agents (see copending U.S. application titled "Method for Use of IGF-Binding Protein for Selective Sensitization of Target Cells In Vivo" by D. Mascarenhas, filed Sep. 18, 2001).

Lifestyle changes in modern Western societies appear to have triggered an epidemic of diseases believed to be related to longer lifespans, richer diets, modified sleep patterns, increased stress-inducing and sedentary behaviors. The possible involvement of viral co-factors (particularly Epstein-Barr virus and other herpesviruses) has also been suspected. This constellation of diseases include cancer, cardiovascular diseases such, as atherosclerosis, autoimmune diseases such as arthritis, asthma and inflammatory bowel diseases, degenerative diseases such as osteoporosis, proliferative/ inflammatory diseases such as retinopathy, and metabolic diseases such as diabetes (Grimble R F, Curr Opin Clin Nutr Metab Care 5: 551–559, 2002).

A factor common to the increased incidence of most, if not all of these diseases is the altered role of the immune system, in particular chronic inflammatory responses at the cellular level. The intracellular molecular signatures of such responses often include activation of global intracellular and extracellular regulators such as NF-kappa-B, STAT3 (Niu G et al Oncogene 21: 2000–2008, 2002), VEGF and cyclooxygenase-2 (COX-2). NF-kappa-B is a key mediator of the pro-survival induction of HIF in solid tumors (Talks K L et al Am.J.Pathol. 157: 411–421, 2000). COX-2 inhibitors are now being used to treat a variety of autoimmune indications such as arthritis, as well as cancer (Crofford L J, Curr Opin Rheumatol 14:225–30, 2002). The anti-inflammatory agent, rapamycin (sirolimus) has been successfully used to coat stents, with major implications for the treatment of cardiovascular disease (Degertekin M et al, Circulation 106:1610–3, 2002). Circulatory levels of C-reactive protein (CRP), a surrogate marker for chronic inflammation, are now used as major predictors of heart disease risk (Futterman L G and Lemberg L., Am J Crit Care 11: 482–6, 2002; Libby P et al, Circulation 105:1135–43, 2002). And obesity, previously implicated as a risk factor in diabetes and heart disease, appears to provide a causal link to these diseases, as fat cells are known to secrete pro-inflammatory cytokines (Coppack S W, Proc Nutr Soc 60:349–56, 2001).

Another common molecular signature of cells playing key roles in the above pathologies is the display of surface adhesion molecules, especially integrins. Studies have implicated alpha(v) and beta integrins in processes as diverse as metastasis (Felding-Habermann B et al, PNAS 98: 1853–8, 2001), angiogenesis (Eliceiri B P and Cheresh D A, Cancer J 3: S245–9, 2000), atherosclerosis (Nichols T C et al, Circ Res 85:1040–5, 1999), osteoporosis (Pfaff M and Jurdic J J.Cell Sci. 114: 2775–2786, 2001) and autoimmune disease. Clearly, there would be an advantage to the use of systemic agents capable of specifically targeting cells displaying these integrins. The advantage would be particularly great if the same agent could also modulate levels of key global pro-inflammatory regulators such as NF-kappa-B within target cells.

IGFBP-3 and the MBD peptides of the present invention clearly exhibit both of these desirable properties. As shown in the examples section, in a mouse tumor model (mammary 16C), tumors in animals treated with subcutaneous daily injections of IGFBP-3 protein showed increased sensitivity to doxorubicin (adriamycin). Post facto analysis of tumor tissues showed that NF-kappa-B was downregulated 4–5-fold in tumors from animal treated with IGFBP-3 plus adriamycin versus those treated with adriamycin alone. In separate experiments the inventor has shown that IGFBP-3 and MBD peptides are preferentially active upon cells expressing certain surface integrins. In particular, antibodies to alpha(V) and certain beta integrins can prevent nuclear uptake of MBD peptides and subsequent co-apoptotic biochemical events. As such, IGFBP-3 and MBD peptides present unique opportunities as agents for treating the constellation of diseases enumerated above, as well as any other biological process characterized by cellular invasiveness dependent on or stimulated by alpha(v) or beta integrins and/or pro-inflammatory molecules. An example of the latter would be the process of cytotrophoblast implantation during fertilization (Illera M J et al, Biol. Reprod. 62: 1285–1290, 2000).

Other applications for IGFBP-3, IGFBP-derived peptides and related molecules of the invention may be envisaged including modulators or diagnostic reporters of inflammatory and invasive processes in cancer metastasis, tumor stromal activation, autoimmune diseases such as systemic lupus erythrematosis (SLE), multiple sclerosis, diabetes, ankylosing spondulitis, ulcerative colitis, Crohn's and other inflammatory bowel disease, arthritis, asthma and allergy, bone resorptive disease, proliferative disease, wound healing, ophthalmological diseases including retinopathies, fibrotic diseases, reproductive biology, atherosclerosis and other cardiovascular indications; research tools useful in genomics- and proteomics-related applications including high-throughput screening tools in drug discovery and other research programs, reagents and vectors capable of enhancing existing technologies for rapid expression and screening of new genetic sequences, gene therapy, diagnostics and nanotechnology applications; and in stem cell-related applications.

Numerous natural and pathological processes involve an "inflammatory-invasive" or "inflammatory-migratory" condition. Examples include invasive tumors, blastocyst/cytotrophoblast implantation, atherosclerotic plaque build-up, bone turnover, joint swelling in arthritic conditions, relapsing-remitting autoimmune conditions such as multiple sclerosis, SLE and others, proliferative retinal diseases and activation of airway epithelium in asthmatics. A common feature of these biological processes is the activated state of cell types participating in local cross-talk relevant to the disease condition. For example, invasive epithelial tumors generally include (in addition to the tumor cells themselves), activated stromal cells, microvascular epithelial cells and inflammatory immune cells. Interventions targeting any of these cell types might be expected to influence overall disease patterns dramatically. The inventor has unexpectedly found that IGFBP-3 and IGFBP-derived peptides preferentially trigger cell death/apoptosis in such activated cells, compared to the same cell types without activation. A corroborating observation is the dependence of the co-apoptotic effects on alpha-5 and beta-1 integrins, which are known to be preferentially displayed by activated and migrating cells (Boles, et al, 2000, *Am. J.Physiol. Lung Cell Mol. Physiol.* 278: L703–L712; Laukaitis, et al, 2001,. *J.Cell Biol.* 153: 1427–1440) and in bone marrow micrometastases from epithelial tumors (Putz, et al, 1999, *Cancer Res.* 59: 241–248).

It is important to distinguish these effects from those relating to abrogation of IGF-I-dependent proliferative effects. The literature is replete with mention of IGF-I dependent inflammatory processes such as psoriasis. For example, U.S. Pat. No. 5,929,040 teaches the use of inhibitors targeting the IGF-I receptor, thereby reducing skin inflammation. IGFBPs can reduce signaling through this receptor by binding and thereby sequestering IGF-I. However, the IGFBP-derived peptides of this invention do not bind IGF-I and are not believed to exert their effects via the IGF-I receptor.

A distinction should also be made between the present invention and U.S. Pat. No. 5,527,776 which reveals the use of intact IGFBP-3/IGF-I complex to treat subjects with immune deficiencies and anemias. The present invention uses non-IGF-I-binding fragments derived from IGFBP-3 alone, to treat conditions characterized by immune stimulation rather than deficiency.

Consequently, IGFBP-3, IGFBP-derived peptides and related molecules of the invention may be envisaged as modulators or diagnostic reporters of angiogenic, osteoclastogenic, atherogenic, invasive, metastatic, reproductive, arthritic, asthmatic, fibrotic, retinopathic, infective, inflammatory, neurodegenerative, stress-related, cell remodeling- or immortalization-related biological processes.

In particular, IGFBP-3-derived peptides or smaller derivative molecules as disclosed herein may be used as protease inhibitors, metal chelators, anti-proliferative, anti-metastatic or anti-angiogenic molecules. They may also be useful as plasma carrier agents, facilitators of binding to extracellular matrix components, targeting agents, transporters of large or small compounds into cells (cell internalization agents), affinity purification tags, screening tags, transcriptional or DNA-binding agents, cell-labeling agents, regulatory modulators, or as agents exhibiting any combination of the above properties. In particular, such derivative molecules may be derived from the CD74-homology domain sequence at the carboxy-terminus of IGFBP-3, and many of these activities have never been localized to this region of the IGFBP-3 molecule before. Peptides made to sequences in this region have previously been shown to interfere with the binding of IGFBP-3 to a number of its known ligands, including RXR-alpha, transferrin, ALS, plasminogen, fibrinogen and pre-kallikrein (Liu, et al, *J. Biol. Chem.* 275: 33607–13, 2000; Weinzimer, et al, *J. Clin. Endocrinol. Metab.* 86: 1806–13, 2001; Campbell, et al, *Am.J.Physiol.* 275: E321–31, 1998; Campbell, et al, *J. Biol.Chem.* 274: 30215–21, 1999; Firth, et al, *J. Biol. Chem.* 273: 2631–8, 1998). However, to date, IGFBP-3-derived peptides have not been shown to be sufficient for selective, high-affinity binding to any of these ligands.

The IGFBP-3-derived metal-binding domain peptides disclosed herein differ from previously disclosed IGFBP-3-derived molecules in a number of important ways, including their inability to bind IGF-I, their unique antigenicity, and the absence of the IGFBP-3 putative death receptor (P4.33) interaction domain of IGFBP-3 (so-called "mid-region"; amino acids 88–148). The P4.33 putative death receptor is described in International Patent Application No. WO 01/87238 (Genbank Accession Number BC031217; gi:21411477). For example, International Patent Application No. WO 02/34916 teaches the use of point mutants of IGFBP-3 in which the binding to IGF-I is impaired. However, the described molecules contain the mid-region of IGFBP-3 and would be expected to exert biological effects by interacting with the P4.33 putative receptor. International Patent Application No. WO 01/87238 teaches the use of P4.33 modulators for treating disease. The metal-binding peptides of the present invention do not include the P4.33 putative interaction domain (mid-region of IGFBP-3). U.S. Pat. No. 6,417,330 teaches the use of IGFBP-3 variants which are modified to be resistant to hydrolysis. Also disclosed are variant IGFBP-3s where the nuclear localization signal (NLS) in native IGFBP-3 is altered. Additionally, amino-terminally extended IGFBP-3s are disclosed which include a variety of N-terminal extensions. All of these molecules differ from the metal-binding domain peptides of the present invention in two important ways: They bind IGF-I and they contain the mid-region of IGFBP-3, believed to interact with the P4.33 putative death receptor. Some recent publications have described the use of IGFBP-3 peptides to treat cells in culture. The only peptides found to be active on breast cancer cells are derived from the mid-region of IGFBP-3 (McCaig, et al, 2002, *Br. J. Cancer* 86: 1963–1969; Perks, et al, *Bioch. Biophys. Res. Comm.* 294: 988–994, 2002). This region is not present in the sequence of the metal-binding domain peptides of this invention.

Iron metabolism (particularly ferrous iron) offers many possibilities for intervention in disease processes. For example, neoplastic cells express high levels of the transferrin receptor 1 (TfR1) and internalize iron (Fe) from transferrin (Tf) at a very high rate. Antisense ferritin oligonucleotides inhibit growth and induce apoptosis in human breast cancer cells (Yang et al., 2002, *Anticancer Res.* 22(3):1513–24). Artemisinin becomes cytotoxic in the presence of ferrous iron. Since iron influx is high in cancer cells, artemisinin and its analogs selectively kill cancer cells under conditions that increase intracellular iron concentrations (Singh et al., 2001, *Life Sci.* 70(1):49–56). Iron chelators can cause apoptotic effects in cancer cells (Simonart et al., 2002, *Gynecol Oncol.* 85(1):95–102; Green et al., 2001, *Clin. Cancer Res.* 7(11):3574–9). Cancer risk is also known to be associated with body iron stores (Kato et al., 1999, *Int. J. Cancer* 80(5):693–8).

In addition to neoplastic conditions, many other disease states are known to exhibit characteristic imbalances in iron homeostasis: among them are Parkinson's disease (Logroscino et al., 1997, *Neurology* 49(3):714–7), rheumatoid arthritis (Weber et al., 1988, *Ann. Rheum. Dis.* 47(5):404–9), inflammation (Morris et al., 1995, *Int. J. Biochem. Cell. Biol.* 27(2):109–22) and atherosclerosis (Schmitz et al., 2001, *J. Magn. Reson. Imaging* 14(4):355–61), Acute iron poisoning and chronic iron overload are well-known causes of myocardial failure. Although the exact mechanism is not known, excess iron-catalyzed free radical generation is conjectured to play a role in damaging the myocardium and altering cardiac function (Bartfay et al., 1999, *Cardiovasc. Pathol.* 8(6):305–14; Parks et al., 1997, *Toxicology* 117(2–3):141–51). Ferrous iron can damage mitochondrial DNA (Asin et al., 2000, *FEBS Lett.* 480(2–3):161–4). Reperfusion injury, which occurs upon the reintroduction of blood flow to an ischemic organ, is responsible for considerable damage in heart attacks and strokes. A major cause of reperfusion injury is the iron-mediated generation of hydroxyl radical (.OH) (Horwitz et al., 1998, *Proc. Natl. Acad. Sci. USA* 95(9):5263–8).The use of a highly diffusible lipophilic iron chelator secreted by Mycobacterium tuberculosis inhibits proliferation of smooth muscle cells in culture (Rosenthal et al., 2001, *Circulation* 104(18):2222–7) and restenosis in vivo.

Iron particles, in the form of superparamagnetic iron oxide (SPIO) particles (Ferucci, 1991, *Keio J. Med.* 40(4):206–14; Taupitz et al., 1993, *Acta Radiol.* 34(1):10–5; Mack et al., 2002, *Radiology* 222(1):239–44) have been used to enhance contrast in magnetic resonance imaging. More recently, these particles have been combined with alternating magnetic fields to generate local effects on iron-rich cancer cells, a procedure dubbed "magnetic thermal ablation" (Hilger et al., 2002, *Invest. Radiol.* 37(10):580–6; Shinkei et al., 2001, *Jpn. J. Cancer Res.* 92(10):1138–45).

It should be noted that any reference to any patent, patent application, or publication in this Background section is not an admission that such patent, patent application, or publication constitutes prior art to the instant invention.

DISCLOSURE OF THE INVENTION

The inventor has surprisingly found that IGFBP-3 or peptides containing parts of the human IGFBP-3 sequence can exhibit a large number of useful physical and biological properties. In particular, the inventor has demonstrated that the CD-74-like domain of IGFBP-3 exhibits a number of previously undocumented properties, such as the ability to selectively bind metals such as zinc and nickel. The inventor has also located several previously demonstrated activities of intact IGFBP-3 to this region of the molecule. The exact location of sequence boundaries for peptides is critical to their biological activities, particularly in the case of pro-apoptotic peptides. The inventor has also made the surprising and provocative observation that a peptide representing a 22-amino acid sequence from this region of IGFBP-3 is sufficient to direct the internalization of a covalently attached, much larger protein (green fluorescent protein) into live human embryonic kidney (HEK293) cells. The mechanism used by IGFBP-3 to enter target cells is not well understood, although the existence of a cell surface receptor has been proposed.

Additionally, the inventor has further surprisingly discovered that the cellular internalization of IGFBP-3-derived peptides is mediated by pathways involved in iron transport, particularly ferrous iron ($Fe^{++}$) transport. Accordingly, the IGFBP-3-derived peptides of the invention are considered to be particularly useful for delivering molecules to organs which are heavily implicated in iron metabolism, such as the heart and kidneys. These findings also indicate that reagents which modulate cellular uptake of iron-carrying molecules can be used to modulate the activities of IGFBP-3 and peptides derived from it.

The inventor has also surprisingly found that the addition of a six amino acid sequence to the carboxy-terminal end of the 'core' MBD 14 mer sequence (QCRPSKGRKRGFCW) (SEQ ID NO:3) to create a caveolin consensus binding sequence results in a substantial increase in nuclear translocation activity. Peptides comprising the MBD 14mer core sequence plus a caveolin consensus binding sequence are useful for directing nuclear translocation of therapeutic molecules.

The present invention reveals that short peptides containing just 12–22 amino acids from the C-terminal domain of IGFBP-3 can mimic the full molecule's co-apoptotic, cell-penetrating and metal-binding properties. These peptides ("MBD peptides") offer an attractive alternative to the use of full-length IGFBP-3, for the reasons listed below:

Potency: The amino-terminal domain of IGFBP-3 binds and carries IGFs in circulation, potentiating their anabolic and anti-apoptotic effects on most cell types while the carboxy-terminal domain is believed to mediate IGF-independent effects of IGFBP-3. Thus the efficacy of this molecule as a therapeutic may be inherently buffered by the duality of its function. MBD peptides are up to 3x more active than full-length IGFBP-3 in co-apoptotic assays and, unlike IGFBP-3, MBD activity is not severely inhibited by extracellular matrix and plasma proteins;

Formulation: The central domain of IGFBP-3 is exquisitely sensitive to proteolysis. Due to the limited, solubility of IGFBP-3, its low stability and pronounced tendency to aggregate, the development of suitable formulations and convenient routes of delivery for intact IGFBP-3 is challenging. For example, a 1 mg/kg/day dose of IGFBP-3 (at 7 mg/ml, the maximum solubility in phosphate buffered saline) for a 70 kg adult IGFBP-3 would be 10 ml (NOT suitable for subcutaneous bolus injection), while an MBD PEPTIDE (at 35 mg/ml in PBS) given at 0.5 mg/kg/day to a 70 kg adult would only 1 ml (suitable for subcutaneous bolus injection).

Stability: MBD peptides are stable to heat (95 degrees Celsius for 10 minutes) and are small in size, making them more amenable to transdermal or inhalant-based delivery routes than full-length IGFBP-3.

Cost: For the IGFBP-3 molecule to be biologically active, all its 18 cysteine residues must form intramolecular disulfide bonds. This makes the production of adequate quantities of clinical grade IGFBP-3 in bacterial or yeast systems extremely challenging. Mammalian systems are too expensive for the industrial production of this molecule. Since the human IGFBP-3 cDNA was cloned in 1988, only one group has successfully produced gram quantities of clinical grade recombinant IGFBP-3. The projected selling price of a single 4 mg/kg subcutaneous dose of IGFBP-3, based on production technologies for IGFBP-3 developed and refined over a twelve-year period and using an industry-standard pricing ratio to Cost of Goods (COG), is likely to be in the range of several thousand dollars. Based on reimbursement and other considerations, this price may be prohibitive. MBD peptides, on the other hand, are expected to be cheaper and easier to produce than IGFBP-3 using either synthetic chemical methods or highly efficient biological production systems well known to those skilled in the art.

Sequence alignments, combined with data from several laboratories, can provide insights into the regions of IGFBP-3 that are likely to be structurally autonomous while sufficient to specify the molecule's pro-apoptotic actions on tumor cells. Other studies have shown that other sequences in this same domain are involved in nuclear localization, RXR-alpha-binding, and binding to serum and ECM components (21, 23–25, 35, 40). We have aligned these regions of the molecule with a CD74-homology motif seen in a disparate group of proteins across the animal kingdom (mammalian, frog, fish, fly, nematode). For the purposes of this invention, the CD74-homology domain of IGFBP-3 is defined as comprising approximately the 60 amino acid residues at the carboxy-terminal end of the mature IGFBP-3 protein, or any subset thereof.

FIG. 2 shows an alignment of selected human proteins containing the CD74 motif. Conserved residues are shown in bold. Italicized residues in IGFBP-3 are required for nuclear translocation and collagen binding, but not for IGF-I binding. Asterisks denote residues substituted in the HBD mutant of IGFBP-3, which is impaired in binding plasminogen, prekallikrein, ALS and RXR-alpha. The peptide region denoted by # is sufficient to promote cell internalization when attached to green fluorescent protein. Preliminary data further suggest that a peptide representing part of this region may be sufficient to promote apoptosis in cells in culture.

Disclosed herein are methods for alleviating the symptoms of disease. In one embodiment, an effective amount of IGF-binding protein derivative peptide or small molecule is systemically co-administered with a chemotherapeutic agent to a subject having cancer, thereby alleviating the symptoms of the cancer. Exogenously added IGFBP-3 sensitizes tumors to commonly used chemotherapeutic agents, influencing both tumor size and metastasis. These effects are seen with a variety of agents, including TAXOL®, 5-Fluorouracil, ADRIAMYCIN® and CPT-11, and are believed to reflect pro-apoptotic IGF-I-independent effects of IGFBP-3.

In another embodiment, IGF-binding protein derivative peptide or small molecule is systemically co-administered with other biological modifiers such as ligands of retinoid or thyroid receptors, or antibodies capable of binding target cell molecules, to the subject with disease.

In yet another embodiment, IGF-binding protein derivative peptide or small molecule is administered as described in the other embodiments, but the administration occurs indirectly, using a gene sequence delivered by a viral vector or other vehicle, or using an inducer or antagonist.

In certain aspects, the invention provides methods for alleviating the symptoms of disease, by administering a co-administered agent together with an effective amount of IGF binding protein-derived peptide or small molecule to a subject having the disease.

In some embodiments, the co-administered agent is a chemical agent selected from the group consisting of alkylating agents, antimetabolites, Vinca alkaloids, podophyllotoxins, antitumor antibiotics, nitrosoureas, metallic DNA modifying compounds and microtubule stabilizers, a biological agent selected from the group consisting of nutrient limitation, antibodies, vaccines, peptides, cytokines, receptor ligands and nucleic acids, or a physical agent selected from the group consisting of heat, pressure, osmolarity, acidity and radiation. Preferred co-administered agents include chemical agents selected from the group consisting of doxorubicin, paclitaxel, methotrexate, tamoxifen, cyclophosphamide, vincristine, etoposide, streptozotocin and 5-fluorouracil.

In certain embodiments, the disease treated is cancer of the breast, prostate, colon, ovary, pancreas, stomach, esophagous or lung.

In some embodiments, the IGFBP-3-derived peptide or small molecule is administered at about 0.001 to about 40 milligrams per kilogram total body weight per day (mg/kg/day).

In other aspects, the invention provides methods for alleviating the symptoms of disease by administering an effective amount of IGF binding protein-derived peptide or small molecule, to a subject having the disease.

In certain embodiments, the IGF binding protein-derived peptide is a IGFBP derived proteolysis inhibiting peptide. Such embodiments are useful for reducing tumor invasiveness (e.g., reducing local, regional, and metastatic spread of a tumor), treating disorders associated with excessive bone formation, and reducing or inhibiting vascular restenosis.

In other embodiments, the IGF binding protein-derived peptide is a MBD peptide. Such embodiments are useful for alleviating the symptoms of disorders mediated by chronic inflammatory responses at the cellular level, including cardiovascular diseases (e.g., atherosclerosis), autoimmune diseases including systemic lupus erythematosis (SLE), multiple sclerosis (MS), diabetes (especially type I diabetes), ankylosing spondulitis, ulcerative colitis, inflammatory bowel diseases including Crohn's disease, arthritis (particularly rheumatoid arthritis), asthma and allergy, bone resorptive disorders, opthalmological disorders including retinopathies, and fibrotic diseases.

Additional embodiments utilize MBD peptides, and derivatives thereof, for delivery of therapeutic molecules to tissues of interest, such as cardiac, vascular, muscular, immune, liver, brain and renal tissues, and particularly to organs which are heavily implicated in iron metabolism, such as the heart and kidneys. In such embodiments, conjugates of MBD peptides and therapeutic molecules are administered to subjects in need thereof, such as subjects suffering from cardiac, vascular, muscular, immune, hepatic, neurologic or renal disorders, resulting in amelioration of at least one symptom the disorder sought to be treated.

The invention further provides methods of treating disorders associated with altered iron metabolism, such as neoplasia, Parkinson's disease, and atherosclerosis. A conjugate comprising an MBD peptide and a therapeutic molecule is administered to a subject having a disorder associated with altered metabolism, resulting in amelioratin of at least one symptom of the disorder.

In certain embodiments, the MBD peptide includes a caveolin consensus binding sequence (#x#xxxx#, where '#' is an aromatic amino acid) in addition to, or overlapping with, the MBD peptide sequence. The caveolin consensus sequence may be at the amino terminal or carboxy terminal end of the peptide. In certain preferred embodiments, the caveolin consensus binding sequence is at the carboxy terminal end of the peptide, and overlaps with the MBD core 14mer sequence. Exemplary MBD peptides with caveolin consensus binding sequences include peptides comprising the sequence QCRPSKGRKRGFCWAVDKYG (SEQ. ID NO: 37) or KKGFYKKKQCRPSKGRKRGFCWAVDKYG (SEQ. ID NO: 38).

BRIEF DESCRIPTION OF THE DRAWINGS

FIGS. 1A–1B shows sequences IGFBP-3 in single letter amino acid code. FIG. 1A shows the amino acid sequences of native human IGFBP-3 ($Ala_5$ allelic variant). FIG. 1B shows [N109D]-hIGFBP-3 derivative ($Ala_5$ allelic variant).

FIG. 2 shows an amino acid sequence alignment of selected human proteins containing the CD74 motif.

FIGS. 4A–4B depicts the results of the experiment described in Example 2.

FIG. 6 shows a scheme for production of IGFBP-3 domains using fusion proteins. The lower panel shows SDS-PAGE analysis of purification. Lane 1 shows crude extract digested with 3C proteinase (10:1 dilution); lane 2 shows after Phenyl-Sepharose HIC Chromatography; and lane 3 shows after nickel metal affinity chromatography.

FIGS. 8A–8C shows graphs summarizing the results of co-apoptosis assays described in Example 8.

FIGS. 10A–10B shows the results of the antigenic profiling studies described in Example 11.

FIGS. 11A–11C summarizes the results of experiments which confirm the IGF-independence of the co-apoptotic activity of both IGFBP-3 and MDB2.

FIGS. 12A–12B summarizes the results of experiments showing that the co-apoptotic activity of MDB2 is integrin dependent.

FIGS. 13A–13B summarizes the results of experiments showing that the co-apoptotic activity of MDB2 is sequence specific.

FIGS. 14A–14B summarizes the results of experiments showing that IGFBP-3 stimulates bax-alpha expression, and that bax-alpha expression is correlated with caspase-3 activity.

FIGS. 16A–16B summarizes the results of experiments showing that MDB peptides sensitize carcinoma cells to low doses of cytotoxic chemotherapy agents.

BEST MODE FOR CARRYING OUT THE INVENTION

Figure 3:
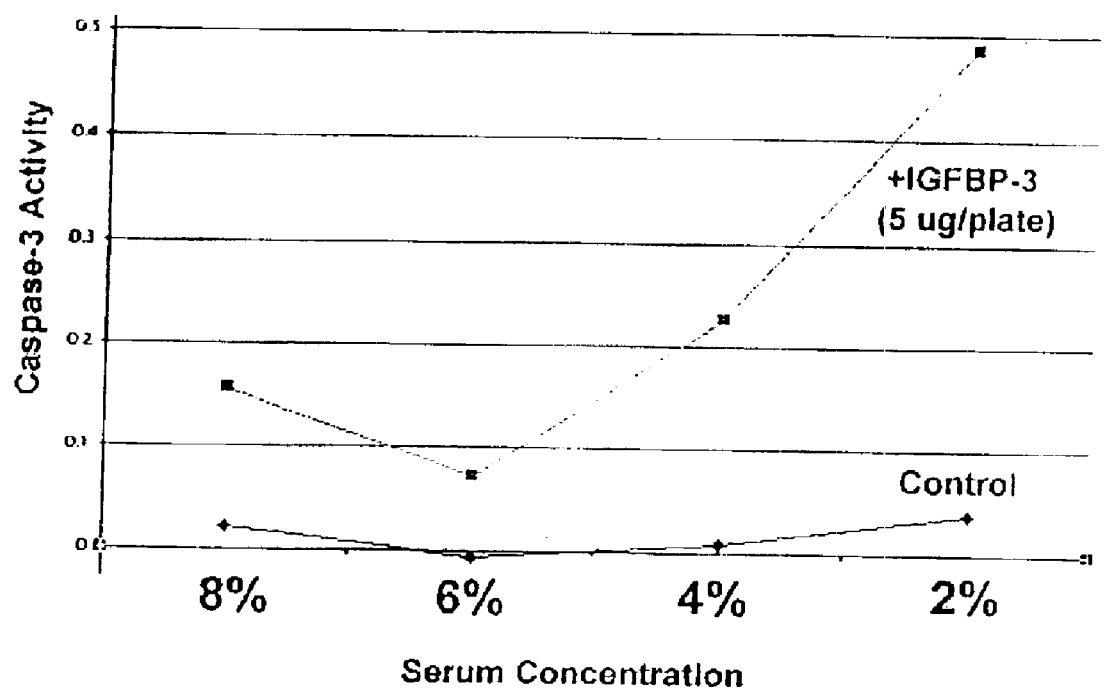
FIG. 3 depicts the results of the experiment described in Example 1.

The invention relates to a number of new peptides (and small molecules which mimic the structure of the peptides) which have a variety of useful properties, including metal-binding, extracellular matrix (ECM) binding, directing cell internalization, inhibiting protease activity, modulation of transcription, apoptosis promotion, angiogenesis inhibition, anti-inflammatory activities, as well as utilities for cell imaging and expression tagging.

Disclosed herein are new methods for the treatment of disease. The various activities of the peptides of the invention may be utilized to treat a range of disorders, including cancer, autoimmune disease, cardiovascular indications, arthritis, asthma, allergy, reproductive indications, retinal proliferative disease, bone disease, inflammatory disease, inflammatory bowel disease, and fibrotic disease.

In certain embodiments, an effective amount of pro-apoptotic peptide and a co-administered agent are systemically administered to a subject suffering from cancer, thereby alleviating the symptoms of the cancer. A wide variety of malignancies may be treated using the methods of the invention, including breast, prostate, colon, ovarian, pancreatic, gastric and lung cancer. The co-administered agent is typically an cytotoxic chemotherapy agent, such as doxorubicin, paclitaxel, methotrexate, tamoxifen, cyclophosphamide, vincristine, etoposide, streptozotocin and 5-fluorouracil Definitions As used herein, the terms "IGF-binding protein" and "IGFBP" refer to natural and derivative molecules based on any of the six human insulin-like growth factor binding proteins 1 through 6. "Derivative peptide or small molecule" refers to peptides or peptidomimetics, that retain, or mimic those structural properties of IGFBPs that are relevant to the instant invention. Derivative peptides herein comprise less than the full length sequence of IGFBP-3. As used herein, a peptide or small molecule is "derived from" an IGFBP if its sequence or structure is identical or homologous to the IGFBP.

"CD74-homology domain peptides or small molecules" means derivative peptides or small molecules containing part of the carboxyterminal 60-amino acid sequence of IGFBP-3.

"Metal-binding domain peptide" or "MBD peptide" means an IGFBP-derived peptide or polypeptide from about 12 to about 60 amino acids long, preferably from about 13 to 40 amino acids long, comprising a segment of the CD-74-homology domain sequence in the carboxy-terminal 60-amino acids of IGFBP-3, comprising the sequence CRPSKGRKRGFC (SEQ ID NO:4) and exhibiting metal-binding properties, but differing from intact IGFBP-3 by exhibiting distinct antigenic properties, lacking IGF-I-binding properties, and lacking the mid-region sequences (amino acids 88–148 of IGFBP-3 sequence). For example, the peptide GFYKKKQCRPSKGRKRGFCW (SEQ ID NO:2) is an example of a metal-binding domain peptide. It binds metal ions but not IGF-I, and polyclonal antibodies raised to this peptide do not substantially cross-react with intact IGFBP-3, and vice versa.

"Extended metal-binding domain peptides" are metal-binding domain peptides linked to additional residues differing from the natural IGFBP-3 sequence. For example, extensions such as the tripeptide asparagine-glycine-arginine (NGR), or a large protein sequence may be added for pharmacokinetic targeting purposes, or for the preparation of conjugates with other molecules such as lipids and nucleic acids ("extended metal-binding domain peptide conjugates").

"Modified metal-domain peptides" are metal-binding domain peptides or extended metal-binding domain peptides in which the natural amino acid sequence has been modified, such modifications including conservative substitutions for the natural amino acid residue at any position in the sequence, alteration of phosphorylation, acetylation, glycosylation or other chemical status found to occur at the corresponding sequence position of IGFBP-3 in the natural context, substitution of D- for L-amino acids in the sequence, or modification of chain backbone chemistry, such as protein-nucleic-acid (PNA).

"Core metal-binding-domain peptides" are peptides less than 14 amino acids long comprising the core 12-mer sequence, CRPSKGRKRGFC (SEQ ID NO:4). For example, CRPSKGRKRGFC (SEQ ID NO:4), QCRPSKGRKRGFC (SEQ ID NO:8) and CRPSKGRKRG-FCW (SEQ ID NO:9) are core metal-binding domain peptides.

"Extended core metal-binding domain peptides" are extended metal-binding domain peptides comprising the core 12-mer sequence CRPSKGRKRGFC (SEQ ID NO:4), but not comprising the following natural IGFBP-3 14-mer sequence: QCRPSKGRKRGFCW (SEQ ID NO:3).

"Modified core metal-binding peptides" are modified metal-binding domain peptides comprising the core 12-mer sequence CRPSKGRKRGFC (SEQ ID NO:4), but not comprising the following natural IGFBP-3 14-mer sequence: QCRPSKGRKRGFCW (SEQ ID NO:3).

"Retro metal-binding domain peptides" are derivatives of metal-binding domain peptides containing either D- or L-amino acids in reverse order.

"Cell internalization peptides" means a peptide or other proteinaceous molecule, or mutant or other derivative thereof, comprising the sequence KKG-FYKKKQCRPSKGRKRGFCW (SEQ ID NO:7) or part thereof, which is present in the CD74-homology domain of IGFBP-3.

"Plasma circulatory peptide" means CD74-homology, domain peptide retaining some or all of the circulatory plasma protein binding characteristics of IGFBP-3. Binding to plasminogen, transferrin, kallikrein, acid-labile subunit, or fibrinogen are examples in this category.

"ECM-binding peptide" means CD74-homology domain peptide retaining some or all of the extracellular matrix component binding characteristics of IGFBP-3. Binding to heparin, collagen and cell surface components are examples in this category.

"Protease inhibitor peptide" means CD74-homology domain peptide retaining some or all of the protease inhibitor characteristics of IGFBP-3. In particular this refers to inhibition of cysteine proteases, serine proteases and metalloproteases. "Expression vector tag" means any CD74-homology domain peptide sequence included in a gene expression vector wherein the properties of IGFBP-3 retained in the vector tag are instrumental in facilitating the use of the vector for research, high-throughput screening or other applications well recognized in the art.

"Pro-apoptotic peptide" means a CD74-homology domain peptide retaining some or all of the pro-apoptotic characteristics of IGFBP-3 but not its IGF-binding characteristics. In one embodiment, "core" pro-apoptotic peptides contain the first sequence QCRPSKGRKRGFC (SEQ ID NO:8), but not the second sequence KKGFYKKK (SEQ ID NO:10), which lies almost immediately adjacent to the first sequence in the intact IGFBP-3 molecule. As is known to those skilled in the art, it is possible to make sequence changes to any protein or peptide sequence without substantially modifying its properties. Thus, peptide sequences exhibiting comparable biological activity and at least 80% sequence homology, more preferably 85, 90, 95, 98, or 99% sequence homology, to any of the above sequences are also covered by the above definitions.

The term "co-administered agent", as used herein, refers to a chemical agent; a biological agent such as an antibody, vaccine, nutrient, cytokine, nucleic acid or receptor ligand such as growth factor, retinoid or thyroid receptor ligand; and a physical agent, such as radiation, acidity and heat. Co-administered agents preferably have an anti-tumor activity when administered in the absence of IGFBP.

"Chemical agents" include all common chemotherapeutic agents such as alkylating agents (e.g. busulfan, cyclophosphamide, ifosfamide), antimetabolites (e.g. Ara-C, 5-fluorouracil, methotrexate), Vinca alkaloids (e.g. vinblastine, vincristine), podophyllotoxins (e.g. VM-26, etoposide), antibiotics (e.g. bleomycin, doxorubicin/ ADRIAMYCIN®), nitrosoureas (e.g. BCNU, streptozotocin), and metallic DNA modifying compounds (e.g. carboplatin, cisplatin), and microtubule stabilizers (e.g., paclitaxel/TAXOL®). Chemical agents also include chemical compounds that directly affect a targeted receptor by reducing levels of the cognate ligand, by acting on the targeted receptor or acting on the signaling pathway of the targeted receptor. For example, the thyroid axis may be indirectly manipulated via antagonists such as thyroid axis antagonists. As an example, the term "thyroid axis antagonist" refers to a compound which acts to decrease thyroid hormone activity in a subject. Thyroid axis antagonists include 6-n-propyl-2-thiouracil (propylthiouracil or PTU), methimazole, carbimazole, and other compounds known to the art to reduce thyrotropic hormones, thyroid hormones, or thyroid receptor signaling.

The term "treatment regimen", refers to a course of therapy. Treatment regimens may utilize a single agent such as a single chemical agent, but more typically involve two or more different agents (e.g., combination therapy with multiple different cytotoxic chemotherapy agents), and may involve two or more different types of agents (e.g., administration of a chemical agent such as paclitaxel in combination with a physical agent such as ionizing radiation). Treatment regimen may also refer to nutritional, stress or exercise regimen.

The term "alleviating", as used herein, refers to an improvement, lessening, stabilization, or diminution of a symptom of a disease. "Alleviating" also includes slowing or halting progression of a symptom. For example, alleviating a symptom of cancer includes slowing or stabilizing tumor growth, reducing tumor size, or eliminating the tumor entirely.

The term "subject", as used herein, refers to a vertebrate individual, including avian and mammalian individuals, and more particularly to sport animals (e.g., dogs, cats, and the like), agricultural animals (e.g., cows, horses, sheep, and the like), and primates (e.g., humans).

Sequence "identity" and "homology", as referred to herein, can be determined using BLAST (Altschul, et al., 1990, *J. Mol. Biol.* 215(3):403–410), particularly BLASTP 2 as implemented by the National Center for Biotechnology Information (NCBI), using default parameters (e.g., Matrix 0 BLOSUM62, gap open and extension penalties of 11 and 1, respectively, gap x_dropoff 50 and wordsize 3). Unless referred to as "consecutive" amino acids, a sequence optionally can contain a reasonable number of gaps or insertions that improve alignment.

As used herein, the term "conjugate" includes both covalent and noncovalent conjugates between a peptide and second molecule (such as a transcriptional modulator or a therapeutic molecule). Noncovalent conjugates may be created by using a binding pair, such as biotin and avidin or streptavidin or an antibody (including Fab fragments, scFv, and other antibody fragments/modifications) and its cognate antigen.

As used herein, the term "comprising" and its cognates are used in their inclusive sense; that is, equivalent to the term "including" and its corresponding cognates.

As used herein, the singular form "a", "an", and "the" includes plural references unless indicated otherwise.

IGF-binding Protein Derivative Peptide and Small Molecule Compositions

IGF-binding protein derivative peptide or small molecule for use in accordance with the instant inventive methods may be derived from any species, although species-matched IGF-binding protein (i.e., IGF-binding protein derivative peptide or small molecule based on the native sequence from the same species as the subject to which the IGF-binding protein derivative peptide or small molecule is to be administered) is preferred (e.g., when the IGF-binding protein derivative peptide or small molecule is intended to be administered to a human subject, it is preferred that the IGF-binding protein derivative peptide or small molecule be derived from a human IGFBP). IGF-binding protein derivative peptide or small molecule for use in the instant invention is uncomplexed IGF-binding protein derivative peptide or small molecule, that is, administered in the absence of IGF (e.g., not administered as IGF-I complex), and is preferably administered without any IGF protein. Preferably, IGF-binding protein derivative peptides or small molecules are derived from IGFBP-3.

One of the naturally occurring protein sequences for IGFBP-3 is shown in FIG. 1. Human IGFBP-3 is found in two naturally occurring allelic variants; alanine may be found at position 5 of the mature protein (shown in FIG. 1a), or alternately glycine may be found in this position. Additionally, other variants of IGFBP-3 may be created. For example, [N109D]-IGFBP-3 is a derivative of IGFBP-3 that has an amino acid sequence alteration at position 109 of the mature sequence but behaves very similarly to wild type IGFBP-3 in most assays tested to date. Point mutant derivatives also include mutants selectively debilitated in their ability to bind IGF-I, IGF-II, or any other known ligands of IGFBPs. For example, it has been shown that point mutations at positions corresponding to one or more of the conserved or semi-conserved residues $Val_{49}$, $Tyr_{50}$, $Pro_{62}$, $Lys_{68}$, $Pro_{69}$, $Leu_{70}$, $Ala_{72}$, $Leu_{73}$, and $Leu_{74}$ of IGFBP-5 may be debilitated in IGF-I binding. Many of these residues are well-conserved in the other IGF-binding proteins as well. Mutations at positions 228 and 230 of the mature sequence of IGFBP-3 are believed to affect nuclear translocation and binding to extracellular matrix proteins such as collagen.

Deletion mutants of IGFBP-3 or peptide derivatives based on parts of the IGFBP-3 sequence, may also be used as the template for design of derivative peptides and small molecules. The IGFBP-3 molecule consists of 264 amino acids and has three major structural domains. The cysteine-rich amino terminal domain (roughly the first 100 amino acids of the mature sequence) is known to be essential for high-affinity binding of IGFs. The middle domain (about 80 amino acids) has no cysteine residues, and is very susceptible to proteases. It may also play a role in binding specific cellular receptors. The carboxy-terminal domain (about 80 amino acids) is also cysteine-rich and contains sequences essential for binding extracellular matrix molecules such as heparin and collagen, serum molecules such as ALS, plasminogen, and fibrinogen, nuclear receptors such as RXR, and importin. Methods for nucleic acid manipulation, protein expression and protein purification for obtaining deletion or point mutants are known in the art.

Once a domain of IGFBP-3 has been defined by point mutation or deletion analysis as necessary and sufficient for a particular biological activity, such as the sensitization of target cells, it is possible to design smaller molecules, such as peptides, consisting of part of the IGFBP sequence. For example, one or more of the sequences (H2N) . . . DRKGFYKKKQCRPSKGRKRGFCW . . . (COOH); (SEQ ID NO:1)

(H2N) . . . GFYKKKQCRPSKGRKRGFCW . . . (COOH); (SEQ ID NO:2)

(H2N) . . . QCRPSKGRKRGFCW . . . (COOH); and (SEQ ID NO:3)

(H2N) . . . CRPSKGRKRGFC . . . (COOH) (SEQ ID NO:4)

may be sufficient to mimic some of the biological effects of IGFBP-3, although certain embodiments of the invention may exclude peptides which comprise or consist of the sequences DKKGFYKKKQCRPSKGRKRGFCW (SEQ ID NO:1) and QCRPSKGRKRGFCW (SEQ ID NO:3).

Although the three-dimensional structure of IGFBP-3 is not known, the structure of CD74 invariant chain, which shares considerable homology with the relevant region of the IGFBP-3 molecule, has been described (Ghosh, et al, Nature 378: 457–462, 1995) Peptidomimetic molecules derived from an IGFBP (preferably IGFBP-3) sequence may be created by reference to the three-dimensional structure of CD74 invariant chain, using techniques known in the art. Any of these derivative molecules may be assayed for the desired biological activities, including the ability to sensitize target cells to chemical treatments. Based on the results of these assays, a small number of IGFBP-3 mutants or derivatives with altered characteristics may be selected for clinical testing in the context of human disease.

IGFBP derived protease inhibitor peptides and peptidomimetics are also contemplated within the present invention. Such peptides and peptidomimetics are useful as inhibitors of proteolytic activity that cleaves IGFBP-4. As noted above, cleavage of IGFBP-4 by certain proteases results in an effective increase in IGF-I activity, which is important in a number of different processes, including proliferation of vascular smooth muscle cells. Accordingly, protease inhibitor peptides are useful for the inhibition of vascular restenosis, particularly arterial restenosis following angioplasty (with or without stent implantation) and coronary artery bypass surgery. Additionally, proteolysis of IGFBP-4 is important in promoting bone formation. Accordingly, proteolysis inhibiting peptides are also useful for inhibiting bone formation in indication which involve excessive bone formation. Proteolysis, inhibiting peptides are also useful for inhibition of cysteine proteases such as Cathepsin B and metalloproteases such as MMP-2 and MMP-9, which are known to be associated with tumor invasiveness. Accordingly, the invention provides methods of reducing tumor invasiveness (e.g., reducing local, regional, and metastatic spread of a tumor) by administering an IGFBP derived proteolysis inhibiting peptide.

Also provided are peptides incorporating the MBD peptide core 14mer sequence plus a caveolin consensus binding sequence. The caveolin consensus sequence may be located upstream (i.e., towards the amino terminus) or downstream (i.e., towards the carboxy terminus) of the peptide, and may overlap with the MBD core 14mer sequence. Exemplary embodiments include the peptides MBD20 (QCRPSKGRKRGFCWAVDKYG) (SEQ ID NO:37) and MBD21 (KKGFYKKKQCRPSKGRKRGFCWAVDKYG) (SEQ ID NO:38).

IGF-binding Protein Derivative Peptide Production

The IGF-binding protein or derivative is normally produced by recombinant methods, which allow the production of all possible variants in IGFBP sequence. Techniques for the manipulation of recombinant DNA are well known in the art, as are techniques for recombinant production of proteins (see, for example, an Sambrook et al., MOLECULAR CLONING: A LABORATORY MANUAL, Vols. 1–3 (Cold Spring Harbor Laboratory Press, 2 ed., (1989); or F. Ausubel et al., CURRENT PROTOCOLS IN MOLECULAR BIOLOGY (Green Publishing and Wiley-Interscience: New York, 1987) and periodic updates). Derivative peptides or small molecules of known composition may also be produced by chemical synthesis using methods well known in the art.

Nucleic acid vectors containing sequences encoding IGF-binding protein derivative peptides or small molecules may utilize the varied properties of these molecules to facilitate the implementation of research, high-throughput screening or other genomics- and proteomics-related technologies. In particular the metal-binding characteristics of some CD74-like peptides may aid in rapid affinity purification of expressed gene products from crude extracts using immobilized metal affinity chromatography (IMAC) resins such as His-Bind (Novagen Inc., Madison, Wis.), Nickel-NTA (Qiagen Inc., Carlsbad, Calif.) and Talon (Clontech Inc., Palo Alto, Calif.) resins, using the protocols recommended by the manufacturers of such resins. Likewise, the protease inhibitor characteristics of some CD74-like peptides may aid in expressed gene product stability during purification. The cell internalization properties of some CD74-like peptides may aid in rapid screening of certain gene products in mammalian cells, particularly in those cases where transport to the cell nucleus may facilitate screening of biological properties. The use of selective proteolytic cleavage sites within IGF-binding protein-derived sequences in vectors can aid in the recovery of properly folded domains of IGFBPs or peptide derivatives thereof. The use of human rhinovirus 3C proteinase for effecting post-expression cleavage of gene products containing such sequences is particularly recommended (ref).

Preferably, the IGF-binding protein or derivative is produced using a bacterial cell strain as the recombinant host cell. An expression construct (i.e., a DNA sequence comprising a sequence encoding the desired IGF-binding protein or derivative operably linked to the necessary DNA sequences for proper expression in the host cell, such as a promoter and/or enhancer elements at the 5' end of the construct and terminator elements in the 3' end of the construct) is introduced into the host cell. The DNA sequence encoding the IGF-binding protein or derivative may optionally linked to a sequence coding another protein (a "fusion partner"), to form a fusion protein. Preferably, the DNA sequence encoding the IGF-binding protein or derivative is linked to a sequence encoding a fusion partner as described in U.S. Pat. No. 5,914,254. The expression construct may be an extrachromosomal construct, such as a plasmid or cosmid, or it may be integrated into the chromosome of the host cell, for example as described in U.S. Pat. No. 5,861,273.

Conjugates and Fusions Incorporating IGFBP-derived Peptides

As disclosed herein, the peptide KKG-FYKKKQCRPSKGRKRGFCW (SEQ ID NO:7) is capable of directing cellular internalization of an unrelated protein, and is particularly useful for directing cellular internalization into cardiac and renal tissues. Accordingly, the invention provides fusions and/or conjugates of IGFBP-derived internalization peptides and small molecules with molecules which are desired to be internalized into cells. The fusion partner molecules may be polypeptides, nucleic acids, or small molecules which are not normally internalized (e.g., because of large size, hydrophilicity, etc.). As will be apparent to one of skill in the art, such fusions/conjugates will be useful in a number of different areas, including pharmaceuticals (to promote internalization of therapeutic molecules which do not normally become internalized), gene therapy (to promote internalization of gene therapy constructs), and research (allowing 'marking' of cells with an internalized marker protein). Preferred IGFBP-derived internalization promoting peptides are peptides comprising the sequence KKGFYKKKQCRPSKGRKRGFCW (SEQ ID NO:7) or a sequence having at least 80, 85, 90, 95, 98, or 99% homology to said sequence, wherein the peptide does not comprise the full sequence of IGFBP-3. Fusions of IGFBP-derived internalization peptides and polypeptides are preferably made by creation of a DNA construct encoding the fusion protein, but such fusions may also be made by chemical ligation of the internalization peptide and the polypeptide of interest. Conjugates of IGFBP-derived internalization peptides and nucleic acids or small molecules can be made using chemical crosslinking technology known in the art. Preferably, the conjugate is produced using a heterobifunctional crosslinker to avoid production of multimers of the internalization peptide.

Conjugates of an IGFBP-derived internalization promoting peptide and transcriptional modulators (e.g., transcription factors) are provided by the invention. Nearly all transcription factors are intracellular proteins which are not normally capable of being internalized from the extracellular milieu, making them unsuitable as pharmaceutical agents in their native form. However, when fused or conjugated with an IGFBP-derived internalization promoting peptide, the transcription factor can be internalized and affect cellular transcription. For example, T-bet (Szabo et al., 2000, *Cell* 100(6):655–69), a transcription factor that appears to commit T lymphocytes to the $T_{h1}$ lineage, can be fused to a an IGFBP-derived internalization promoting peptide to create a molecule useful in immunomodulation.

Conjugates of cell internalization peptides and therapeutic molecules are also provided. Cell internalization peptides may be conjugated with any therapeutic molecule which is desired to be delivered to the interior of a cell, including antisense oligonucleotides and polynucleotide constructs (e.g., encoding therapeutic molecules such as growth factors and the like).

Peptides comprising cell internalization peptide (e.g., the MBD core 14mer) and a caveolin consensus binding sequence (MBD/caveolin peptides) may also be incorporated into conjugates. MBD/caveolin peptides may be conjugated with any therapeutic molecule that is desired to be delivered to the interior of a cell, including antisense oligonucleotides and polynucleotide constructs (e.g., encoding therapeutic molecules such as growth factors and the like).

Also provided are fusion/conjugate molecules comprising a marker moiety and an IGFBP-derived internalization promoting peptide. Marker moieties useful in such fusion/conjugate molecules include proteins such green fluorescent protein, luciferase, and other proteins which can be detected by virtue of an enzymatic activity (such as alkaline phosphatase, β-galactosidase, and the like), as well as 'expression tag' moieties which can be detected by a secondary detection system such as specific antibodies. Expression tag moieties are well known, and include peptides derived from myc and other proteins. Due to the localization of IGFBP-3 to the nucleus of rapidly dividing cells, fusion/conjugate molecules comprising IGFBP-derived internalization promoting peptides comprising the sequence KKG-FYKKKQCRPSKGRKRGFCW (SEQ ID NO:7) or a sequence having at least 80, 85, 90, 95, 98, or 99% homology to said sequence, are believed to be particularly useful for cell labeling uses and diagnostic uses. Other contemplated uses of such fusion/conjugate molecules comprising an IGFBP-derived internalization promoting peptide include pharmacokinetic studies of pharmaceutical molecules incorporating an IGFBP-derived internalization promoting peptide.

Fusion/conjugate molecules comprising a ECM-binding peptide are also provided. The fusion/conjugate molecules are targeted to the extracellular matrix through the ECM binding peptide. A peptide or peptidomimetic derived from the CD74 homology domain of IGFBP may be conjugated or produced as a fusion with a different polypeptide or with a small molecule. In alternative embodiments, the ECM binding peptide may be conjugated with or inserted into the surface of a liposome (or other encapsulation formulation) to target the combination to the extracellular matrix. While not wishing to be bound by any particular theory, the inventor believes that IGFBP derived ECM binding peptides are useful for both ECM binding as well as targeted release of the fusion/conjugate partner at sites in which IGFBP-cleaving protease is present.

As disclosed in Example 3, the inventor has discovered the presence of a metal-binding motif in the IGFBP-3 molecule, allowing practical recovery of domains containing this motif. The IGFBP-derived peptides DKKG-FYKKKQCRPSKGRKRGFCW (SEQ ID NO:1) and QCRPSKGRKRGFCW (SEQ ID NO:3) each bound to an affinity column loaded with nickel. Such metal binding properties may be used for purification of desired peptides from complex mixtures (such as bacterial cell lysates). Typically, a DNA sequence encoding either peptide (or homologue thereof having metal binding activity and at least 80, 85, 90, 95, 98, or 99% sequence homology) is fused to a DNA sequence encoding a polypeptide of interest, wherein the peptide does not comprise the full sequence of IGFBP-3. The sequence encoding the metal binding peptide may be fused to the 5' or 3' end of the DNA sequence encoding the polypeptide of interest, and may even be inserted within the sequence of interest (although this is less preferred). Preferably, DNA encoding for a recognition site for an endoprotease is inserted between the sequence encoding the metal binding peptide and the polypeptide of interest, to allow removal of the metal binding peptide. Useful protease recognition sites include the recognition site of human rhinovirus 3C protease, enterokinase, Factor Xa, and ubiquitin (the recognition site of ubiquitinase). The DNA encoding the fusion polypeptide (comprising the IGFBP-derived metal binding peptide and the polypeptide of interest, and optionally the protease recognition site,) is then inserted into any convenient expression vector comprising the DNA sequences necessary for transcription and translation of the encoded fusion polypeptide. The DNA expression construct is transformed into a recombinant host, such as *E. coli,* or *S. cerevisiae,* and recovered using standard methods known in the art. The fusion polypeptide can then be purified using an affinity column loaded with a divalent cation such as zinc or nickel, as is well known in the art. If the fusion polypeptide comprises a protease recognition site, the cognate protease may be used to cleave the metal binding peptide from the polypeptide of interest at an appropriate point in the purification process.

Also disclosed are methods for generating properly folded sub-domains of IGFBP-3. The practical significance of this approach in the case of IGFBP-3 is that numerous unsuccessful attempts have already been made, in a number of laboratories, to express truncated segments of IGFBP-3 in properly folded form. To date, these have proved relatively unsuccessful in generating such properly folded molecules as a major percentage of the total expressed product. By generating the intact molecule and cleaving it post facto, it is possible to generate folded domains with substantially higher efficiencies.

As demonstrated in Example 5, properly folded sub-domains of IGFBP-3 may be produced by engineering target sites for a specific protease at strategic locations in the IGFBP-3 sequence, expressing the construct, and cleaving the expressed protein with the cognate protease. As will be apparent to one of skill in the art, this method is useful for production of both naturally occurring and variant sub-domains of IGFBP-3. The techniques for carrying out this method are well known in the art, and involve recombinant DNA engineering to insert protease recognition sites into the IGFBP-3 sequence. A variety of different protease recognition sites are known, as discussed above, and any convenient protease recognition site may be used, so long as the site is not already present in the IGFBP-3 sequence. The recognition site of the 3C protease of human rhinovirus is a preferred protease recognition site. The construct containing the DNA sequence encoding IGFBP-3 with inserted protease sites is then inserted into an appropriate expression vector comprising the signals necessary for transcription and translation of the IGFBP-3 construct sequence. The IGFBP-3 is then produced by transformation of the expression construct into an appropriate recombinant host and expressed. Preferably, the IGFBP-3 is purified from the recombinant expression system, refolded (if necessary), then cleaved to render properly folded sub-domains of IGFBP-3.

Therapeutic Administration

An IGF-binding protein derivative peptide or small molecule, in combination with agents or treatment regimens causing cellular damage or stress, may be used to treat any disease or disorder for which cytotoxic or cytostatic therapy is indicated, including cancer, preferably carcinomas of the breast, prostate, colon and lung, hyperproliferative disorders including proliferation of inflammatory or other immune-related cells, and arterial restenosis (e.g., after angioplasty and/or coronary artery bypass surgery). In certain embodiments, the co-administered agent is a chemotherapy agent (e.g., paclitaxel, vincristine, and the like), which may be conjugated to an IGFBP-derived ECM binding peptide to provide targeting and localization.

The invention also provides methods of methods of reducing tumor invasiveness (e.g., reducing local, regional, and metastatic spread of a tumor), methods of reducing bone formation, particularly in disorders associated with excessive bone formation, and methods of reducing or inhibiting vascular restenosis by administering an IGFBP derived proteolysis inhibiting peptide.

The invention further provides methods of treating (e.g., alleviating the symptoms of) disorders including cardiovascular diseases including atherosclerosis, autoimmune diseases including systemic lupus erythematosis (SLE), multiple sclerosis (MS), diabetes (especially type I diabetes), ankylosing spondulitis, ulcerative colitis, inflammatory bowel diseases including Crohn's disease, arthritis (particularly rheumatoid arthritis), asthma and allergy, bone resorptive disorders, opthalmological disorders including retinopathies, and fibrotic diseases. As discussed in the Background, supra, these disorders are mediated by chronic inflammatory responses at the cellular level. In accordance with the invention, these disorders are treated by administration of an effective amount of a MBD peptide of the invention.

Also provided are therapeutic methods comprising administration of compositions comprising fusions or conjugates of transcriptional modulators and IGFBP-derived internalization peptides. In certain embodiments, the IGFBP-derived internalization peptide further comprises a caveolin consensus binding sequence. In some embodiments, the fusion or conjugate comprises an IGFBP-derived internalization peptide and a transcription factor such as T-bet. T-bet containing conjugates are useful for immunomodulation, shifting or biasing an immune response towards a $T_{h1}$ response, which can alleviate symptoms of disorders such as allergy, auto immune disease such as rheumatoid arthritis, and other $T_{h2}$ mediated disorders.

Further provided are methods of treating cardiac, vascular, muscular, immune, liver, brain and renal disorders, comprising administering conjugates of a therapeutic molecule and an IGFBP-derived internalization peptide. In certain embodiments, the IGFBP-derived internalization peptide further comprises a caveolin consensus binding sequence. These embodiments exploit the differential uptake of IGFBP-derived internalization peptides into cardiac, skeletal muscle, splenic, and renal tissue, delivering the therapeutic molecule to interior of cells in the target tissue. The therapeutic molecule may be any molecule which requires cellular internalization for activity in the target organ. One class of preferred therapeutic molecules for use in these embodiments is antisense oligonucleotides. Small inhibitory RNAs (siRNAs) is also a preferred class of therapeutic molecules. For treatment of cardiac and renal disorders, the conjugate may be simply administered, generally by a parenteral route. In certain embodiments, administration of the conjugate is preceded by an administration of an IGFBP-derived internalization peptide in the absence of the therapeutic molecule. Such pretreatment may be carried out for any convenient period of time, such as about 2 days to about 4 weeks, or 4 days to three weeks, or one week to 18 days prior to administration of the therapeutic molecule/IGFBP-derived internalization peptide conjugate. For example, immediately following myocardial infarction molecules designed to prevent death of cardiomyocytes, such as appropriate pro-survival genes (e.g., anti-sense oligonucleotides which inhibit the expression of bax-alpha or caspase-3, or polynucleotides which direct the expression of bcl-2) may be systemically administered. In other embodiments, such conjugates may be administered to ameliorate the effects of renal insults, such as ischemia, hepatic insults, such as drug overdose (e.g., acetominophen or acetominophen in combination with alcohol) or exposure to hepatotoxic chemicals (e.g., by ingestion of toxic mushrooms such as *Amanita phalloides*). Conjugates of the invention may also be used to deliver therapeutic molecules to skeletal muscle and cells of the immune system, exploiting the localization of MBD peptides to muscle and spleen, respectively.

The invention also provides methods of treating disorders which are associated with altered iron metabolism, such as neoplasia, Parkinson's disease, and atherosclerosis. An IGFBP-derived internalization peptide (e.g., an MBD peptide) conjugated with a therapeutic molecule is administered to a subject having a disorder associated with altered iron metabolism, resulting in amelioration of at least one symptom of the disorder. In certain embodiments, the IGFBP-derived internalization peptide further comprises a caveolin consensus binding sequence. For example, the increased iron uptake in neoplastic cells, Parkinson's disease, and atherosclerosis may be exploited to deliver therapeutic molecules to the affected cells in these disorders in the form of a conjugate with an IGFBP-derived internalization peptide (e.g., a MBD peptide).

Molecules comprising an IGF-binding protein derivative peptide or small molecule are preferably administered via oral or parenteral administration, including but not limited to intravenous (IV), intraperitoneal (IP), intramuscular (IM), subcutaneous (SC), intradermal (ID), transdermal, inhaled, and intranasal routes. IV, IP, IM, and ID administration may be by bolus or infusion administration. For SC administration, administration may be by bolus, infusion, or by implantable device, such as an implantable minipump (e.g., osmotic or mechanical minipump) or slow release implant. The IGF-binding protein derivative peptide or small molecule may also be delivered in a slow release formulation adapted for IV, IP, IM, ID or SC administration. Inhaled IGF-binding protein derivative peptide or small molecule is preferably delivered in discrete doses (e.g., via a metered dose inhaler adapted for protein delivery). Administration of a molecule comprising an IGF-binding protein derivative peptide or small molecule via the transdermal route may be continuous or pulsatile. Administration of derivative peptides or small molecules may also occur orally.

For parenteral administration, compositions comprising an IGF-binding protein derivative peptide or small molecule may be in dry powder, semi-solid or liquid formulations. For parenteral administration by routes other than inhalation, the composition comprising an IGF-binding protein derivative peptide or small molecule is preferably administered in a liquid formulation. Compositions comprising an IGF-binding protein derivative peptide or small molecule formulations may contain additional components such as salts, buffers, bulking agents, osmolytes, antioxidants, detergents, surfactants, and other pharmaceutical excipients as are known in the art.

A composition comprising an IGF-binding protein derivative peptide or small molecule is administered to subjects at a dose of about 0.001 to about 40 mg/kg/day, more preferably about 0.01 to about 10 mg/kg/day, more preferably 0.05 to about 4 mg/kg/day, even more preferably about 0.1 to about 1 mg/kg/day.

As an alternative to administration of a composition comprising an IGFBP derivative peptide or small molecule, a nucleic acid construct encoding the a composition comprising an IGFBP derivative peptide or small molecule may be administered. The construct contains a polynucleotide sequence encoding the composition comprising the IGFBP derivative peptide, and normally contains sequences operably linked to the IGFBP derivative peptide sequence which result in expression and translation of the composition comprising the IGFBP derivative peptide sequence in the cells (e.g., a promoter/enhancer, translation initiation site, polyadenylation signal, etc.), although constructs which are designed to integrate into the cell chromosome are also contemplated (e.g., where the construct contains sequence which facilitates integration into the host chromosome, such as sequences homologous to the recipient cells' chromosome flanking the IGFBP derivative peptide sequence).

Methods of gene transfer are well known in the art, and include in vitro methods (e.g., transformation of cultured cells, preferably autologous cells, which are reintroduced into the subject), ex vivo methods (e.g., transformation of cells which have not been cultured in vivo, preferably autologous cells, with are reintroduced into the subject), and in vivo methods (e.g., transformation of cells in situ by administration of a nucleic acid construct to the subject). Methods for accomplishing such gene transfer are well known in the art, and include standard transformation methods including calcium phosphate transformation, ballistic transformation, electroporation, lipid-mediated transformation, naked DNA transfer, and viral-mediated transfer (e.g., adenovirus and adeno-associated virus vectors).

The composition comprising an IGF-binding protein derivative peptide or small molecule is administered to the subject together with one or more of the following co-administered agents: a chemotherapeutic agent; an antibody; physical stress, such as radiation; a treatment regimen, such as a nutritional regimen; or a ligand of a receptor present on the target cells, such as retinoid receptors and thyroid receptors. The administration of the two agents may be simultaneous, overlapping, or separated in time, as long as the subject experiences exposure to both agents at the same time. Where the two agents are formulated for the same route and schedule of administration, the administration is preferably simultaneous or nearly simultaneous (e.g., concurrent or serial injections). However, in some embodiments, the routes and schedules of administration for the two agents will be different, making simultaneous administration inconvenient. A subject will be considered to have been administered both agents if the subject experiences simultaneous systemic exposure to both compounds, regardless of when or how the compounds were administered.

In methods requiring the administration of co-administered agent with the composition comprising an IGF-binding protein derivative peptide or small molecule, the dose of the co-administered agent is normally titrated for the individual subject, as is known in the art for that agent. Co-administered agents may be produced in any formulation known to the art, including parenteral and oral dosage forms. Oral formulations are preferred, but parenteral formulations are also acceptable, and may be more convenient in an in-patient setting. Formulations for parenteral administration are generally formulated as liquids, but may also be in gel or solid depot form. Formulations for oral administration are generally in tablet or capsule form, although syrups and liquids are also acceptable. Formulations of co-administered agents generally include excipients, such as salts, buffers, bulking agents, detergents, binding agents, surfactants, stabilizers, preservatives, anti-oxidants, lubricants, coating agents, and other pharmaceutically acceptable excipients as are known in the art.

The dosage and mode of administration of the co-administered agent should be adjusted according to the identity, formulation, route of administration and other relevant characteristics pertaining to the co-administered agent, as is known in the art.

Inducers and antagonists would be administered in a similar way. As an example: Where the antagonist is propylthiouracil, the dose of propylthiouracil may be from 1 to 400 mg/day. A subject is normally initiated with a dose of 50 to 400 mg/day, typically divided into three equal doses, and maintained at 50 to 100 mg/day divided into two or three equal doses. For methimazole and carbimazole, the dose may be from 0.1 to 50 mg/day. Typically, a subject is initiated with 5 to 50 mg/day, and maintained on 1 to 5 mg/day.

As will be understood by those of skill in the art, the symptoms of disease alleviated by the instant methods, as well as the methods used to measure the symptom(s) will vary, depending on the particular disease and the individual patient.

Patients treated in accordance with the methods of the instant invention may experience alleviation of any of the symptoms of their disease. For example, cancer patients treated with a MBD peptide and a co-administered agent may experience tumor stabilization (e.g., may fail to progress), tumor shrinkage, or tumor elimination. Treatment with MBD peptide and a co-administered agent may also result in reduced incidence of metastasis or reduced numbers of metastatic tumors. Cardiovascular disease patients treated with MBD peptide may experience reduction or elimination of any of their symptoms, including vascular stenosis and angina, and/or a reduction in number, size or formation of atherosclerotic plaques. Patients having autoimmune disease who are treated with MBD peptides may experience reduction, elimination, or stabilization of any of their symptoms, such as renal flares, fatigue, weight loss, arthralgia, butterfly rash, anemia (SLE), or weakness, paresthesia, number or size of sclerotic brain lesions (MS), or pain, stiffness, swelling or improvements or stabilization of range of motion (arthritis, particularly rheumatoid arthritis), or abdominal/epigastric pain, cramping, diarrhea (inflammatory bowel disease including Crohn's disease), or fasting serum glucose levels or insulin requirement (diabetes), or wheezing, coughing, peak expiratory flow rate or need for 'rescue' medications such as beta agonists (asthma), or allergic rhinitis (allergy). Retinopathy patients treated with MBD peptides may experience improvement or stabilization in visual acuity. Patients having bone resorptive diseases such as osteoporosis may experience an improvement, stabilization, or decrease in rate of loss of bone mass, which may manifest itself as a reduced risk or rate of bone fracture.

Kits

The invention provides kits comprising IGFBP derived peptides or small molecules. The kits comprise at least one package comprising a composition comprising an IGFBP derived peptide or small molecule. Optionally, the kits may also include a set of instructions for use of the composition.

The compositions included within the kits may be an IGFBP derived peptide or small molecule, or a fusion/conjugate comprising an IGFBP derived peptide or small molecule. In certain embodiments, the kit may also contain at least one package of a co-administered agent, such as a cytotoxic chemotherapy drug (e.g., paclitaxel or doxorubicin). The containers of the composition comprising the IGFBP derived peptide or small molecule (and optional co-administered agent) may be unit doses, bulk packages (e.g., multi-dose packages) or sub-unit doses.

In embodiments comprising instructions, the instructions generally include information as to dosage, dosing schedule, and route of administration for the intended use of the included composition(s) (e.g., for treatment of cancer, hyperproliferative disorders, or arterial restenosis). Instructions supplied in the kits of the invention are typically written instructions on a label or package insert (e.g., a paper sheet included in the kit), but machine-readable instructions (e.g., instructions carried on a magnetic or optical storage disk) are also acceptable.

The patents, patent applications, and publications cited throughout the disclosure are incorporated herein by reference in their entirety.

EXAMPLES

Example 1
Treatment of Nutritionally Stressed HEK293 Kidney Cells with IGFBP-3

Human embryonal kidney 293 (HEK293) cells were grown in Dulbecco's Modified Eagle Medium (D-MEM) supplemented with fetal calf serum at 2%, 4%, 6%, or 8%. When the cells reached 80–85% confluency (cell titer approximately $2.1 \times 10^6$ cells per plate), 5 μg of IGFBP-3 or buffer control was added to each plate. The cells were incubated at 37° C. overnight. The next day the medium was removed and the cells were rinsed with trypsin-EDTA (0.25% trypsin, 1 mM EDTA) plus 1× phosphate buffered saline. The cells were centrifuged and the supernatant was removed. ApoAlert caspase-3 assay kit from Clontech Inc (Palo Alto, Calif.) was used to measure apoptosis. The cells were resuspended in 50 μl of chilled cell lysis buffer and incubated on ice for 10 minutes. The resulting cell, lysates were centrifuged at 14000 rpm in a Beckman microcentrifuge for 3 minutes at 4 C. The supernatant was transferred to new tubes and 50 μl of 2× reaction buffer/DTT plus 5 μl of 1 mM caspase-3 substrate was added to each tube. After incubating at 37 C. for 1 hour in a water bath, the samples were read at 405 nm in a microplate reader. The results of this experiment are shown in FIG. 3.

Example 2
Identification of Pro-Apoptotic Peptide Sequences

As shown in FIG. 4A and disclosed in co-owned U.S. patent application Ser. No. 09/956,508, IGFBP-3 has pro-apoptotic activity. Peptides derived from IGFBP-3 were tested for pro-apoptotic activity essentially as described in Example 1.

The peptides tested are described in Table 1 (peptides marked with an asterisk include a hexahistidine tag).

TABLE 1

| Peptide | FIG. 4B reference |
|---|---|
| Control (no peptide) | A |
| rh (N109D)-IGFBP-3 | B |
| glycosylated CHO-derived rhIGFBP-3 | C |
| rhIGFBP-3/rhIGF-I complex | D |
| rhIGFBP-3/rh(Y60L)-IGF-I complex | E |
| *(KKGHAKDSQRYKVDYESQS)-gfp (SEQ ID NO:6) | F |
| *(KKGFYKKKQCRPSKGRKRGFCW)-gfp (SEQ ID NO:7) | G |
| DKKGFYKKKQCRPSKGRKRGFCW (SEQ ID NO:1) | H |
| QCRPSKGRKRGFCW (SEQ ID NO:3) | I |

Data from this experiment, summarized in FIG. 4B, demonstrated, for the first time, that it was possible to generate IGFBP-3-derived peptides exhibiting greater pro-apoptotic activity (on a weight basis) than intact IGFBP-3 itself. Comparing the pro-apoptotic activity of peptides H and I, it is remarkable that peptide I exhibited 3–4× higher pro-apoptotic activity on a weight basis than intact IGFBP-3 (B, C) or a longer peptide (G, H). That is, the presence of 9 additional amino acids in peptide H compared to peptide I resulted in a dramatic lowering of pro-apoptotic activity.

Example 3
Metal-Binding Properties of IGFBP-3 and Derivative Peptides

Figure 5A:
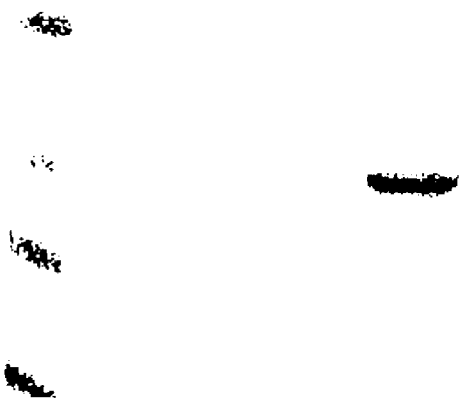
FIGS. 5A–5B shows results of IMAC purification of IGFBP-3 using $Ni^{++}$ and $Zn^{++}$ IMAC. Panels a and b (FIGS. 5A and 5B) show SDS-PAGE analysis of samples from $Ni^{++}$ and $Zn^{++}$ IMAC, respectively. FT indicates column flowthrough; W indicates wash; 50 indicates 50 mM imidazole wash; 60 indicates 60 mM imidazole wash; E indicates 1 M imidazole elution buffer; S indicates 1 M EDTA stripping buffer.
Figure 5B:

As shown in FIG. 5, intact IGFBP-3 binds immobilized nickel and zinc and can be eluted from the resin with 60 mM imidazole. This previously unknown property of IGFBP-3 is intriguing and has a number of practical implications among which the ability to capture products using immobilized metal affinity (IMAC) resins leads to a number of potential applications in therapeutic, high-throughput discovery, and other research arenas.

FIG. 5 shows SDS-PAGE results from IMAC purification of IGFBP-3 using $Ni^{++}$ (panel a) and $Zn^{++}$ (panel b) IMAC. IGFBP-3 bound both IMAC resins effectively.

We further tested the ability of IGFBP-3-derived sub-domains and peptides to bind metal. As shown in Example 5, below, a defined fragment of IGFBP-3 generated in vivo can be captured on IMAC. Two short peptides were passed through a Ni-His-Bind column:

```
                                                    (SEQ ID NO:1)
Peptide 1:  (H2N) . . . DKKGFYKKKQCRPSKGRKRGFCW . . . (COOH);

(SEQ ID NO:3)
Peptide 2:  (H2N) . . . QCRPSKGRKRGFCW . . . (COOH)
```

Both peptides bound specifically to the column. Peptide 1 eluted with 60 mM imidazole, whereas higher concentrations of imidazole (1M) were necessary to elute Peptide 2. It therefore appears that Peptide 2 binds metal more tightly than does Peptide 1.

Example 4
Treatment of LAPC-4 Prostate Tumor Cells with IGFBP-3 and Co-administered Agents A study was performed to analyze the effects of IGFBP-3 in combination with TAXOL® on the growth and death of prostate cancer cells utilizing the LAPC-4 xenograft model. One million cells (in 100 µl) were injected SQ into SCID mice. After 4 weeks palpable tumors were observed. 4 groups were treated (6 mice per group): 1) saline control; 2) IGFBP-3 (4 mg/kg/day intra-peritoneally); 3) TAXOL® (2 mg/kg/day intra-peritoneally on days 5 through 8); 4) TAXOL® and IGFBP-3 combination. Tumors were analyzed for size by palpation weekly and serum collected. Animals were sacrificed at day 21 and tumor weight assessed. The results of this experiment demonstrated a trend for reduced tumor size (40%) with combination therapy. This biological action is believed to result from the pro-apoptotic activity of IGFBP-3.

Example 5
Generation of Defined Sub-domains of IGFBP-3 by Engineering 3C Protease Target Sites into the Primary Sequence of the Protein Defined IGFBP-3 sub-domains were generated from constructs expressed as soluble fusion proteins in an E. Coli expression system. The general structures of the fusions are:

```
IVS-1: DsbA(mut) . . . [3C] . . . domain 1 . . . [3C] . . . domain 2/3

IVS-2: DsbA(mut) . . . [3C] . . . domain 1/2 . . . [3C] . . . domain 3
``` where [3C] is the peptide sequence recognized by HRV 3C proteinase. The general strategy for generating defined domains is shown in FIG. 5. Yields are comparable to wild type, and a substantial fraction is believed to be correctly folded, based on the demonstrated ability of the protein to bind IGF-I. After cleavage, the sub-domains of IGFBP-3 generated from the IVS-1 construct (domains 1, ⅔) are captured on hydrophobic interaction resins such as Phenyl-SEPHAROSE® or (less desirably) on cation exchange resins such as SP-SEPHAROSE®. Other resins, such as immobilized heparin can also be used. Efficient on-column cleavage of IVS-1 fusion with 3C protein-ase has been demonstrated using 1:10 (protease to substrate) ratios at 4 degrees Celsius or room temperature. Complete cleavage has been seen in less than 20 minutes. In the past, amino acid sequencing of cleavage products has shown that the enzyme cleaves in an unusually clean manner (<5% "ragged" ends). Further purification to near homogeneity can be achieved on nickel- or zinc-affinity chromatography. Apparently, metal-binding does not require the amino-terminal ~100 amino acids of the protein, which are believed to constitute the primary domain for IGF-I binding in the IGFBP-3 molecule.

Example 6
Identification of Cell Internalization Peptide

Figure 7:
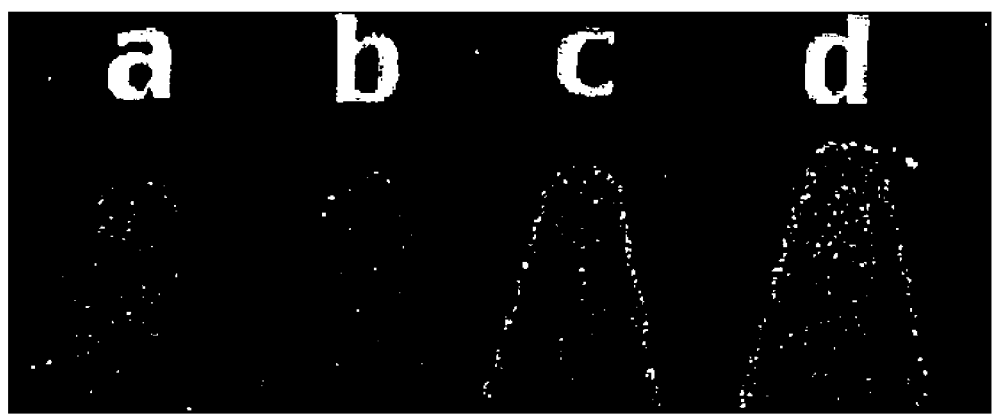
FIG. 7 shows fluorescence of cells after incubation with peptide-gfp fusions. a is cells alone (no gfp added); b is cells plus SYGRKKRRQRRRAHQNSQT-gfp (SEQ ID NO:5); c is cells KKGHAKDSQRYKVDYESQS-gfp (SEQ ID NO:6); d is cells+KKGFYKKKQCRPSKGRKRGFCW-gfp (SEQ ID NO:7).

Three peptide extensions were each cloned in frame with the gene for green fluorescent protein (gfp; Clontech) and expressed in E. coli (JM109). Each construct further contains a 6H tag. Products were captured on His-Bind Resin (Novagen) and eluted with 60 mM imidazole 0.5M NaCl, then further purified on a HIC (Phenyl-SEPHAROSE® High Performance Resin, Amersham) resin and eluted with 50 mM Phosphate Buffered Saline. The purified peptide-gfps were tested for cell internalization on HEK293, a human embryonal kidney cell line. HEK293 cells were cultured in Dulbecco's Modified Eagle Medium until they were 80–85% confluent (~2.1×10^6 cells per plate). Fresh medium containing each peptide (11 µg per plate) was added to the plates. The cells were incubated at 37° C. for approximately thirty minutes. The medium was removed, the cells were trypsinized and washed with 1× Phosphate Buffered Saline twice. Cells were held under a longwave UV lamp to determine fluorescence. Photographs of the samples are shown in FIG. 7. Sample "d" was the only sample that exhibited strong fluorescence. It thus appears that the peptide KKGFYKKKQCRPSKGRKRGFCW (SEQ ID NO:7) contains all the sequence information necessary to direct the internalization of a large, unrelated protein into HEK293 cells. Combined with the known nuclear translocation properties believed to reside in part of this same sequence, this peptide may be useful as a cell uptake and nuclear transporter for a variety of molecules such as proteins, nucleic acids and small chemical moieties. Applications in conventional and gene therapy, cell imaging, research, and high-throughput screening are envisaged.

Example 7
Metal-binding Properties of IGFBP-3

Binding of IGFBP-3 to immobilized metal affinity chromatography (IMAC) resin charged with various metals was measured. Approximately 1 mg of IGFBP-3 was loaded onto each column (NTA resin, Sigma Chemical Co., St. Louis, Mo.). The "percentage bound" was calculated by measuring OD280 of load, flow-through, wash and eluate at 60 mM imidazole. Typical recoveries were 85–95%. Results are summarized in Table 2.

TABLE 2

| Metal | log stability K | % IGFBP-3 bound |
|---|---|---|
| $Ni^{++}$ | 11.5 | 97.6 |
| $Co^{++}$ | 10.8 | 95.1 |
| $Zn^{++}$ | 10.4 | 59.5 |
| $Fe^{3+}$ | 15.9 | 55.1 |
| $Fe^{2+}$ | NA | 46.6 |
| $Mg^{++}$ | 5.5 | 38.8 |
| $Mn^{++}$ | 7.4 | 20.1 |
| $Ca^{++}$ | 6.5 | 0.0 |
| none | | 0.0 |

Example 8
Co-apoptotic Activity of IGFBP-3 and Paclitaxel

Co-aptotic activity of IGFBP-3 in combination with paclitaxel was measured in the HEK293 assay described in Example 1. HEK293 cells were grown in DMEM plus 8% FCS, then incubated in 0.3 ng/ml of paclitaxel (TAXOL®), 50 ng/ml of IGFBP-3, or a combination of the two. Some cultures were pretreated for 30 minutes with 200 ng/ml of anti-beta-1-integrin antibody (Pharmingen). Caspase-3 was assayed using the ApoAlert caspase-3 kit from Clontech Inc.

Results of the experiment shown in FIG. 8. The results shown in FIG. 8A demonstrate the strong co-apoptotic synergy of paclitaxel and IGFBP-3 on HEK293 cells. Pretreatment with anti-beta-1-integrin antibody greatly inhibits the co-apoptotic activity of IGFBP-3 in this assay, as shown in FIG. 8B. However, IGFBP-3 failed to demonstrate any co-apoptotic activity in a similar experiment performed using MDA-MB-231 cells and cisplatin (FIG. 8C).

Example 9
Rapid Cellular Uptake of GFP Directed by MBD2 Peptide

Polynucleotides encoding the peptides KKGHAKDSQRYKVDYESQS (SEQ ID NO:6) (irrelevant peptide GFP31), KKGFYKKKQCRPSKGRKRGFCW (SEQ ID NO:7) (long peptide GFP32), KKGFYKKK (SEQ ID NO:10) (upstream peptide GFP34), and QCRPSKGRKRGFCW (SEQ ID NO:3) (downstream peptide GFP35 which includes MBD2) were cloned as in-frame fusions to the 5' end of the GFP coding sequence in the pGFPuv vector (Clontech Inc., Palo Alto, Calif.). Expressed proteins were purified via metal-affinity and hydrophobic interaction chromatography.

Figure 9A:
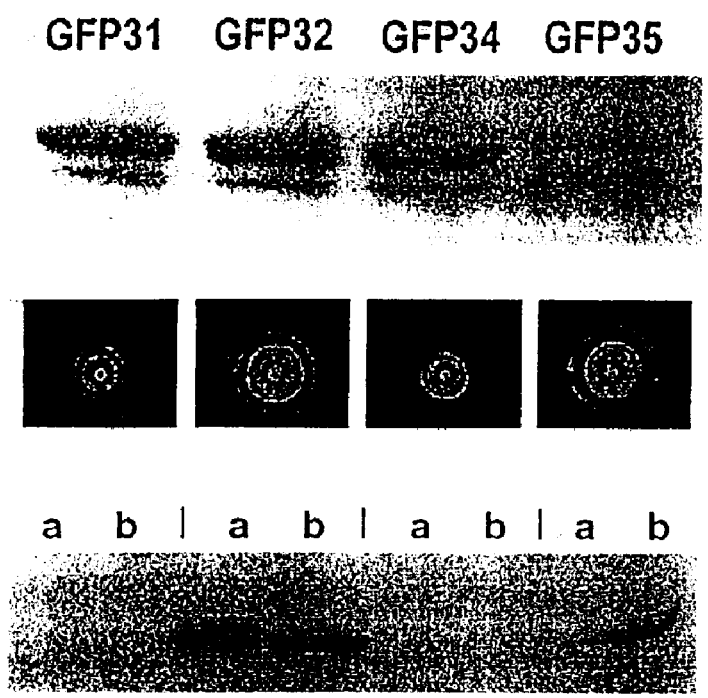
FIGS. 9A–9B shows the results of the cell internalization experiments described in Example 9.
Figure 9B:
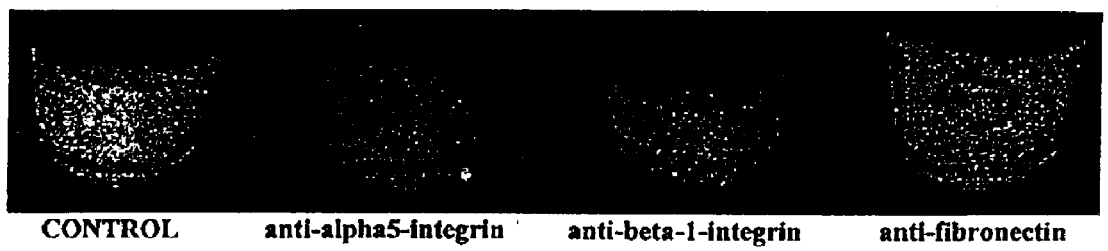

Each protein was added to 80% confluent HEK293 cells at 0.5 µg/ml. FIG. 9A shows, from top to bottom, a Coomassie stained gel of the purified proteins, GFP fluorescence of treated cells 1 hr post-addition and a Western blot of extracts from the same cells (duplicate experiments). Westerns were probed with anti-GFP antibody. FIG. 9B further shows fluorescence of GFP32-treated cells indicating that uptake of GFP32 into these cells can be selectively inhibited by pretreating the cells with 200 ng/ml of anti-integrin but not anti-fibronectin antibodies.

Example 10
Co-apoptotic Activity of MBD Peptides and Paclitaxel

Peptides (50 ng/ml) were added to 80% confluent HEK 293 cells grown in DMEM supplemented with 0.3 ng/ml paclitaxel concurrent with peptide. Caspase-3 activity was measured in cell extracts 8 hours post-addition.

Results are summarized in Table 3. Apoptotic activity is expressed in arbitrary caspase-3 units normalized to MBD2 on a molar basis (MBD2 activity was defined as 100 units (avg. of 3 experiments); "nd" indicates "not done"; "ps" indicates phosphoserine. Metal-binding is expressed as a percentage of loaded peptide bound to a Ni-NTA resin; approximately 1–1.5 mg of peptide were loaded on the column. Cell uptake was determined using genetic fusions to GFP as described in Example 9.

TABLE 3

| Peptide | Sequence | Apoptotic Activity* | Metal-binding | Cell Uptake |
|---|---|---|---|---|
| BP3 | full-length, 264 aa, IGFBP-3 | 585 | 93 | +++ |
| MBD1 | DKKGFYKKKQCRPSKGRKRGFCW (SEQ ID NO:1) | 10–15 | 22 | +++ |
| MBD9 | KKGFYKKKQCRPSKGRKRGFCWNGRK (SEQ ID NO:11) | 149 | 45 | nd |
| MBD5 | GFYKKKQCRPSKGRKRGFCW (SEQ ID NO:2) | 10–15 | 95 | nd |
| MBD2 | QCRPSKGRKRGFCW (SEQ ID NO:3) | 100 | 66 | ++ |
| MBD2*PS | QCRP(pB)KGRKRGFCW (SEQ ID NO:12) | nd | nd | nd |
| MBD3 | QCRPSEGGKGRKRGFCW (SEQ ID NO:13) | <5 | 100 | nd |
| BP2n1s | QCKMSLNGQRGECW (SEQ ID NO:14) | <5 | nd | nd |
| BP5n1s | QCKPSRGRKRGICW (SEQ ID NO:15) | <5 | 28 | nd |
| MBD12 | CRPSKGRKRGFCW (SEQ ID NO:9) | 10–40 | nd | nd |
| MBD13 | QCRPSKGRKRGFC (SEQ ID NO:8) | 10–40 | nd | nd |
| MBD4 | CRPSKGRKRGFC (SEQ ID NO:4) | 10–15 | 92 | nd |
| MBD7 | QCRPSKGRKRGFCWNGR (SEQ ID NO:16) | 89 | 11 | nd |

TABLE 3-continued

| Peptide | Sequence | Apoptotic Activity* | Metal-binding | Cell Uptake |
|---|---|---|---|---|
| MBD10 | KKEKDIMKKTIQCRPSKGRKRGFCWNGR (SEQ ID NO:17) | 127 | nd | nd |

Example 11
Antigenic Profiling of MBD Peptides

The antigenic profiles of MBD peptides were assayed by ELISA. MBD peptides or IGFBP-3 were added to wells of a 96-well Ni-NTA plate (Qiagen Inc., Carlsbad, Calif.) for 15 minutes washed twice in PBS Tween buffer, then blocked for 4 hours with 3% BSA in the same buffer. Detection was done colorimetrically (recorded in absorbance units) using a second antibody conjugated to horse-radish peroxidase.

As shown in FIG. 10, MBD peptides are antigenically distinct from full length IGFBP-3. None of the MBD peptides tested reacted with polyclonal anti-IGFBP-3 antibody, as shown in panel (a). Panel (b) shows the absorbance units obtained using a polyclonal antibody raised to MBD5 peptide, which bound to the MBD peptides, but not IGFBP-3.

Example 12
MBD Co-apoptotic Activity is Resistant to Inhibition by Plasma Proteins Co-apoptotic activity of MBD peptides or IGFBP-3 with paclitaxel was tested in the presence or absence of two plasma proteins; fibronectin and fibrinogen. MBD peptides or IGFBP-3, (50 ng/ml), 0.3 ng/ml paclitaxel, and plasma proteins (200 ng/ml) were added to 80% confluent HEK293 cells grown in DMEM essentially as described in Example 8. Caspase-3 was measured after an eight hour incubation.

Apoptotic activity was calculated in arbitrary caspase-3 units normalized to MBD2 (MBD2 activity was defined as 100 units) Results are summarized in Table 4 (average of 3 experiments). Fibronectin and fibrinogen inhibit IGFBP-3 co-apoptotic activity is essentially eliminated by both fibronectin and fibrinogen, while MBD2 co-apoptotic activity is either essentially unaffected (fibronectin) or only moderately reduced (fibrinogen).

TABLE 4

| Plasma Protein | MBD2 | IGFBP-3 |
|---|---|---|
| none | 100.0 | 100.0 |
| Fibronectin | 98.3 | 3.5 |
| Fibrinogen | 67.5 | 1.1 |

Example 13
Treatment with IGFBP-3 Plus Doxorubicin or 5-fluorouracil Reduces Tumor Size Fragments of MA-16C mammary adenocarcinoma tumors were implanted subcutaneously into female C3H mice (8–11 animals per group). The animals were treated with vehicle alone, IGFBP-3 (4 mg/kg/day for 21 days by subcutaneous injection), doxorubicin (2 mg/kg on days 1 and 8 by intravenous injection), or IGFBP-3 plus doxorubicin. A separate study was performed where the animals were treated with vehicle alone, 5-fluorouracil (10 mg/kg on days 1–5 by intraperitoneal injection), or IGFBP-3 plus 5-fluorouracil. Tumor size was measured at day 18, and the mice were sacrificed at day 21, and the implanted tumors were removed for determination of caspase-3 activity (a marker of apoptosis-only performed for DOX groups).

Treatment with IGFBP-3 combined with either doxorubicin (DOX) or 5-fluorouracil (5FU) significantly reduced tumor size as compared to treatment with vehicle or IGFBP-3 alone (p<0.01). Additionally, tumor shrinkage by IGFBP-3 plus DOX was significant when compared to the DOX alone group (p<0.02). Results for the DOX groups are summarized in Table 5 and results for the 5FU groups are summarized in Table 6.

TABLE 5

| Treatment | Tumor Weight (mg) | Caspase-3 | Lung Metastases |
|---|---|---|---|
| Vehicle | 2878 ± 1025 | 4.42 + 3.77 | 4/8 |
| DOX | 1966 + 677 | 7.88 + 6.27 | 0/12 |
| IGFBP-3 | 2632 + 554 | 3.79 + 3.25 | 1/7 |
| IGFBP-3/DOX | 1033 + 831 | 9.02 + 2.81 | 3/9 |

TABLE 6

| Treatment | Tumor Weight (mg) | Lung Metastases |
|---|---|---|
| Vehicle | 3198 + 1130 | 4/8 |
| 5FU | 2595 + 1767 | 4/10 |
| IGFBP-3 | 3147 + 952 | 1/7 |
| IGFBP-3/5FU | 1779 + 723 | 1/10 |

Example 14
Stimulation of Apoptosis by MBD Peptides is IGF-independent

HEK 293 cells were cultured under stressed conditions (low serum or in the presence of paclitaxel) with and without IGFBP-3 (50 ng/ml) or MBD2 (50 ng/ml). Apoptosis was assayed using the caspase-3 assay as described in Example 1. As shown in FIGS. 11A and 11B, the pro-apoptotic activities of IGFBP-3 and MBD2 are nearly identical.

IGF-dependence was investigated using HEK 293 cells treated with 0.3 ng/ml of paclitaxel in the presence of IGFBP-3 or MBD2, both alone or in combination with Y60L-IGF-I (an IGF-I mutant that does not bind to the IGF receptor). As shown in FIG. 11C, the pro-apoptotic activity of IGFBP-3 and MDB2 are independent of the presence of IGF.

Example 15
The Pro-apoptotic and Cell Internalization Activities of MBD Peptides are Integrin Dependent HEK 293 cells were cultured as described in Example 10, including paclitaxel. Cells were incubated with MDB2 either alone or in combination with an anti-adhesion protein antibody. Antibodies were against integrin associated protein (LAP), fibronectin (Fn), transferrin receptor (TfnR), alpha 5 integrin, alpha 6 integrin, alpha v integrin, beta 1 integrin, and beta 5 integrin. Caspase-3 activity was assayed as described in Example 1.

Results are summarized in FIG. 12A, the pro-apoptotic activity of MBD2 is inhibited by antibodies against integrins and integrin-associated proteins.

Example 16
The Pro-apoptotic Activity of MBD Peptides is Sequence-specific

HEK 293 cells were cultured and assayed as described in Example 10. MBD2 and 6 MBD2 (MBD2(ps) has a phosphoserine at position 5) variants were assayed for co-apoptotic activity. Results are summarized in FIG. 13, which shows that the co-apoptotic activity of MDB peptides is highly sequence specific to the core sequence.

Example 17
Expression of Bax-alpha is Stimulated by IGFBP-3 and MBD Peptides HEK 293 cells were cultured as described in Example 1, with the addition paclitaxel (0.3 ng/ml) and either IGFBP-3 or MBD2 at 50 ng/ml. Bax-alpha and bcl-2 mRNA and caspase 3 activity were assayed. As summarized in FIG. 14A, IGFBP-3 stimulates bax-alpha expression. Bax-alpha expression is correlated with caspase-3 activity, as shown in FIG. 14B.

Figure 15:
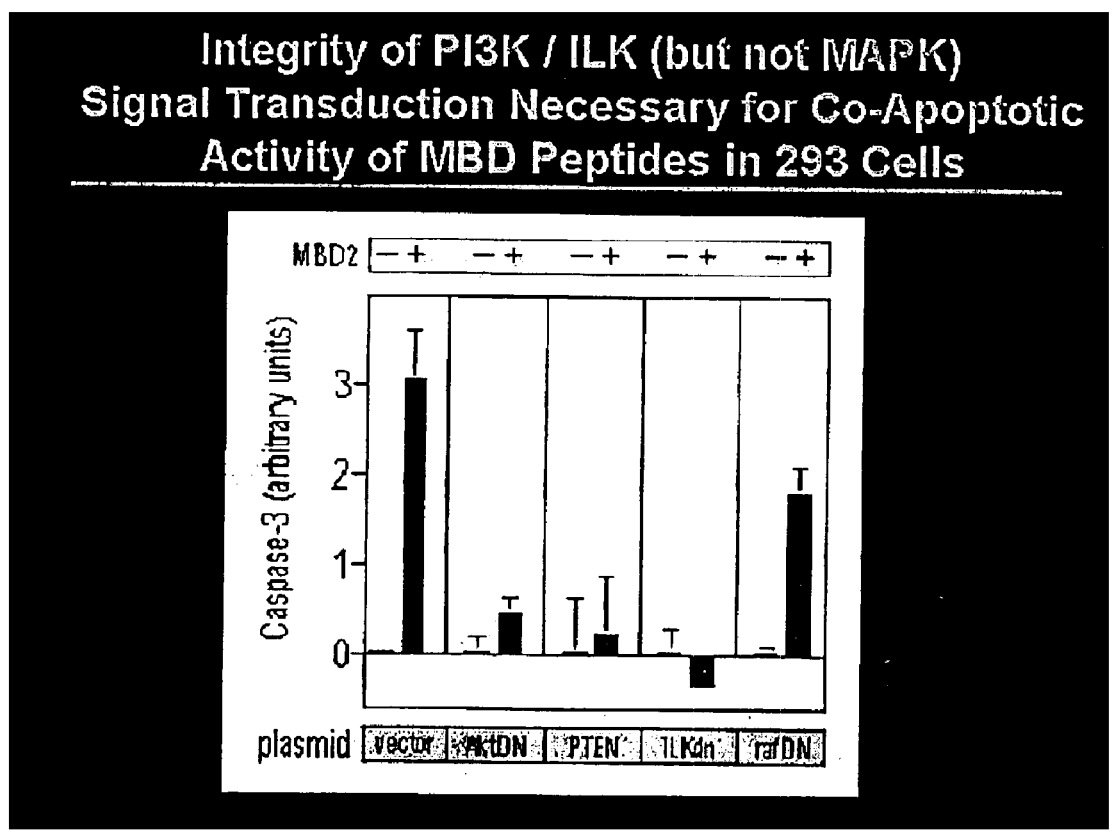
FIG. 15 summarizes the results of experiments showing that the co-apoptotic activity of MDB peptides is dependent on PI3K/ILK, but not MAPK, signal transduction pathways.

Example 18
MBD Co-apoptotic Activity is Dependent on PI3K/ILK Signal Transduction HEK 293 cells were transfected with pUSEamp, or pUSEamp carrying a Akt dominant negative (AktDN), PTEN, ILK dominant negative (ILKdn) or raf dominant negative (rafDN) insert (Upstate Biotechnologies). The cells were cultured as described in Example 10 (including paclitaxel), with or without MBD2. As summarized in FIG. 15, MBD2 pro-apoptotic activity is inhibited in cells in which the PI3K/ILK kinase signal transduction pathway is blocked, but not in cells where the MAPK signal transduction pathway is blocked.

Example 18
MBD Peptides Sensitize Cancer Cells to Low Doses of Cytotoxic Chemotherapy Agents MA16C cells were cultured in the presence of MDB2 and a low dose of doxorubicin (75 ng/ml). Apoptosis was assayed using the caspase-3 assay as described in Example 1. As summarized in FIG. 16A, MDB2 sensitizes MA16C mammary adenocarcinoma cells to low doses of doxorubicin.

MDA-MB-231 cells were cultured in the presence of low dose paclitaxel (100 ng/ml) with and without MDB2 (50 ng/ml). Apoptosis was assayed by measuring NMP levels. As summarized in FIG. 16B, MDB2 sensitizes MDA-MB-231 cells to low doses of paclitaxel.

Example 19
Ferrous Iron Unmasks MBD Peptide Epitopes

One milligram of pure IGFBP-3 was incubated at room temperature in (a) PBS (b) 100 $\mu$M ferrous chloride in PBS, (c) 100 $\mu$M ferric chloride in PBS, or (d) 100 $\mu$M zinc chloride in PBS, either in the presence or absence of 200 ng IGF-I. Aliquots were withdrawn at 0, 20, 40 and 60 minutes, then assayed by ELISA using an anti-MBD antibody.

Figure 17:
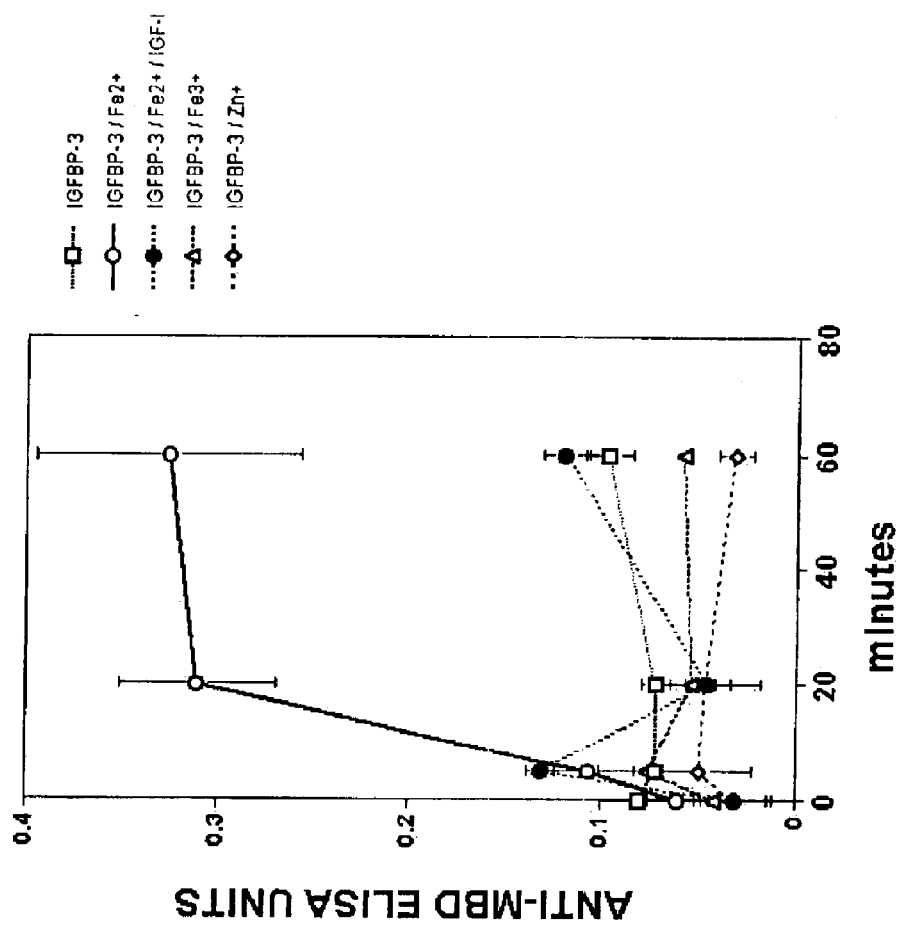
FIG. 17 summarizes the results of the experiment described in Example 19. Open squares indicate data from IGFBP-3 incubated in saline; open circles indicate data from IGFBP-3 incubated with ferrous chloride; closed circles indicate data from IGFBP-3 incubated with IGF-I and ferrous chloride; open triangles indicate data from IGFBP-3 incubated with ferric chloride; and open diamonds indicate data from IGFBP-3 incubated with zinc chloride.

Assay results, summarized in FIG. 17, indicate that incubation of IGFBP-3 with ferrous iron ($Fe^{++}$), but not ferric iron ($Fe^{+++}$) or zinc ($Zn^{++}$) resulted in the unmasking of MBD peptide epitopes that are not normally detectable on full length IGFBP-3.

Example 20
Differential Localization of MBD Peptides 1 mg/ml MBD-GFP32 protein was pre-incubated in (a) PBS (b) 100 $\mu$M ferrous chloride in PBS, (c) 100 $\mu$M ferric chloride in PBS, or (d) 100 $\mu$M zinc chloride in PBS for 60 minutes. 20 minutes after addition of 500 ng/ml MBD-GFP32 to the cell culture medium, nuclear extracts of HEK293 cells were prepared using a Nuclear Extract Kit from Sigma according to the manufacturer's instructions. Extracts were assayed by anti-GFP ELISA.

Figure 18:
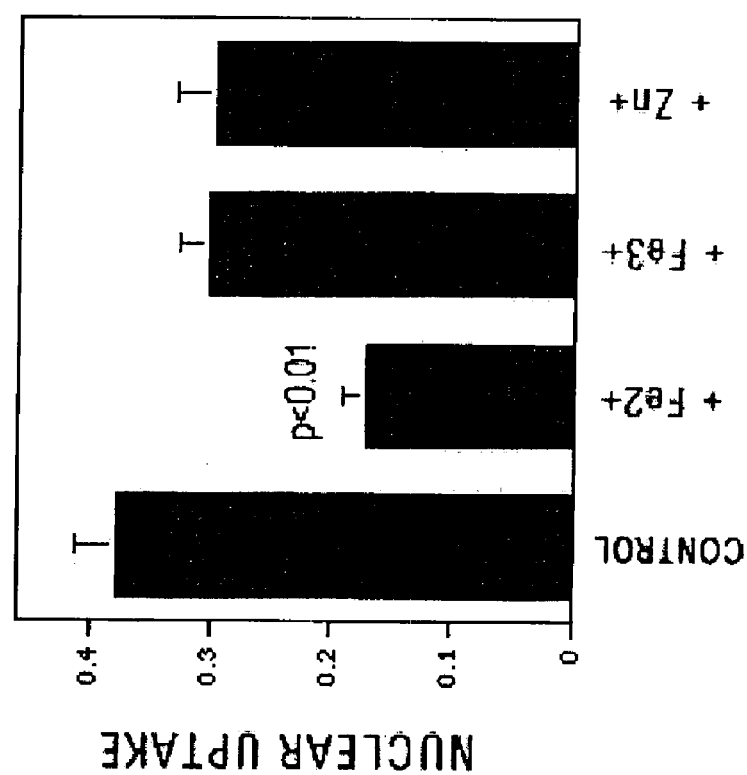
FIG. 18 summarizes the results of the experiment described in Example 20, measuring the effects of preincubation of MBD-GFP32 with certain metals on nuclear translocation. Each bar represents the average of three measurements.

Assay results indicate that preincubation of MBD-GFP32 with ferrous iron, but not ferric iron or zinc, inhibits nuclear localization of the protein. Results are summarized in FIG. 18.

Example 21
Nuclear Translocation of MBD Peptides Involves Caveolin- and Clathrin-mediated Pathways HEK293 cells were pre-incubated with inhibitors nystatin (inhibitor of caveolin pathway) or chlorpromazine (inhibitor of clathrin pathway) for one hour at 10 $\mu$g/ml. Twenty minutes after addition of 500 ng/ml MBD-GFP32 to the cell culture medium, nuclear extracts of the cells were prepared as described in Example 20. Extracts were assayed by anti-GFP ELISA.

Figure 19:
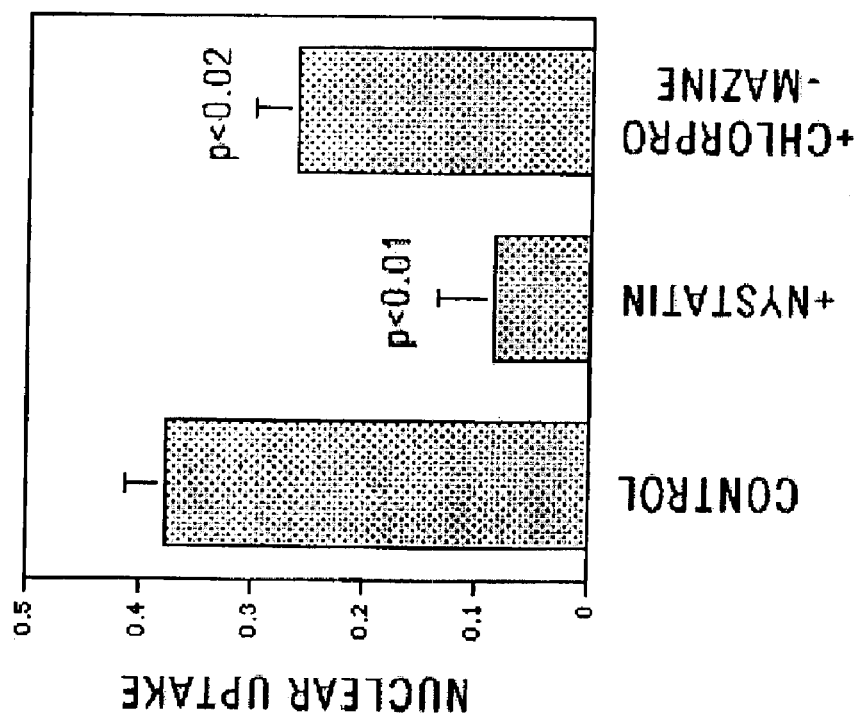
FIG. 19 summarizes the result of an experiment described in Example 21, measuring the effects of nystatin and chlorpromazine on nuclear translocation of MBD peptides. Each bar indicates the average of three plates.

As summarized in FIG. 19, both nystatin and chlorpromazine inhibit nuclear translocation of MBD peptides, suggesting that nuclear translocation of MBD peptides is mediated by both the caveolin and clathrin mediated endocytosis pathways. Results shown are averages of three plates per data point.

In an additional set of experiments, HEK293 cells were pre-incubated with no inhibitor (control), nystatin or chlorpromazine (10 $\mu$g/ml) for 60 minutes, then cooled to 4° Celsius. Cells were gently removed from the plate in the absence of trypsin and incubated in 500 ng/ml MBD-GFP32. Cross-linker B3 was added for 10 minute pulses at various times after the addition of MBD-GFP32 to the cells. Cross-linking reactions were terminated with 100 mM Tris buffer pH 8.0. Cell extracts were captured on Nickel-NTA-coated 96-well plates, then assayed by ELISA using antibodies to GFP (for standardization of samples), transferrin receptor, or alpha 5 integrin.

Figure 20:
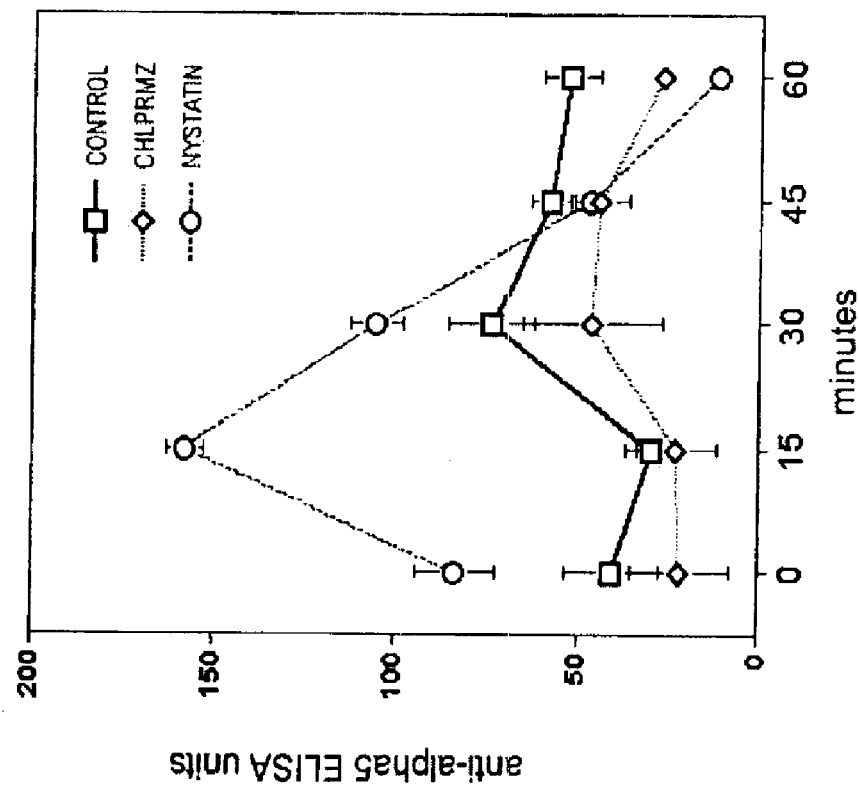
FIG. 20 summarizes the result of an experiment described in Example 21, measuring the effects of nystatin and chlorpromazine on the association of MBD peptides with $\alpha 5$ integrin. Data from cells treated with chlorpromazine is indicated by open diamonds. Data from cells treated with nystatin is indicated by open circles. Data from control (untreated) cells is indicated by open squares.
Figure 21:
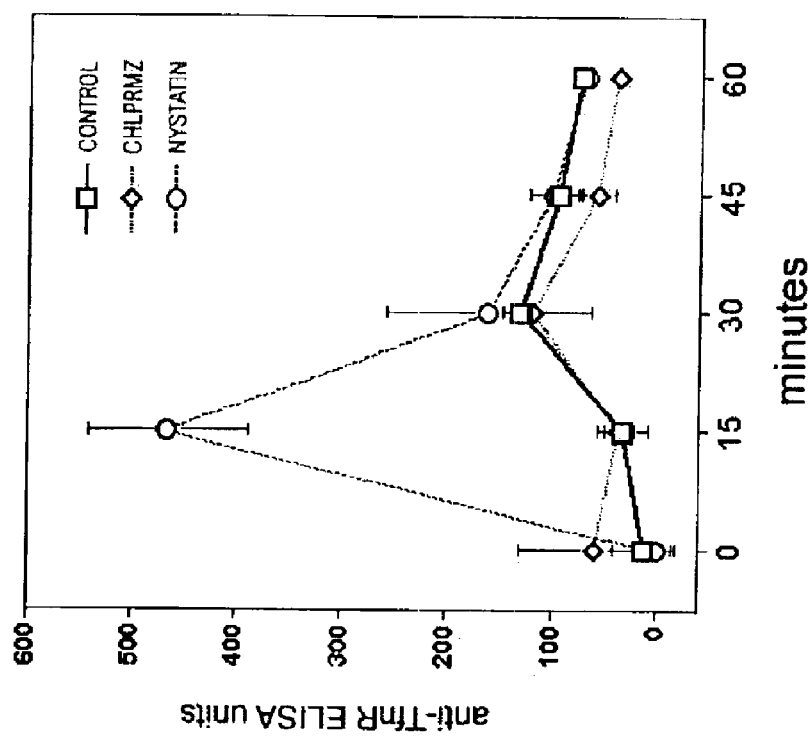
FIG. 21 summarizes the result of an experiment described in Example 21, measuring the effects of nystatin and chlorpromazine on the association of MBD peptides with the transferrin receptor. Data from cells treated with chlorpromazine is indicated by open diamonds. Data from cells treated with nystatin is indicated by open circles. Data from control (untreated) cells is indicated by open squares.

Assay results, summarized in FIGS. 20 and 21, show that both nystatin (an inhibitor of the caveolin-mediated endocytosis pathway) and chlorpromazine (an inhibitor of the clathrin-mediated endocytosis pathway) inhibit association between MBD peptides and cell surface markers. Results shown are averages of triplicates.

Example 22
Differential Localization of MBD Peptides

Female C3H mice were pretreated for 18 days with either subcutaneous injections of MBD7 peptide (2 mg/kg/day) or saline. A single intravenous bolus of MBD-GFP32 or MBD-GFP37 (MBD37 peptide, KKGFYKKKQCRPSKGRKRG-FCWNGR (SEQ ID NO:39) linked to GFP) protein was administered at 2 mg/kg, followed by sacrifice and tissue harvest two hours later.

Figure 22:
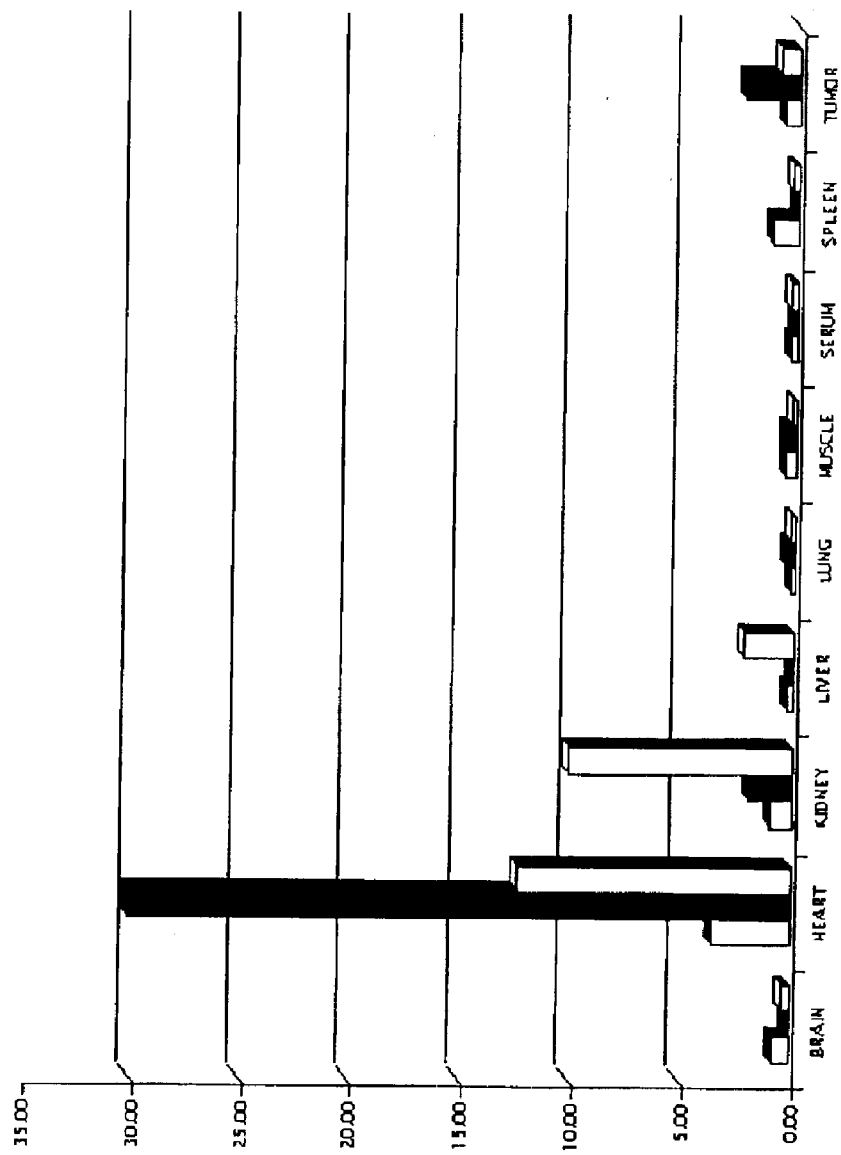
FIG. 22 summarizes the results of an experiment investigating the distribution of MBD-GFP conjugates. For each tissue, data is presented, left to right, for saline, MBD-GFP32, and MBD-GFP37. Each bar represents the average of the measurements from three animals.
Figure 23:
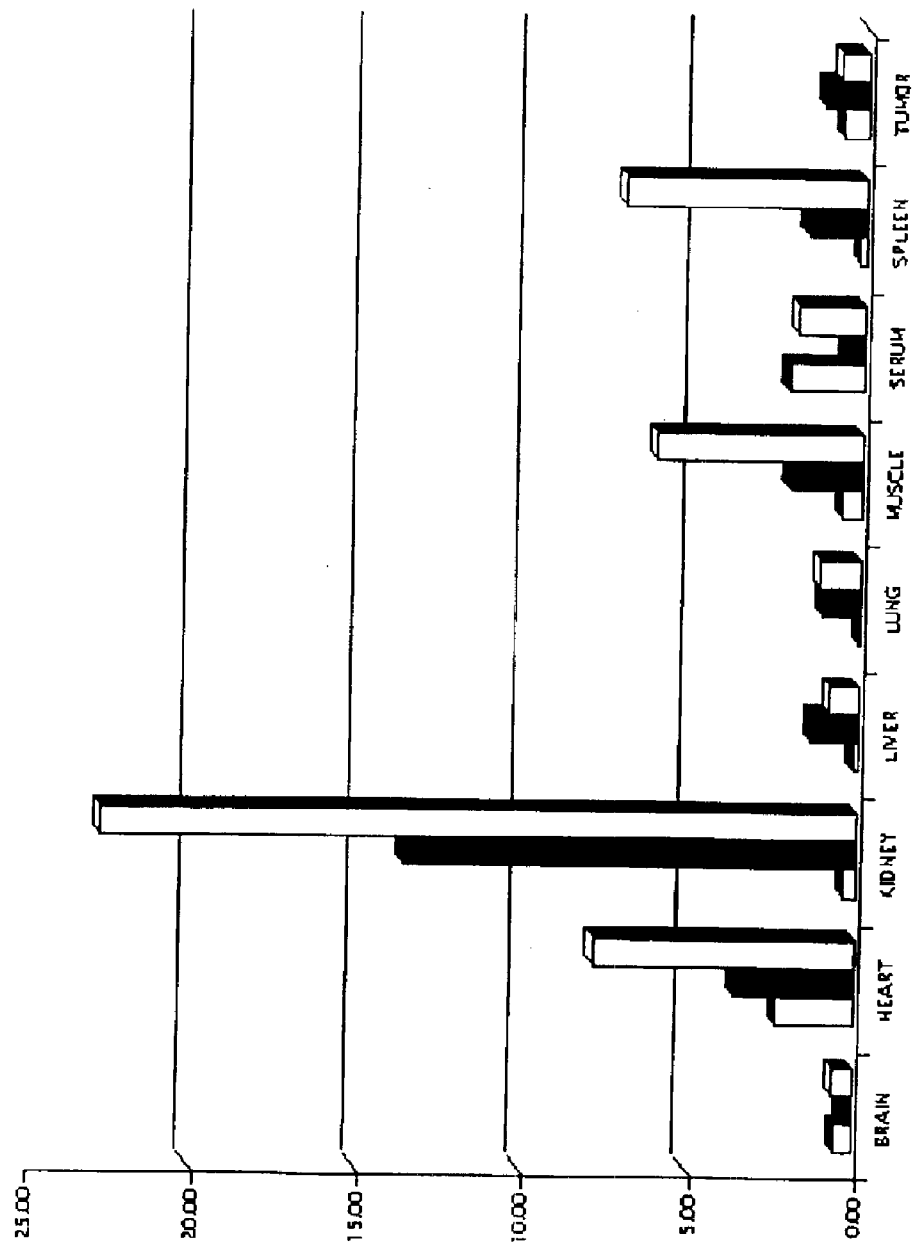
FIG. 23 summarizes the results of an experiment investigating the distribution of MBD-GFP conjugates following 18 days of pretreatment with mMBD7. For each tissue, data is presented, left to right, for saline, MBD-GFP32, and MBD-GFP37. Each bar represents the average of the measurements from three animals.

Tissue extracts were prepared and analyzed by anti-GFP ELISA. As summarized in FIGS. 22 and 23, the distribution of MBD peptides is highly unusual, and is altered by pretreatment with MBD peptide. Preferential targeting to heart and kidney correlates well with data obtained in iron-loading studies in which cardio and renal toxicities have been observed

Example 23
MBD-peptide-mediated Nuclear Translocation of Macromolecules is Greatly Enhanced by Presence of Caveolin-binding Consensus Sequence Biotinylated MBD peptides MBD9, MBD20 (QCRPSKGRKRGFCWAVDKYG (SEQ ID NO: 37): the MBD core 14mer is underlined, and the caveolin consensus binding sequence is bolded) or MBD21 ( KKGFYKKKQCRPSKGRKRGFCWAVDKYG (SEQ ID NO: 38): the MBD core 14mer is underlined, and the caveolin consensus binding sequence is bolded) were each mixed with streptavidin-horseradish peroxidase conjugate (3–6× molar excess of MBD peptide) and added to HEK293 cells. After 20 minutes, nuclear and cytoplasmic extracts were prepared as described in Example 20 and assayed for peroxidase activity.

Figure 24:
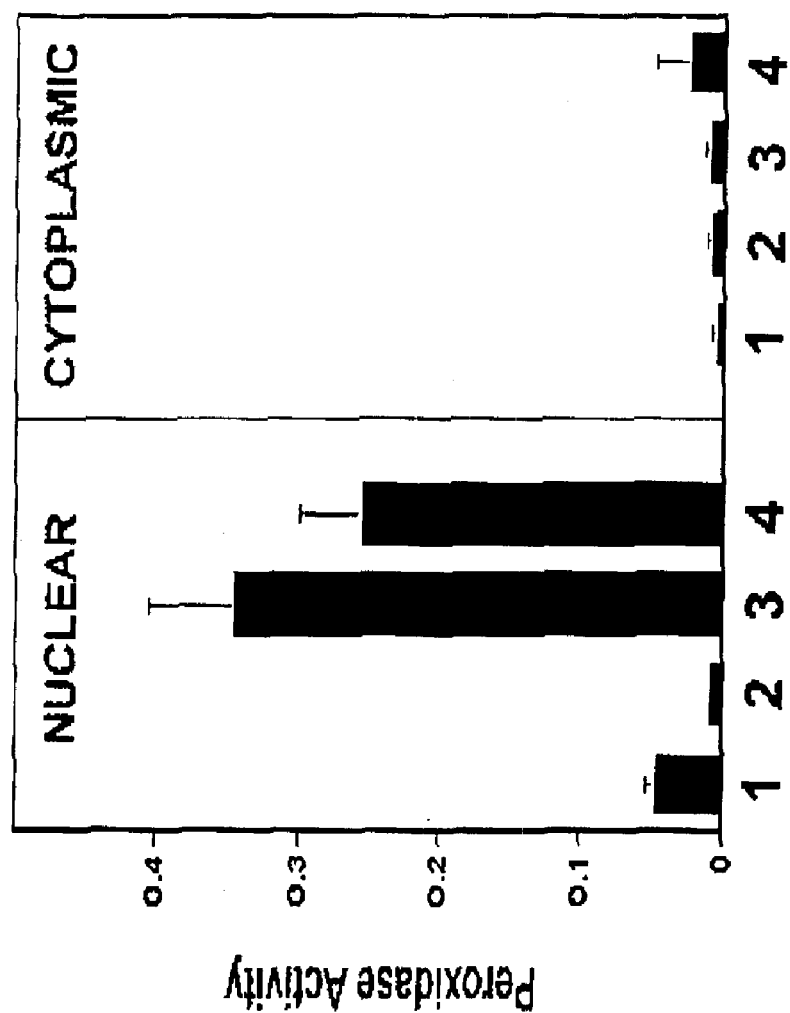
FIG. 24 summarizes the results of the experiment described in Example 21, measuring nuclear translocation of biotinylated peptides MBD9, MBD20, and MBD21 complexed with streptavidin horse radish peroxidase (HRP). Column 1 designates results from control (no peptide); column 2 designates results from MBD9/HRP conjugate; column 3 designates results from MBD20/HRP conjugate; column 4 designates results from MBD21/HRP conjugate.

Assay results, summarized in FIG. 24, show that efficient nuclear mobilization of this large (approx. 90 Kd) conjugate proceeded far more efficiently when MBD20 or MBD21 was used, as opposed to MBD9. There is no detectable cytoplasmic peroxidase activity. The notable difference between the sequences of these peptides is the presence of an additional 6 amino acids on the C-terminal side of the core MBD 14-mer sequence (present in the canonical MBD2 peptide) in both MBD20 and MBD21 but not MBD9. The presence of this sequence completes a motif known to be present in proteins that bind caveolin (#x#xxxx#, where '#' is an aromatic amino acid). The use of the MBD20 sequence to mobilize the rapid uptake of a large molecule from outside living cells directly into the nucleus is potentially very significant, particularly in applications involving nucleic acids (such as gene therapy) as well as modulators of nucleic acid activity.

The present invention has been detailed both by direct description and by example. Equivalents and modifications of the present invention will be apparent to those skilled in the art, and are encompassed within the scope of the invention.

I claim:

1. A composition comprising an isolated MBD peptide, wherein said peptide is DKKGFYKKKQCRPSKGRKRGFCW (SEQ ID NO:1) or QCRPSKGRKRCGFCW (SEQ ID NO:3).

2. The composition of claim 1, wherein said peptide is DKKGFYKKKQCRPSKGRKRGFCW (SEQ ID NO:1).

3. The composition of claim 1, wherein said peptide is QCRPSKGRKRGFCW (SEQ ID NO:3).

4. A composition comprising an isolated MBD peptide, wherein said peptide comprises a sequence selected from the group consisting of QCRPSKGRKRGFCWAVDKYG (SEQ ID NO:37) and KKGFYKKKQCRPSKGRKRGFCWAVDKYG (SEQ ID NO:38).

5. The composition of claim 4, wherein said MBD peptide comprises the sequence QCRPSKGRKRGFCWAVDKYG (SEQ ID NO:37).

6. The composition of claim 4, wherein said MBD peptide comprises the sequence KKGFYKKKQCRPSKGRKRGFCWAVDKYG (SEQ ID NO:38).

7. A method for alleviating a symptom of a cancer, comprising administering an effective amount of an isolated MBD peptide to an individual suffering from said cancer, wherein said MBD peptide is a peptide selected from the group consisting of QCRPSKGRKRGFCW (SEQ ID NO:3), QCRPSKGRKRGFCWAVDKYG (SEQ ID NO:37), and KKGFYKKKQCRPSKGRKRGFCWAVDKYG (SEQ ID NO:38).

8. The method of claim 7, wherein the cancer is selected from the group consisting of breast, prostate, colon, ovarian, pancreatic, gastric and lung cancer.

9. The method of claim 7, wherein a co-administered agent is administered to the individual.

10. The method of claim 9, wherein the co-administered agent is a chemical agent selected from the group consisting of doxorubicin, paclitaxel, methotrexate, tamoxifen, cyclophosphamide, vincristine, etoposide, streptozotocin and 5-fluorouracil.

11. The method of claim 10, wherein said cancer is prostate cancer.

12. The method of claim 11, wherein said co-administered agent is paclitaxel.

13. The method of claim 7, wherein said MBD peptide is administered at about 0.001 to about 40 milligrams per kilogram total body weight per day (mg/kg/day).

14. The method of claim 7, wherein said MBD peptide is QCRPSKGRKRGFCW (SEQ ID NO:3).

15. The method of claim 7, wherein said MBD peptide is QCRPSKGRKRGFCWAVDKYG (SEQ ID NO:37.

16. The method of claim 7, wherein said MBD peptide is KKGFYKKKQCRPSKGRKRGFCWAVDKYG (SEQ ID NO:38).

17. A method for intracellular delivery of a therapeutic molecule to cells of a subject, comprising:

administering a conjugate of an isolated MBD peptide and the therapeutic molecule to said subject, wherein said MBD peptide comprises cell internalization activity, and wherein said peptide is a peptide selected from the group consisting of DKKGFYKKKQCRPSKGRKRGFCW (SEQ ID NO:1), GFYKKKQCRPSKGRKRGFCW (SEQ ID NO:2), QCRPSKGRKRGFCW (SEQ ID NO:3), QCRPSKGRKRGFC (SEQ ID NO:8), CRPSKGRKRGFCW (SEQ ID NO:9), and CRPSKGRKRGFC (SEQ ID NO:4).

18. The method of claim 17, wherein said MBD peptide is further linked to a caveolin consensus binding site.

19. The method of claim 17, wherein said MBD peptide is DKKGFYKKKQCRPSKGRKRGFCW (SEQ ID NO:1).

20. The method of claim 17, wherein said MBD peptide is GFYKKKQCRPSKGRKRGFCW (SEQ ID NO:2).

21. The method of claim 17, wherein said MBD peptide is QCRPSKGRKRGFCW (SEQ ID NO:3).

22. The method of claim 17, wherein said MBD peptide is QCRPSKGRKRGFC (SEQ ID NO:8).

23. The method of claim 17, wherein said MBD peptide is CRPSKGRKRGFCW (SEQ ID NO:9).

24. The method of claim 17, wherein said MBD peptide is CRPSKGRKRGFC (SEQ ID NO:4).

25. A method for intracellular delivery of a therapeutic molecule to cells of a subject, comprising:

administering a conjugate of an isolated MBD peptide and the therapeutic molecule to said subject, wherein said MBD peptide comprises cell internalization activity, and wherein said peptide comprises a sequence selected from the group consisting of QCRPSKGRKRGFCWAVDKYG (SEQ ID NO:37) and KKGFYKKKQCRPSKGRKRGFCWAVDKYG (SEQ ID NO:38).

26. The method of claim 25, wherein said MBD peptide comprises the sequence QCRPSKGRKRGFCWAVDKYG (SEQ ID NO:37).

27. The method of claim 25, wherein said MBD peptide comprises the sequence KKGFYKKKQCRPSKGRKRGFCWAVDKYG (SEQ ID NO:38).

* * * * *

UNITED STATES PATENT AND TRADEMARK OFFICE
CERTIFICATE OF CORRECTION

PATENT NO. : 6,914,049 B2 Page 1 of 1
APPLICATION NO. : 10/383999
DATED : July 5, 2005
INVENTOR(S) : Desmond Mascarenhas It is certified that error appears in the above-identified patent and that said Letters Patent is hereby corrected as shown below:

In Claim 1, column 57, line 2, please replace "1. A composition comprising an isolated MBD peptide, wherein said peptide is DKKGFYKKKQCRPSKGRKRGFCW (SEQ ID NO:1) or QCRPSKGRKRCGFCW (SEQ ID NO:3)."
with
--1. A composition comprising an isolated MBD peptide, wherein said peptide is DKKGFYKKKQCRPSKGRKRGFCW (SEQ ID NO:1) or QCRPSKGRKRGFCW (SEQ ID NO:3).--

Signed and Sealed this

Twenty-ninth Day of August, 2006

JON W. DUDAS
*Director of the United States Patent and Trademark Office*